United States Patent
Turner et al.

(12)

(10) Patent No.: US 6,548,271 B1
(45) Date of Patent: Apr. 15, 2003

(54) NUCLEIC ACIDS ENCODING HUMAN TRANSPORTER PROTEINS

(75) Inventors: Alex Turner, The Woodlands, TX (US); Brian Zambrowicz, The Woodlands, TX (US); Michael Nehls, Stockdorf (DE); Glenn A. Friedrich, The Woodlands, TX (US); Arthur T. Sands, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 09/556,916

(22) Filed: Apr. 21, 2000

Related U.S. Application Data

(60) Provisional application No. 60/130,552, filed on Apr. 22, 1999.

(51) Int. Cl.[7] .......................... C07H 21/02; C07H 21/04; C12N 1/20; C12N 15/63
(52) U.S. Cl. ................. 435/69.1; 435/71.1; 435/320.1; 435/252.3; 435/471; 536/23.1; 536/23.5; 536/24.31
(58) Field of Search ............................. 536/23.1, 23.5, 536/624.31, 24.33; 435/69.1, 71.1, 320.1, 252.3, 471

(56) References Cited

U.S. PATENT DOCUMENTS

| | | | |
|---|---|---|---|
| 5,618,677 A | 4/1997 | Ni et al. .................. 435/7.1 |
| 5,686,266 A | 11/1997 | Ni et al. .................... 435/69.1 |
| 5,882,926 A | 3/1999 | Amara et al. ............... 435/325 |
| 5,985,604 A | 11/1999 | Lal et al. .................... 435/69.1 |

FOREIGN PATENT DOCUMENTS

| | | |
|---|---|---|
| WO | WO 96/34288 | 10/1996 |
| WO | WO 98/37175 | 8/1998 |

OTHER PUBLICATIONS

Markovich et al. Proceedings of the National Academy of Sciences, USA. (Sep. 1993) 90: 8073–8077.*
Auffray et al. C.R. Acad. Sci III Vie. (1995) 318: 263–272.*
Auffray et al., 1994, "*H. sapiens* partial cDNA sequence; clone c–1bf12," Database EMBL [online], Accession No. Z43427.
Girard et al., 1999, "Molecular cloning and functional analysis of SUT–1, a sulfate transporter from human high endothelial venules," *Proc. Natl. Acad. Sci. U.S.A.* 96(22):12772–12777.
Khatri et al., 1996, "Cloning of the cDNA for a rat intestinal $Na^+$/dicarboxylate cotransporter reveals partial sequence homology with a rat intestinal mucin," *Biochimica et Biophysica Acta 1309*:58–62.
Norbis et al., 1994, "cDNA cloning of a rat small–intestinal $Na^+$/$SO_4^{2-}$-cotransporter," *Pflügers Arch. European Jouranl of Physiology 428*:217–223.

\* cited by examiner

*Primary Examiner*—Carla J. Myers

(57) ABSTRACT

The present invention provides two novel families of novel human transporter proteins (NTPs). The invention additionally provides for agonists, antagonists, antibodies, antisense molecules that are specific for the NTPs, and further provides genetically engineered expression vectors for the NTPs and host comprising the same. The invention further provides for processes for identifying/producing molecules that effect NTP activity which comprise the use of the disclosed NTPs or genes encoding the same.

9 Claims, No Drawings

SEQUENCE LISTING

<160> NUMBER OF SEQ ID NOS: 32

<210> SEQ ID NO 1
<211> LENGTH: 1884
<212> TYPE: DNA
<213> ORGANISM: Homo sapiens

<400> SEQUENCE: 1

```
atgggcctgc tgcagggcct gctccgagtc cggaagctgc tgctggtcgt ctgcgtcccg      60
ctcctgctgc tgcctctgcc cgtcctccac cccagcagcg aggcctcgtg tgcttacgtg     120
ctgatcgtga ctgctgtgta ctgggtgtcg gaggcagtgc tctgggagc tgcagccctg     180 gtgccggcct tcctytaccc gttcttcgga gtcctccggt ccaatgaggt ggcggcggag     240
tacttcaaga acaccacgct gctgctggtg ggggtcatct gcgtggcggc tgccgtggag     300
aagtggaacc tgcataagcg cattgctctg cgcatggtct tgatggccgg rgccaagccg     360
ggcatgctgc tgctctgctt catgtgctgt accacgttgc tgtccatgtg gctgtccaac     420
acctccacca ccgccatggt gatgcccatc gtggaggccg tgctgcagga gctggtcagt     480
gctgaggacg agcagctcgt ggcgggcaac tccaacaccg aagaggccga acccatcagt     540
ctggatgtaa agaacagcca accttctctg gaactcatct ttgtcaatga agacaggtcc     600
```

```
aacgcagacc tcaccactct gatgcacaac gagaacctga atggtgtgcc ctcgatcacc      660
aaccccatca aaactgcaaa ccaacaccag ggcaagaagc aacacccatc ccaggaaaag      720
ccacaagtcc tgaccccag ccccaggaag cagaagctga acagaaagta caggtcccac       780
catgaccaga tgatctgcaa gtgcctctcc ctgagcatat cctactccgc taccattggc      840
ggcctgacca ccatcatcgg cacctccacc agcctcatct tcctggaaca cttcaacaac      900
cagtatccag ccgcagaggt ggtgaacttt ggcacctggt tcctcttcag cttccccata      960
tccctcatca tgctggtggt cagctggttc tggatgcact ggctgttcct gggctgcaat     1020
tttaaagaga cctgctctct gagcaagaag aagaagacca aagggaaca gttgtcagag      1080 aagaggatcc aagaagaata tgaaaaactg ggagacatta gctacccaga atggtgact     1140 ggattttct tcatcctgat gaccgtactg tggtttaccc gggagcctgg ctttgtccct      1200
ggctgggatt ctttctttga aagaaaggc taccgtactg atgccacagt ctctgtcttc      1260
cttggcttcc tcctcttcct cattccagcg aagaagccct gctttgggaa aagaatgat      1320 ggagagaacc aggagcactc actggggacc gagcccatca tcacgtggaa ggacttccag      1380
aagaccatgc cctgggagat tgtcattctg gttgggggag gctatgctct ggcttctggt      1440
agcaagagct ctggcctctc tacatggatt gggaaccaga tgttgtccct gagcagcctc      1500
ccaccgtggg ctgtcaccct gctggcatgc atcctcgtgt ccattgtcac tgagtttgtg     1560
agcaacccag caaccatcac catcttcctg cccatcctgt gcagcctgtc tgaaacgctg     1620
cacattaacc ccctctacac cctgatccca gtcaccatgt gcatctcctt tgcagtgatg     1680
ctgcctgtgg gcaatccccc taatgccatc gtcttcagct atgggcactg ccagatcaaa     1740
gatatggtga aagctggcct gggagtcaac gttattggac tggtgatagt aatggtggcc     1800
atcaacacct ggggagttag cctcttccac ctggacactt acccagcatg ggcgagggtc     1860
agcaacatca ctgatcaagc ctaa                                            1884
```

<210> SEQ ID NO 2
<211> LENGTH: 627
<212> TYPE: PRT
<213> ORGANISM: Homo sapiens

<400> SEQUENCE: 2

```
Met Gly Leu Leu Gln Gly Leu Leu Arg Val Arg Lys Leu Leu Leu Val
 1               5                   10                  15

Val Cys Val Pro Leu Leu Leu Pro Leu Pro Val Leu His Pro Ser
                20                  25                  30

Ser Glu Ala Ser Cys Ala Tyr Val Leu Ile Val Thr Ala Val Tyr Trp
            35                  40                  45

Val Ser Glu Ala Val Pro Leu Gly Ala Ala Ala Leu Val Pro Ala Phe
        50                  55                  60

Leu Tyr Pro Phe Phe Gly Val Leu Arg Ser Asn Glu Val Ala Ala Glu
65                  70                  75                  80

Tyr Phe Lys Asn Thr Thr Leu Leu Leu Val Gly Val Ile Cys Val Ala
                85                  90                  95

Ala Ala Val Glu Lys Trp Asn Leu His Lys Arg Ile Ala Leu Arg Met
                100                 105                 110

Val Leu Met Ala Gly Ala Lys Pro Gly Met Leu Leu Leu Cys Phe Met
            115                 120                 125

Cys Cys Thr Thr Leu Leu Ser Met Trp Leu Ser Asn Thr Ser Thr Thr
        130                 135                 140
```

-continued

```
Ala Met Val Met Pro Ile Val Glu Ala Val Leu Gln Glu Leu Val Ser
145                 150                 155                 160

Ala Glu Asp Glu Gln Leu Val Ala Gly Asn Ser Asn Thr Glu Glu Ala
            165                 170                 175

Glu Pro Ile Ser Leu Asp Val Lys Asn Ser Gln Pro Ser Leu Glu Leu
            180                 185                 190

Ile Phe Val Asn Glu Asp Arg Ser Asn Ala Asp Leu Thr Thr Leu Met
            195                 200                 205

His Asn Glu Asn Leu Asn Gly Val Pro Ser Ile Thr Asn Pro Ile Lys
210                 215                 220

Thr Ala Asn Gln His Gln Gly Lys Lys Gln His Pro Ser Gln Glu Lys
225                 230                 235                 240

Pro Gln Val Leu Thr Pro Ser Pro Arg Lys Gln Lys Leu Asn Arg Lys
                245                 250                 255

Tyr Arg Ser His His Asp Gln Met Ile Cys Lys Cys Leu Ser Leu Ser
            260                 265                 270

Ile Ser Tyr Ser Ala Thr Ile Gly Gly Leu Thr Thr Ile Ile Gly Thr
        275                 280                 285

Ser Thr Ser Leu Ile Phe Leu Glu His Phe Asn Asn Gln Tyr Pro Ala
290                 295                 300

Ala Glu Val Val Asn Phe Gly Thr Trp Phe Leu Phe Ser Phe Pro Ile
305                 310                 315                 320

Ser Leu Ile Met Leu Val Val Ser Trp Phe Trp Met His Trp Leu Phe
                325                 330                 335

Leu Gly Cys Asn Phe Lys Glu Thr Cys Ser Leu Ser Lys Lys Lys Lys
            340                 345                 350

Thr Lys Arg Glu Gln Leu Ser Glu Lys Arg Ile Gln Glu Glu Tyr Glu
        355                 360                 365

Lys Leu Gly Asp Ile Ser Tyr Pro Glu Met Val Thr Gly Phe Phe Phe
        370                 375                 380

Ile Leu Met Thr Val Leu Trp Phe Thr Arg Glu Pro Gly Phe Val Pro
385                 390                 395                 400

Gly Trp Asp Ser Phe Phe Glu Lys Lys Gly Tyr Arg Thr Asp Ala Thr
                405                 410                 415

Val Ser Val Phe Leu Gly Phe Leu Leu Phe Leu Ile Pro Ala Lys Lys
                420                 425                 430

Pro Cys Phe Gly Lys Lys Asn Asp Gly Glu Asn Gln Glu His Ser Leu
            435                 440                 445

Gly Thr Glu Pro Ile Ile Thr Trp Lys Asp Phe Gln Lys Thr Met Pro
450                 455                 460

Trp Glu Ile Val Ile Leu Val Gly Gly Tyr Ala Leu Ala Ser Gly
465                 470                 475                 480

Ser Lys Ser Ser Gly Leu Ser Thr Trp Ile Gly Asn Gln Met Leu Ser
            485                 490                 495

Leu Ser Ser Leu Pro Pro Trp Ala Val Thr Leu Leu Ala Cys Ile Leu
                500                 505                 510

Val Ser Ile Val Thr Glu Phe Val Ser Asn Pro Ala Thr Ile Thr Ile
            515                 520                 525

Phe Leu Pro Ile Leu Cys Ser Leu Ser Glu Thr Leu His Ile Asn Pro
        530                 535                 540

Leu Tyr Thr Leu Ile Pro Val Thr Met Cys Ile Ser Phe Ala Val Met
545                 550                 555                 560
```

```
Leu Pro Val Gly Asn Pro Pro Asn Ala Ile Val Phe Ser Tyr Gly His
            565                 570                 575

Cys Gln Ile Lys Asp Met Val Lys Ala Gly Leu Gly Val Asn Val Ile
            580                 585                 590

Gly Leu Val Ile Val Met Val Ala Ile Asn Thr Trp Gly Val Ser Leu
            595                 600                 605

Phe His Leu Asp Thr Tyr Pro Ala Trp Ala Arg Val Ser Asn Ile Thr
    610                 615                 620

Asp Gln Ala
625

<210> SEQ ID NO 3
<211> LENGTH: 1884
<212> TYPE: DNA
<213> ORGANISM: Homo sapiens

<400> SEQUENCE: 3
atgggcctgc tgcagggcct gctccgagtc cggaagctgc tgctggtcgt ctgcgtcccg      60
ctcctgctgc tgcctctgcc cgtcctccac cccagcagcg aggcctcgtg tgcttacgtg     120
ctgatcgtga ctgctgtgta ctgggtgtcg gaggcagtgc tctgggagc tgcagccctg     180
gtgccggcct tcctytaccc gttcttcgga gtcctccggt ccaatgaggt ggcggcggag     240
tacttcaaga caccacgct gctgctggtg ggggtcatct gcgtggcggc tgccgtggag     300
aagtggaacc tgcataagcg cattgctctg cgcatggtct tgatggccgg rgccaagccg     360
ggcatgctgc tgctctgctt catgtgctgt accacgttgc tgtccatgtg gctgtccaac     420
acctccacca ccgccatggt gatgcccatc gtggaggccg tgctgcagga gctggtcagt     480
gctgaggacg agcagctcgt ggcgggcaac tccaacaccg aagaggccga acccatcagt     540
ctggatgtaa agaacagcca accttctctg gaactcatct ttgtcaatga agacaggtcc     600
aacgcagacc tcaccactct gatgcacaac gagaacctga atggtgtgcc ctcgatcacc     660
aaccccatca aaactgcaaa ccaacaccag ggcaagaagc aacacccatc ccaggaaaag     720
ccacaagtcc tgaccccag ccccaggaag cagaagctga acagaaagta caggtcccac     780
catgaccaga tgatctgcaa gtgcctctcc ctgagcatat cctactccgc taccattggc     840
ggcctgacca ccatcatcgg cacctccacc agcctcatct tcctggaaca cttcaacaac     900
cagtatccag ccgcagaggt ggtgaacttt ggcacctggt tcctcttcag cttccccata     960
tccctcatca tgctggtggt cagctggttc tggatgcact ggctgttcct gggctgcaat    1020
tttaaagaga cctgctctct gagcaagaag aagaagacca aaaggggaaca gttgtcagag    1080
aagaggatcc aagaagaata tgaaaaactg ggagacatta gctacccaga aatggtgact    1140
ggattttct tcatcctgat gaccgtactg tggtttaccc gggagcctgg ctttgtccct    1200
ggctgggatt ctttctttga aaagaaaggc taccgtacta tgccacagt ctctgtcttc    1260
cttggcttcc tcctcttcct cattccagcg aagaagccct gctttgggaa aaagaatgat    1320
ggagagaacc aggagcactc actggggacc gagcccatca tcacgtggaa ggacttccag    1380
aagaccatgc cctgggagat tgtcattctg gttggggag gctatgctct ggcttctggt    1440
agcaagagct ctggcctctc tacatggatt gggaaccaga tgttgtccct gagcagcctc    1500
ccaccgtggg ctgtcacccct gctggcatgc atcctcgtgt ccattgtcac tgagtttgtg    1560
agcaacccag caaccatcac catcttcctg cccatcctgt gcagcctgtc tgaaacgcag    1620
cacattaacc ccctctacac cctgatccca gtcaccatgt gcatctcctt tgcagtgatg    1680
```

```
ctgcctgtgg gcaatccccc taatgccatc gtcttcagct atgggcactg ccagatcaaa    1740
gatatggtga agctggcct gggagtcaac gttattggac tggtgatagt aatggtggcc    1800
atcaacacct ggggagttag cctcttccac ctggacactt acccagcatg ggcgagggtc    1860
agcaacatca ctgatcaagc ctaa                                           1884
```

<210> SEQ ID NO 4
<211> LENGTH: 627
<212> TYPE: PRT
<213> ORGANISM: Homo sapiens

<400> SEQUENCE: 4

```
Met Gly Leu Leu Gln Gly Leu Leu Arg Val Arg Lys Leu Leu Leu Val
 1               5                  10                  15

Val Cys Val Pro Leu Leu Leu Pro Leu Pro Val Leu His Pro Ser
                20                  25                  30

Ser Glu Ala Ser Cys Ala Tyr Val Leu Ile Val Thr Ala Val Tyr Trp
            35                  40                  45

Val Ser Glu Ala Val Pro Leu Gly Ala Ala Ala Leu Val Pro Ala Phe
        50                  55                  60

Leu Tyr Pro Phe Phe Gly Val Leu Arg Ser Asn Glu Val Ala Ala Glu
 65                  70                  75                  80

Tyr Phe Lys Asn Thr Thr Leu Leu Val Gly Val Ile Cys Val Ala
                85                  90                  95

Ala Ala Val Glu Lys Trp Asn Leu His Lys Arg Ile Ala Leu Arg Met
            100                 105                 110

Val Leu Met Ala Gly Ala Lys Pro Gly Met Leu Leu Leu Cys Phe Met
        115                 120                 125

Cys Cys Thr Thr Leu Leu Ser Met Trp Leu Ser Asn Thr Ser Thr Thr
130                 135                 140

Ala Met Val Met Pro Ile Val Glu Ala Val Leu Gln Glu Leu Val Ser
145                 150                 155                 160

Ala Glu Asp Glu Gln Leu Val Ala Gly Asn Ser Asn Thr Glu Glu Ala
                165                 170                 175

Glu Pro Ile Ser Leu Asp Val Lys Asn Ser Gln Pro Ser Leu Glu Leu
            180                 185                 190

Ile Phe Val Asn Glu Asp Arg Ser Asn Ala Asp Leu Thr Thr Leu Met
        195                 200                 205

His Asn Glu Asn Leu Asn Gly Val Pro Ser Ile Thr Asn Pro Ile Lys
    210                 215                 220

Thr Ala Asn Gln His Gln Gly Lys Lys Gln His Pro Ser Gln Glu Lys
225                 230                 235                 240

Pro Gln Val Leu Thr Pro Ser Pro Arg Lys Gln Lys Leu Asn Arg Lys
                245                 250                 255

Tyr Arg Ser His His Asp Gln Met Ile Cys Lys Cys Leu Ser Leu Ser
            260                 265                 270

Ile Ser Tyr Ser Ala Thr Ile Gly Gly Leu Thr Thr Ile Ile Gly Thr
        275                 280                 285

Ser Thr Ser Leu Ile Phe Leu Glu His Phe Asn Asn Gln Tyr Pro Ala
    290                 295                 300

Ala Glu Val Val Asn Phe Gly Thr Trp Phe Leu Phe Ser Phe Pro Ile
305                 310                 315                 320

Ser Leu Ile Met Leu Val Val Ser Trp Phe Trp Met His Trp Leu Phe
                325                 330                 335
```

| | | | | | | | | | | | |
|---|---|---|---|---|---|---|---|---|---|---|---|
|Leu|Gly|Cys|Asn|Phe|Lys|Glu|Thr|Cys|Ser|Leu|Ser|Lys|Lys|Lys|Lys|
| | | |340| | | |345| | | |350| | | | |

Thr Lys Arg Glu Gln Leu Ser Glu Lys Arg Ile Gln Glu Glu Tyr Glu
            355                 360                 365

Lys Leu Gly Asp Ile Ser Tyr Pro Glu Met Val Thr Gly Phe Phe
    370                 375                 380

Ile Leu Met Thr Val Leu Trp Phe Thr Arg Glu Pro Gly Phe Val Pro
385                 390                 395                 400

Gly Trp Asp Ser Phe Phe Glu Lys Lys Gly Tyr Arg Thr Asp Ala Thr
                405                 410                 415

Val Ser Val Phe Leu Gly Phe Leu Phe Leu Ile Pro Ala Lys Lys
            420                 425                 430

Pro Cys Phe Gly Lys Lys Asn Asp Gly Glu Asn Gln Glu His Ser Leu
            435                 440                 445

Gly Thr Glu Pro Ile Ile Thr Trp Lys Asp Phe Gln Lys Thr Met Pro
    450                 455                 460

Trp Glu Ile Val Ile Leu Val Gly Gly Gly Tyr Ala Leu Ala Ser Gly
465                 470                 475                 480

Ser Lys Ser Ser Gly Leu Ser Thr Trp Ile Gly Asn Gln Met Leu Ser
                485                 490                 495

Leu Ser Ser Leu Pro Pro Trp Ala Val Thr Leu Leu Ala Cys Ile Leu
            500                 505                 510

Val Ser Ile Val Thr Glu Phe Val Ser Asn Pro Ala Thr Ile Thr Ile
            515                 520                 525

Phe Leu Pro Ile Leu Cys Ser Leu Ser Glu Thr Gln His Ile Asn Pro
            530                 535                 540

Leu Tyr Thr Leu Ile Pro Val Thr Met Cys Ile Ser Phe Ala Val Met
545                 550                 555                 560

Leu Pro Val Gly Asn Pro Pro Asn Ala Ile Val Phe Ser Tyr Gly His
                565                 570                 575

Cys Gln Ile Lys Asp Met Val Lys Ala Gly Leu Gly Val Asn Val Ile
            580                 585                 590

Gly Leu Val Ile Val Met Val Ala Ile Asn Thr Trp Gly Val Ser Leu
            595                 600                 605

Phe His Leu Asp Thr Tyr Pro Ala Trp Ala Arg Val Ser Asn Ile Thr
    610                 615                 620

Asp Gln Ala
625

<210> SEQ ID NO 5
<211> LENGTH: 1746
<212> TYPE: DNA
<213> ORGANISM: Homo sapiens

<400> SEQUENCE: 5

| | | |
|---|---|---|
|atgggcctgc tgcagggcct gctccgagtc cggaagctgc tgctggtcgt ctgcgtcccg|60|
|ctcctgctgc tgcctctgcc cgtcctccac cccagcagcg aggcctcgtg tgcttacgtg|120|
|ctgatcgtga ctgctgtgta ctgggtgtcg gaggcagtgc tctgggagc tgcagccctg|180|
|gtgccggcct tcctytaccc gttcttcgga gtcctccggt ccaatgaggt ggcggcggag|240|
|tacttcaaga caccacgctg ctgctggtg ggggtcatct gcgtggcggc tgccgtggag|300|
|aagtggaacc tgcataagcg cattgctctg cgcatggtct tgatggccgg rgccaagccg|360|
|ggcatgctgc tgctctgctt catgtgctgt accacgttgc tgtccatgtg gctgtccaac|420|

-continued

| | |
|---|---|
| acctccacca ccgccatggt gatgcccatc gtggaggccg tgctgcagga gctggtcagt | 480 |
| gctgaggacg agcagctcgt ggcgggcaac tccaacaccg aagaggccga acccatcagt | 540 |
| ctggatgtaa agaacagcca accttctctg gaactcatct ttgtcaatga agacaggtcc | 600 |
| aacgcagacc tcaccactct gatgcacaac gagaacctga atggtgtgcc ctcgatcacc | 660 |
| aacccatca aaactgcaaa ccaacaccag ggcaagaagc aacacccatc ccaggaaaag | 720 |
| ccacaagtcc tgacccccag ccccaggaag cagaagctga acagaaagta caggtcccac | 780 |
| catgaccaga tgatctgcaa gtgcctctcc ctgagcatat cctactccgc taccattggc | 840 |
| ggcctgacca ccatcatcgg cacctccacc agcctcatct tcctggaaca cttcaacaac | 900 |
| cagtatccag ccgcagaggt ggtgaacttt ggcacctggt tcctcttcag cttccccata | 960 |
| tccctcatca tgctggtggt cagctggttc tggatgcact ggctgttcct gggctgcaat | 1020 |
| tttaaagaga cctgctctct gagcaagaag aagaagacca aagggaaca gttgtcagag | 1080 |
| aagaggatcc aagaagaata tgaaaaactg ggagacatta gctacccaga aatggtgact | 1140 |
| ggatttttct tcatcctgat gaccgtactg tggtttaccc gggagcctgg ctttgtccct | 1200 |
| ggctgggatt ctttctttga aaagaaaggc taccgtactg atgccacagt ctctgtcttc | 1260 |
| cttggcttcc tcctcttcct cattccagcg aagaagccct gctttgggaa aagaatgat | 1320 |
| ggagagaacc aggagcactc actggggacc gagcccatca tcacgtggaa ggacttccag | 1380 |
| aagaccatgc cctgggagat tgtcattctg gttgggggag ctatgctct ggcttctggt | 1440 |
| agcaagagct ctggcctctc tacatggatt gggaaccaga tgttgtccct gagcagcctc | 1500 |
| ccaccgtggg ctgtcaccct gctggcatgc atcctcgtgt ccattgtcac tgagtttgtg | 1560 |
| agcaacccag caaccatcac catcttcctg cccatcctgt gcagcctggt gaaagctggc | 1620 |
| ctgggagtca acgttattgg actggtgata gtaatggtgg ccatcaacac ctggggagtt | 1680 |
| agcctcttcc acctggacac ttacccagca tgggcgaggg tcagcaacat cactgatcaa | 1740 |
| gcctaa | 1746 |

<210> SEQ ID NO 6
<211> LENGTH: 581
<212> TYPE: PRT
<213> ORGANISM: Homo sapiens

<400> SEQUENCE: 6

Met Gly Leu Leu Gln Gly Leu Leu Arg Val Arg Lys Leu Leu Leu Val
 1               5                  10                  15

Val Cys Val Pro Leu Leu Leu Pro Leu Pro Val Leu His Pro Ser
            20                  25                  30

Ser Glu Ala Ser Cys Ala Tyr Val Leu Ile Val Thr Ala Val Tyr Trp
        35                  40                  45

Val Ser Glu Ala Val Pro Leu Gly Ala Ala Ala Leu Val Pro Ala Phe
    50                  55                  60

Leu Tyr Pro Phe Phe Gly Val Leu Arg Ser Asn Glu Val Ala Ala Glu
65                  70                  75                  80

Tyr Phe Lys Asn Thr Thr Leu Leu Val Gly Val Ile Cys Val Ala
                85                  90                  95

Ala Ala Val Glu Lys Trp Asn Leu His Lys Arg Ile Ala Leu Arg Met
            100                 105                 110

Val Leu Met Ala Gly Ala Lys Pro Gly Met Leu Leu Leu Cys Phe Met
        115                 120                 125

Cys Cys Thr Thr Leu Leu Ser Met Trp Leu Ser Asn Thr Ser Thr Thr

-continued

```
            130                 135                 140
Ala Met Val Met Pro Ile Val Glu Ala Val Leu Gln Glu Leu Val Ser
145                 150                 155                 160
Ala Glu Asp Glu Gln Leu Val Ala Gly Asn Ser Asn Thr Glu Glu Ala
                165                 170                 175
Glu Pro Ile Ser Leu Asp Val Lys Asn Ser Gln Pro Ser Leu Glu Leu
            180                 185                 190
Ile Phe Val Asn Glu Asp Arg Ser Asn Ala Asp Leu Thr Thr Leu Met
                195                 200                 205
His Asn Glu Asn Leu Asn Gly Val Pro Ser Ile Thr Asn Pro Ile Lys
            210                 215                 220
Thr Ala Asn Gln His Gln Gly Lys Lys Gln His Pro Ser Gln Glu Lys
225                 230                 235                 240
Pro Gln Val Leu Thr Pro Ser Pro Arg Lys Gln Lys Leu Asn Arg Lys
                245                 250                 255
Tyr Arg Ser His His Asp Gln Met Ile Cys Lys Cys Leu Ser Leu Ser
            260                 265                 270
Ile Ser Tyr Ser Ala Thr Ile Gly Gly Leu Thr Thr Ile Ile Gly Thr
                275                 280                 285
Ser Thr Ser Leu Ile Phe Leu Glu His Phe Asn Asn Gln Tyr Pro Ala
290                 295                 300
Ala Glu Val Val Asn Phe Gly Thr Trp Phe Leu Phe Ser Phe Pro Ile
305                 310                 315                 320
Ser Leu Ile Met Leu Val Ser Trp Phe Trp Met His Trp Leu Phe
                325                 330                 335
Leu Gly Cys Asn Phe Lys Glu Thr Cys Ser Leu Ser Lys Lys Lys Lys
                340                 345                 350
Thr Lys Arg Glu Gln Leu Ser Glu Lys Arg Ile Gln Glu Glu Tyr Glu
                355                 360                 365
Lys Leu Gly Asp Ile Ser Tyr Pro Glu Met Val Thr Gly Phe Phe Phe
            370                 375                 380
Ile Leu Met Thr Val Leu Trp Phe Thr Arg Glu Pro Gly Phe Val Pro
385                 390                 395                 400
Gly Trp Asp Ser Phe Phe Glu Lys Lys Gly Tyr Arg Thr Asp Ala Thr
                405                 410                 415
Val Ser Val Phe Leu Gly Phe Leu Phe Leu Ile Pro Ala Lys Lys
                420                 425                 430
Pro Cys Phe Gly Lys Lys Asn Asp Gly Glu Asn Gln Glu His Ser Leu
            435                 440                 445
Gly Thr Glu Pro Ile Ile Thr Trp Lys Asp Phe Gln Lys Thr Met Pro
            450                 455                 460
Trp Glu Ile Val Ile Leu Val Gly Gly Tyr Ala Leu Ala Ser Gly
465                 470                 475                 480
Ser Lys Ser Ser Gly Leu Ser Thr Trp Ile Gly Asn Gln Met Leu Ser
                485                 490                 495
Leu Ser Ser Leu Pro Pro Trp Ala Val Thr Leu Leu Ala Cys Ile Leu
            500                 505                 510
Val Ser Ile Val Thr Glu Phe Val Ser Asn Pro Ala Thr Ile Thr Ile
            515                 520                 525
Phe Leu Pro Ile Leu Cys Ser Leu Val Lys Ala Gly Leu Gly Val Asn
            530                 535                 540
Val Ile Gly Leu Val Ile Val Met Val Ala Ile Asn Thr Trp Gly Val
545                 550                 555                 560
```

-continued

Ser Leu Phe His Leu Asp Thr Tyr Pro Ala Trp Ala Arg Val Ser Asn
            565                 570                 575
Ile Thr Asp Gln Ala
        580

<210> SEQ ID NO 7
<211> LENGTH: 1884
<212> TYPE: DNA
<213> ORGANISM: Homo sapiens

<400> SEQUENCE: 7

| | | | | | |
|---|---|---|---|---|---|
| atgggcctgc | tgcagggcct | gctccgagtc | cggaagctgc | tgctggtcgt | ctgcgtcccg | 60 |
| ctcctgctgc | tgcctctgcc | cgtcctccac | cccagcagcg | aggcctcgtg | tgcttacgtg | 120 |
| ctgatcgtga | ctgctgtgta | ctgggtgtcg | gaggcagtgc | tctgggagc | tgcagccctg | 180 |
| gtgccggcct | tcctytaccc | gttcttcgga | gtcctccggt | ccaatgaggt | ggcggcggag | 240 |
| tacttcaaga | caccacgct | gctgctggtg | ggggtcatct | gcgtggcggc | tgccgtggag | 300 |
| aagtggaacc | tgcataagcg | cattgctctg | cgcatggtct | tgatggccgg | rgccaagccg | 360 |
| ggcatgctgc | tgctctgctt | catgtgctgt | accacgttgc | tgtccatgtg | gctgtccaac | 420 |
| acctccacca | ccgccatggt | gatgcccatc | gtggaggccg | tgctgcagga | gctggtcagt | 480 |
| gctgaggacg | agcagctcgt | ggcgggcaac | tccaacaccg | aagaggccga | acccatcagt | 540 |
| ctggatgtaa | agaacagcca | accttctctg | gaactcatct | ttgtcaatga | agacaggtcc | 600 |
| aacgcagacc | tcaccactct | gatgcacaac | gagaacctga | atggtgtgcc | ctcgatcacc | 660 |
| aaccccatca | aaactgcaaa | ccaacaccag | ggcaagaagc | aacacccatc | ccaggaaaag | 720 |
| ccacaagtcc | tgaccccag | ccccaggaag | cagaagctga | acagaaagta | caggtcccac | 780 |
| catgaccaga | tgatctgcaa | gtgcctctcc | ctgagcatat | cctactccgc | taccattggc | 840 |
| ggcctgacca | ccatcatcgg | cacctccacc | agcctcatct | tcctggaaca | cttcaacaac | 900 |
| cagtatccag | ccgcagaggt | ggtgaacttt | ggcacctggt | tcctcttcag | cttccccata | 960 |
| tccctcatca | tgctggtggt | cagctggttc | tggatgcact | ggctgttcct | gggctgcaat | 1020 |
| tttaaagaga | cctgctctct | gagcaagaag | aagaagacca | aaagggaaca | gttgtcagag | 1080 |
| aagaggatcc | aagaagaata | tgaaaaactg | ggagacatta | gctacccaga | aatggtgact | 1140 |
| ggattttttct | tcatcctgat | gaccgtactg | tggtttaccc | gggagcctgg | ctttgtccct | 1200 |
| ggctgggatt | cttcctttga | aaagaaaggc | taccgtacta | tgccacagt | ctctgtcttc | 1260 |
| cttggcttcc | tcctcttcct | cattccagcg | aagaagccct | gctttgggaa | aagaatgat | 1320 |
| ggagagaacc | aggagcactc | actggggacc | gagtccatca | tcacgtggaa | ggacttccag | 1380 |
| aagaccatgc | cctgggagat | tgtcattctg | gttggggag | ctatgctct | ggcttctggt | 1440 |
| agcaagagct | ctggcctctc | tacatggatt | gggaaccaga | tgttgtccct | gagcagcctc | 1500 |
| ccaccgtggg | ctgtcaccct | gctggcatgc | atcctcgtgt | ccattgtcac | tgagtttgtg | 1560 |
| agcaacccag | caaccatcac | catcttcctg | cccatcctgt | gcagcctgtc | tgaaacgctg | 1620 |
| cacattaacc | ccctctacac | cctgatccca | gtcaccatgt | gcatctcctt | tgcagtgatg | 1680 |
| ctgcctgtgg | gcaatccccc | taatgccatc | gtcttcagct | atgggcactg | ccagatcaaa | 1740 |
| gatatggtga | agctggcct | gggagtcaac | gttattggac | tggtgatagt | aatggtggcc | 1800 |
| atcaacacct | ggggagttag | cctcttccac | ctggacactt | acccagcatg | ggcgagggtc | 1860 |
| agcaacatca | ctgatcaagc | ctaa | | | | 1884 |

-continued

```
<210> SEQ ID NO 8
<211> LENGTH: 627
<212> TYPE: PRT
<213> ORGANISM: Homo sapiens

<400> SEQUENCE: 8
```

| | | | | | | | | | | | | | | | |
|---|---|---|---|---|---|---|---|---|---|---|---|---|---|---|---|
| Met | Gly | Leu | Leu | Gln | Gly | Leu | Leu | Arg | Val | Arg | Lys | Leu | Leu | Leu | Val |
| 1 | | | | 5 | | | | | 10 | | | | | 15 | |
| Val | Cys | Val | Pro | Leu | Leu | Leu | Pro | Leu | Pro | Val | Leu | His | Pro | Ser | |
| | | | 20 | | | | | 25 | | | | | 30 | | |
| Ser | Glu | Ala | Ser | Cys | Ala | Tyr | Val | Leu | Ile | Val | Thr | Ala | Val | Tyr | Trp |
| | | 35 | | | | | 40 | | | | | 45 | | | |
| Val | Ser | Glu | Ala | Val | Pro | Leu | Gly | Ala | Ala | Ala | Leu | Val | Pro | Ala | Phe |
| | 50 | | | | | 55 | | | | | 60 | | | | |
| Leu | Tyr | Pro | Phe | Phe | Gly | Val | Leu | Arg | Ser | Asn | Glu | Val | Ala | Ala | Glu |
| 65 | | | | | 70 | | | | | 75 | | | | | 80 |
| Tyr | Phe | Lys | Asn | Thr | Thr | Leu | Leu | Val | Gly | Val | Ile | Cys | Val | Ala | |
| | | | | 85 | | | | | 90 | | | | | 95 | |
| Ala | Ala | Val | Glu | Lys | Trp | Asn | Leu | His | Lys | Arg | Ile | Ala | Leu | Arg | Met |
| | | | 100 | | | | | 105 | | | | | 110 | | |
| Val | Leu | Met | Ala | Gly | Ala | Lys | Pro | Gly | Met | Leu | Leu | Leu | Cys | Phe | Met |
| | | 115 | | | | | 120 | | | | | 125 | | | |
| Cys | Cys | Thr | Thr | Leu | Leu | Ser | Met | Trp | Leu | Ser | Asn | Thr | Ser | Thr | Thr |
| 130 | | | | | 135 | | | | | 140 | | | | | |
| Ala | Met | Val | Met | Pro | Ile | Val | Glu | Ala | Val | Leu | Gln | Glu | Leu | Val | Ser |
| 145 | | | | | 150 | | | | | 155 | | | | | 160 |
| Ala | Glu | Asp | Glu | Gln | Leu | Val | Ala | Gly | Asn | Ser | Asn | Thr | Glu | Glu | Ala |
| | | | | 165 | | | | | 170 | | | | | 175 | |
| Glu | Pro | Ile | Ser | Leu | Asp | Val | Lys | Asn | Ser | Gln | Pro | Ser | Leu | Glu | Leu |
| | | | 180 | | | | | 185 | | | | | 190 | | |
| Ile | Phe | Val | Asn | Glu | Asp | Arg | Ser | Asn | Ala | Asp | Leu | Thr | Thr | Leu | Met |
| | | | | 195 | | | | | 200 | | | | | 205 | |
| His | Asn | Glu | Asn | Leu | Asn | Gly | Val | Pro | Ser | Ile | Thr | Asn | Pro | Ile | Lys |
| | | 210 | | | | | 215 | | | | | 220 | | | |
| Thr | Ala | Asn | Gln | His | Gln | Gly | Lys | Lys | Gln | His | Pro | Ser | Gln | Glu | Lys |
| 225 | | | | | 230 | | | | | 235 | | | | | 240 |
| Pro | Gln | Val | Leu | Thr | Pro | Ser | Pro | Arg | Lys | Gln | Lys | Leu | Asn | Arg | Lys |
| | | | | 245 | | | | | 250 | | | | | 255 | |
| Tyr | Arg | Ser | His | His | Asp | Gln | Met | Ile | Cys | Lys | Cys | Leu | Ser | Leu | Ser |
| | | | 260 | | | | | 265 | | | | | 270 | | |
| Ile | Ser | Tyr | Ser | Ala | Thr | Ile | Gly | Gly | Leu | Thr | Thr | Ile | Ile | Gly | Thr |
| | | | 275 | | | | | 280 | | | | | 285 | | |
| Ser | Thr | Ser | Leu | Ile | Phe | Leu | Glu | His | Phe | Asn | Asn | Gln | Tyr | Pro | Ala |
| | | 290 | | | | | 295 | | | | | 300 | | | |
| Ala | Glu | Val | Val | Asn | Phe | Gly | Thr | Trp | Phe | Leu | Phe | Ser | Phe | Pro | Ile |
| 305 | | | | | 310 | | | | | 315 | | | | | 320 |
| Ser | Leu | Ile | Met | Leu | Val | Val | Ser | Trp | Phe | Trp | Met | His | Trp | Leu | Phe |
| | | | | 325 | | | | | 330 | | | | | 335 | |
| Leu | Gly | Cys | Asn | Phe | Lys | Glu | Thr | Cys | Ser | Leu | Ser | Lys | Lys | Lys | Lys |
| | | | 340 | | | | | 345 | | | | | 350 | | |
| Thr | Lys | Arg | Glu | Gln | Leu | Ser | Glu | Lys | Arg | Ile | Gln | Glu | Glu | Tyr | Glu |
| | | | | 355 | | | | | 360 | | | | | 365 | |
| Lys | Leu | Gly | Asp | Ile | Ser | Tyr | Pro | Glu | Met | Val | Thr | Gly | Phe | Phe | Phe |
| | | 370 | | | | | 375 | | | | | 380 | | | |

```
Ile Leu Met Thr Val Leu Trp Phe Thr Arg Glu Pro Gly Phe Val Pro
385                 390                 395                 400

Gly Trp Asp Ser Phe Phe Glu Lys Lys Gly Tyr Arg Thr Asp Ala Thr
                405                 410                 415

Val Ser Val Phe Leu Gly Phe Leu Leu Phe Leu Ile Pro Ala Lys Lys
                420                 425                 430

Pro Cys Phe Gly Lys Lys Asn Asp Gly Glu Asn Gln Glu His Ser Leu
                435                 440                 445

Gly Thr Glu Ser Ile Ile Thr Trp Lys Asp Phe Gln Lys Thr Met Pro
450                 455                 460

Trp Glu Ile Val Ile Leu Val Gly Gly Gly Tyr Ala Leu Ala Ser Gly
465                 470                 475                 480

Ser Lys Ser Ser Gly Leu Ser Thr Trp Ile Gly Asn Gln Met Leu Ser
                485                 490                 495

Leu Ser Ser Leu Pro Pro Trp Ala Val Thr Leu Leu Ala Cys Ile Leu
                500                 505                 510

Val Ser Ile Val Thr Glu Phe Val Ser Asn Pro Ala Thr Ile Thr Ile
                515                 520                 525

Phe Leu Pro Ile Leu Cys Ser Leu Ser Glu Thr Leu His Ile Asn Pro
530                 535                 540

Leu Tyr Thr Leu Ile Pro Val Thr Met Cys Ile Ser Phe Ala Val Met
545                 550                 555                 560

Leu Pro Val Gly Asn Pro Pro Asn Ala Ile Val Phe Ser Tyr Gly His
                565                 570                 575

Cys Gln Ile Lys Asp Met Val Lys Ala Gly Leu Gly Val Asn Val Ile
                580                 585                 590

Gly Leu Val Ile Val Met Val Ala Ile Asn Thr Trp Gly Val Ser Leu
                595                 600                 605

Phe His Leu Asp Thr Tyr Pro Ala Trp Ala Arg Val Ser Asn Ile Thr
610                 615                 620

Asp Gln Ala
625

<210> SEQ ID NO 9
<211> LENGTH: 1884
<212> TYPE: DNA
<213> ORGANISM: Homo sapiens

<400> SEQUENCE: 9
atgggcctgc tgcagggcct gctccgagtc cggaagctgc tgctggtcgt ctgcgtcccg      60
ctcctgctgc tgcctctgcc cgtcctccac cccagcagcg aggcctcgtg tgcttacgtg     120
ctgatcgtga ctgctgtgta ctgggtgtcg gaggcagtgc tctgggagc tgcagccctg     180 gtgccggcct tcctytaccc gttcttcgga gtcctccggt ccaatgaggt ggcggcggag     240
tacttcaaga caccacgct gctgctggtg ggggtcatct gcgtggcggc tgccgtggag     300
aagtggaacc tgcataagcg cattgctctg cgcatggtct tgatggccgg rgccaagccg     360
ggcatgctgc tgctctgctt catgtgctgt accacgttgc tgtccatgtg gctgtccaac     420
acctccacca ccgccatggt gatgcccatc gtggaggccg tgctgcagga gctggtcagt     480
gctgaggacg agcagctcgt ggcgggcaac tccaacaccg aagaggccga accatcagt      540 ctggatgtaa agaacagcca accttctctg gaactcatct ttgtcaatga agacaggtcc     600
aacgcagacc tcaccactct gatgcacaac gagaacctga tggtgtgcc ctcgatcacc     660
```

-continued

```
aaccccatca aaactgcaaa ccaacaccag ggcaagaagc aacacccatc ccaggaaaag      720
ccacaagtcc tgaccccag ccccaggaag cagaagctga acagaaagta caggtcccac       780
catgaccaga tgatctgcaa gtgcctctcc ctgagcatat cctactccgc taccattggc      840
ggcctgacca ccatcatcgg cacctccacc agcctcatct tcctggaaca cttcaacaac      900
cagtatccag ccgcagaggt ggtgaacttt ggcacctggt tcctcttcag cttccccata      960
tccctcatca tgctggtggt cagctggttc tggatgcact ggctgttcct gggctgcaat     1020
tttaaagaga cctgctctct gagcaagaag aagaagacca aagggaaca gttgtcagag      1080 aagaggatcc aagaagaata tgaaaaactg ggagacatta gctacccaga aatggtgact     1140 ggattttttct tcatcctgat gaccgtactg tggtttaccc gggagcctgg ctttgtccct    1200
ggctgggatt ctttctttga aagaaaggc taccgtactg atgccacagt tctgtcttc       1260 cttggcttcc tcctcttcct cattccagcg aagaagccct gctttgggaa aaagaatgat    1320
ggagagaacc aggagcactc actggggacc gagtccatca tcacgtggaa ggacttccag    1380
aagaccatgc cctgggagat tgtcattctg gttgggggag ctatgctctg gcttctggt     1440 agcaagagct ctggcctctc tacatggatt gggaaccaga tgttgtccct gagcagcctc    1500
ccaccgtggg ctgtcaccct gctggcatgc atcctcgtgt ccattgtcac tgagttgtg    1560 agcaacccag caaccatcac catcttcctg cccatcctgt gcagcctgtc tgaaacgcag    1620
cacattaacc ccctctacac cctgatccca gtcaccatgt gcatctcctt tgcagtgatg    1680
ctgcctgtgg gcaatccccc taatgccatc gtcttcagct atgggcactg ccagatcaaa    1740
gatatggtga agctggcct gggagtcaac gttattggac tggtgatagt aatggtggcc     1800
atcaacacct ggggagttag cctcttccac ctggacactt acccagcatg ggcgagggtc    1860
agcaacatca ctgatcaagc ctaa                                            1884
```

```
<210> SEQ ID NO 10
<211> LENGTH: 627
<212> TYPE: PRT
<213> ORGANISM: Homo sapiens

<400> SEQUENCE: 10

Met Gly Leu Leu Gln Gly Leu Leu Arg Val Arg Lys Leu Leu Leu Val
1               5                   10                  15

Val Cys Val Pro Leu Leu Leu Pro Leu Pro Val Leu His Pro Ser
                20                  25                  30

Ser Glu Ala Ser Cys Ala Tyr Val Leu Ile Val Thr Ala Val Tyr Trp
        35                  40                  45

Val Ser Glu Ala Val Pro Leu Gly Ala Ala Ala Leu Val Pro Ala Phe
    50                  55                  60

Leu Tyr Pro Phe Phe Gly Val Leu Arg Ser Asn Glu Val Ala Ala Glu
65                  70                  75                  80

Tyr Phe Lys Asn Thr Thr Leu Leu Val Gly Val Ile Cys Val Ala
                85                  90                  95

Ala Ala Val Glu Lys Trp Asn Leu His Lys Arg Ile Ala Leu Arg Met
                100                 105                 110

Val Leu Met Ala Gly Ala Lys Pro Gly Met Leu Leu Leu Cys Phe Met
            115                 120                 125

Cys Cys Thr Thr Leu Leu Ser Met Trp Leu Ser Asn Thr Ser Thr Thr
        130                 135                 140

Ala Met Val Met Pro Ile Val Glu Ala Val Leu Gln Glu Leu Val Ser
145                 150                 155                 160
```

-continued

```
Ala Glu Asp Glu Gln Leu Val Ala Gly Asn Ser Asn Thr Glu Glu Ala
            165                 170                 175
Glu Pro Ile Ser Leu Asp Val Lys Asn Ser Gln Pro Ser Leu Glu Leu
            180                 185                 190
Ile Phe Val Asn Glu Asp Arg Ser Asn Ala Asp Leu Thr Thr Leu Met
            195                 200                 205
His Asn Glu Asn Leu Asn Gly Val Pro Ser Ile Thr Asn Pro Ile Lys
            210                 215                 220
Thr Ala Asn Gln His Gln Gly Lys Lys Gln His Pro Ser Gln Glu Lys
225                 230                 235                 240
Pro Gln Val Leu Thr Pro Ser Pro Arg Lys Gln Lys Leu Asn Arg Lys
            245                 250                 255
Tyr Arg Ser His His Asp Gln Met Ile Cys Lys Cys Leu Ser Leu Ser
            260                 265                 270
Ile Ser Tyr Ser Ala Thr Ile Gly Gly Leu Thr Thr Ile Ile Gly Thr
            275                 280                 285
Ser Thr Ser Leu Ile Phe Leu Glu His Phe Asn Asn Gln Tyr Pro Ala
290                 295                 300
Ala Glu Val Val Asn Phe Gly Thr Trp Phe Leu Phe Ser Phe Pro Ile
305                 310                 315                 320
Ser Leu Ile Met Leu Val Val Ser Trp Phe Trp Met His Trp Leu Phe
            325                 330                 335
Leu Gly Cys Asn Phe Lys Glu Thr Cys Ser Leu Ser Lys Lys Lys
            340                 345                 350
Thr Lys Arg Glu Gln Leu Ser Glu Lys Arg Ile Gln Glu Glu Tyr Glu
            355                 360                 365
Lys Leu Gly Asp Ile Ser Tyr Pro Glu Met Val Thr Gly Phe Phe Phe
            370                 375                 380
Ile Leu Met Thr Val Leu Trp Phe Thr Arg Glu Pro Gly Phe Val Pro
385                 390                 395                 400
Gly Trp Asp Ser Phe Phe Glu Lys Lys Gly Tyr Arg Thr Asp Ala Thr
            405                 410                 415
Val Ser Val Phe Leu Gly Phe Leu Leu Phe Leu Ile Pro Ala Lys Lys
            420                 425                 430
Pro Cys Phe Gly Lys Lys Asn Asp Gly Glu Asn Gln Glu His Ser Leu
            435                 440                 445
Gly Thr Glu Ser Ile Ile Thr Trp Lys Asp Phe Gln Lys Thr Met Pro
            450                 455                 460
Trp Glu Ile Val Ile Leu Val Gly Gly Tyr Ala Leu Ala Ser Gly
465                 470                 475                 480
Ser Lys Ser Ser Gly Leu Ser Thr Trp Ile Gly Asn Gln Met Leu Ser
            485                 490                 495
Leu Ser Ser Leu Pro Pro Trp Ala Val Thr Leu Leu Ala Cys Ile Leu
            500                 505                 510
Val Ser Ile Val Thr Glu Phe Val Ser Asn Pro Ala Thr Ile Thr Ile
            515                 520                 525
Phe Leu Pro Ile Leu Cys Ser Leu Ser Glu Thr Gln His Ile Asn Pro
            530                 535                 540
Leu Tyr Thr Leu Ile Pro Val Thr Met Cys Ile Ser Phe Ala Val Met
545                 550                 555                 560
Leu Pro Val Gly Asn Pro Pro Asn Ala Ile Val Phe Ser Tyr Gly His
            565                 570                 575
```

-continued

```
Cys Gln Ile Lys Asp Met Val Lys Ala Gly Leu Gly Val Asn Val Ile
            580                 585                 590

Gly Leu Val Ile Val Met Val Ala Ile Asn Thr Trp Gly Val Ser Leu
        595                 600                 605

Phe His Leu Asp Thr Tyr Pro Ala Trp Ala Arg Val Ser Asn Ile Thr
    610                 615                 620

Asp Gln Ala
625

<210> SEQ ID NO 11
<211> LENGTH: 1746
<212> TYPE: DNA
<213> ORGANISM: Homo sapiens

<400> SEQUENCE: 11
atgggcctgc tgcagggcct gctccgagtc cggaagctgc tgctggtcgt ctgcgtcccg      60
ctcctgctgc tgcctctgcc cgtcctccac cccagcagcg aggcctcgtg tgcttacgtg     120
ctgatcgtga ctgctgtgta ctgggtgtcg gaggcagtgc tctgggagc tgcagccctg      180 gtgccggcct tcctytaccc gttcttcgga gtcctccggt ccaatgaggt ggcggcggag     240
tacttcaaga acaccacgct gctgctggtg ggggtcatct gcgtggcggc tgccgtggag     300
aagtggaacc tgcataagcg cattgctctg cgcatggtct gatgccgg rgccaagccg      360 ggcatgctgc tgctctgctt catgtgctgt accacgttgc tgtccatgtg gctgtccaac     420
acctccacca ccgccatggt gatgcccatc gtggaggccg ctgcagga gctggtcagt      480 gctgaggacg agcagctcgt ggcgggcaac tccaacaccg aagaggccga acccatcagt     540
ctggatgtaa agaacagcca accttctctg gaactcatct ttgtcaatga agacaggtcc     600
aacgcagacc tcaccactct gatgcacaac gagaacctga atggtgtgcc ctcgatcacc     660
aaccccatca aaactgcaaa ccaacaccag ggcaagaagc aacacccatc ccaggaaaag     720
ccacaagtcc tgacccccag cccaggaag cagaagctga acagaaagta caggtcccac      780
catgaccaga tgatctgcaa gtgcctctcc ctgagcatat cctactccgc taccattggc     840
ggcctgacca ccatcatcgg cacctccacc agcctcatct tcctggaaca cttcaacaac     900
cagtatccag ccgcagaggt ggtgaacttt ggcacctggt cctcttcag cttccccata      960 tccctcatca tgctggtggt cagctggttc tggatgcact ggctgttcct gggctgcaat    1020
tttaaagaga cctgctctct gagcaagaag aagaagacca aagggaaca gttgtcagag     1080 aagaggatcc aagaagaata tgaaaaactg ggagacatta gctacccaga aatggtgact    1140 ggattttct tcatcctgat gaccgtactg tggtttaccc gggagcctgg cttgtccct     1200 ggctgggatt ctttctttga aagaaaggc taccgtactg atgccacagt ctctgtcttc    1260
cttggcttcc tcctcttcct cattccagcg aagaagccct gctttgggaa aaagaatgat    1320
ggagagaacc aggagcactc actgggacc gagtccatca tcacgtggaa ggacttccag     1380
aagaccatgc cctgggagat tgtcattctg gttggggag ctatgctct ggcttctggt     1440 agcaagagct ctggcctctc tacatggatt gggaaccaga tgttgtccct gagcagcctc    1500
ccaccgtggg ctgtcaccct gctggcatgc atcctcgtgt ccattgtcac tgagtttgtg    1560
agcaacccag caaccatcac catcttcctg cccatcctgt gcagcctggt gaaagctggc    1620 ctggagtca cgttattgg actggtgata gtaatggtgg ccatcaacac ctggggagtt     1680
agcctcttcc acctggacac ttacccagca tgggcgaggg tcagcaacat cactgatcaa    1740
gcctaa                                                                1746
```

<210> SEQ ID NO 12
<211> LENGTH: 581
<212> TYPE: PRT
<213> ORGANISM: Homo sapiens

<400> SEQUENCE: 12

Met Gly Leu Leu Gln Gly Leu Leu Arg Val Arg Lys Leu Leu Val
1               5                   10                  15

Val Cys Val Pro Leu Leu Leu Pro Leu Pro Val Leu His Pro Ser
                20                  25                  30

Ser Glu Ala Ser Cys Ala Tyr Val Leu Ile Val Thr Ala Val Tyr Trp
            35                  40                  45

Val Ser Glu Ala Val Pro Leu Gly Ala Ala Ala Leu Val Pro Ala Phe
50                  55                  60

Leu Tyr Pro Phe Phe Gly Val Leu Arg Ser Asn Glu Val Ala Ala Glu
65                  70                  75                  80

Tyr Phe Lys Asn Thr Thr Leu Leu Val Gly Val Ile Cys Val Ala
                85                  90                  95

Ala Ala Val Glu Lys Trp Asn Leu His Lys Arg Ile Ala Leu Arg Met
                100                 105                 110

Val Leu Met Ala Gly Ala Lys Pro Gly Met Leu Leu Cys Phe Met
            115                 120                 125

Cys Cys Thr Thr Leu Leu Ser Met Trp Leu Ser Asn Thr Ser Thr Thr
130                 135                 140

Ala Met Val Met Pro Ile Val Glu Ala Val Leu Gln Glu Leu Val Ser
145                 150                 155                 160

Ala Glu Asp Glu Gln Leu Val Ala Gly Asn Ser Asn Thr Glu Glu Ala
                165                 170                 175

Glu Pro Ile Ser Leu Asp Val Lys Asn Ser Gln Pro Ser Leu Glu Leu
            180                 185                 190

Ile Phe Val Asn Glu Asp Arg Ser Asn Ala Asp Leu Thr Thr Leu Met
            195                 200                 205

His Asn Glu Asn Leu Asn Gly Val Pro Ser Ile Thr Asn Pro Ile Lys
210                 215                 220

Thr Ala Asn Gln His Gln Gly Lys Lys Gln His Pro Ser Gln Glu Lys
225                 230                 235                 240

Pro Gln Val Leu Thr Pro Ser Pro Arg Lys Gln Lys Leu Asn Arg Lys
                245                 250                 255

Tyr Arg Ser His His Asp Gln Met Ile Cys Lys Cys Leu Ser Leu Ser
            260                 265                 270

Ile Ser Tyr Ser Ala Thr Ile Gly Gly Leu Thr Thr Ile Ile Gly Thr
            275                 280                 285

Ser Thr Ser Leu Ile Phe Leu Glu His Phe Asn Asn Gln Tyr Pro Ala
        290                 295                 300

Ala Glu Val Val Asn Phe Gly Thr Trp Phe Leu Phe Ser Phe Pro Ile
305                 310                 315                 320

Ser Leu Ile Met Leu Val Val Ser Trp Phe Trp Met His Trp Leu Phe
                325                 330                 335

Leu Gly Cys Asn Phe Lys Glu Thr Cys Ser Leu Ser Lys Lys Lys
            340                 345                 350

Thr Lys Arg Glu Gln Leu Ser Glu Lys Arg Ile Gln Glu Glu Tyr Glu
        355                 360                 365

Lys Leu Gly Asp Ile Ser Tyr Pro Glu Met Val Thr Gly Phe Phe Phe

|     |     |     |     | 370 |     |     |     | 375 |     |     |     | 380 |     |     |
| --- | --- | --- | --- | --- | --- | --- | --- | --- | --- | --- | --- | --- | --- | --- |
| Ile | Leu | Met | Thr | Val | Leu | Trp | Phe | Thr | Arg | Glu | Pro | Gly | Phe | Val | Pro |
| 385 |     |     |     |     | 390 |     |     |     |     | 395 |     |     |     |     | 400 |
| Gly | Trp | Asp | Ser | Phe | Phe | Glu | Lys | Lys | Gly | Tyr | Arg | Thr | Asp | Ala | Thr |
|     |     |     |     | 405 |     |     |     |     | 410 |     |     |     |     | 415 |     |
| Val | Ser | Val | Phe | Leu | Gly | Phe | Leu | Leu | Phe | Leu | Ile | Pro | Ala | Lys | Lys |
|     |     |     |     | 420 |     |     |     |     | 425 |     |     |     |     | 430 |     |
| Pro | Cys | Phe | Gly | Lys | Lys | Asn | Asp | Gly | Glu | Asn | Gln | Glu | His | Ser | Leu |
|     |     |     |     | 435 |     |     |     |     | 440 |     |     |     |     | 445 |     |
| Gly | Thr | Glu | Ser | Ile | Ile | Thr | Trp | Lys | Asp | Phe | Gln | Lys | Thr | Met | Pro |
|     |     |     |     | 450 |     |     |     |     | 455 |     |     |     |     | 460 |     |
| Trp | Glu | Ile | Val | Ile | Leu | Val | Gly | Gly | Tyr | Ala | Leu | Ala | Ser | Gly |
| 465 |     |     |     |     | 470 |     |     |     |     | 475 |     |     |     |     | 480 |
| Ser | Lys | Ser | Ser | Gly | Leu | Ser | Thr | Trp | Ile | Gly | Asn | Gln | Met | Leu | Ser |
|     |     |     |     | 485 |     |     |     |     | 490 |     |     |     |     | 495 |     |
| Leu | Ser | Ser | Leu | Pro | Pro | Trp | Ala | Val | Thr | Leu | Leu | Ala | Cys | Ile | Leu |
|     |     |     |     | 500 |     |     |     |     | 505 |     |     |     |     | 510 |     |
| Val | Ser | Ile | Val | Thr | Glu | Phe | Val | Ser | Asn | Pro | Ala | Thr | Ile | Thr | Ile |
|     |     |     |     | 515 |     |     |     |     | 520 |     |     |     |     | 525 |     |
| Phe | Leu | Pro | Ile | Leu | Cys | Ser | Leu | Val | Lys | Ala | Gly | Leu | Gly | Val | Asn |
|     |     |     |     | 530 |     |     |     |     | 535 |     |     |     |     | 540 |     |
| Val | Ile | Gly | Leu | Val | Ile | Val | Met | Val | Ala | Ile | Asn | Thr | Trp | Gly | Val |
| 545 |     |     |     |     | 550 |     |     |     |     | 555 |     |     |     |     | 560 |
| Ser | Leu | Phe | His | Leu | Asp | Thr | Tyr | Pro | Ala | Trp | Ala | Arg | Val | Ser | Asn |
|     |     |     |     | 565 |     |     |     |     | 570 |     |     |     |     | 575 |     |
| Ile | Thr | Asp | Gln | Ala |
|     |     |     |     | 580 |

<210> SEQ ID NO 13
<211> LENGTH: 1881
<212> TYPE: DNA
<213> ORGANISM: Homo sapiens

<400> SEQUENCE: 13

```
atgggcctgc tgcagggcct gctccgagtc cggaagctgc tgctggtcgt ctgcgtcccg      60
ctcctgctgc tgcctctgcc cgtcctccac cccagcagcg aggcctcgtg tgcttacgtg     120
ctgatcgtga ctgctgtgta ctgggtgtcg gaggcagtgc ctctgggagc tgcagccctg     180
gtgccggcct tcctytaccc gttcttcgga gtcctccggt ccaatgaggt ggcggcggag     240
tacttcaaga caccacgct gctgctggtg ggggtcatct gcgtggcggc tgccgtggag     300
aagtggaacc tgcataagcg cattgctctg cgcatggtct tgatgccgg rgccaagccg     360
ggcatgctgc tgctctgctt catgtgctgt accacgttgc tgtccatgtg ctgtccaac     420
acctccacca ccgccatggt gatgcccatc gtggaggccg tgctgcagga gctggtcagt     480
gctgaggacg agcagctcgt ggcgggcaac tccaacaccg aagaggccga accatcagt     540
ctggatgtaa agaacagcca accttctctg gaactcatct ttgtcaatga agagtccaac     600
gcagacctca ccactctgat gcacaacgag aacctgaatg tgtgccctc gatcaccaac     660
cccatcaaaa ctgcaaacca acaccagggc aagaagcaac acccatccca ggaaaagcca     720
caagtcctga cccccagccc caggaagcag aagctgaaca gaaagtacag gtcccaccat     780
gaccagatga tctgcaagtg cctctccctg agcatatcct actccgctac cattggcggc     840
ctgaccacca tcatcggcac ctccaccagc ctcatcttcc tggaacactt caacaaccag     900
```

-continued

```
tatccagccg cagaggtggt gaactttggc acctggttcc tcttcagctt ccccatatcc     960
ctcatcatgc tggtggtcag ctggttctgg atgcactggc tgttcctggg ctgcaatttt    1020
aaagagacct gctctctgag caagaagaag aagaccaaaa gggaacagtt gtcagagaag    1080
aggatccaag aagaatatga aaaactggga gacattagct acccagaaat ggtgactgga    1140
tttttcttca tcctgatgac cgtactgtgg tttacccggg agcctggctt tgtccctggc    1200
tgggattctt tctttgaaaa gaaaggctac cgtactgatg ccacagtctc tgtcttcctt    1260
ggcttcctcc tcttcctcat tccagcgaag aagccctgct tgggaaaaaa gaatgatgga    1320
gagaaccagg agcactcact ggggaccgag cccatcatca cgtggaagga cttccagaag    1380
accatgccct gggagattgt cattctggtt gggggaggct atgctctggc ttctggtagc    1440
aagagctctg gcctctctac atggattggg aaccagatgt tgtccctgag cagcctccca    1500
ccgtgggctg tcaccctgct ggcatgcatc ctcgtgtcca ttgtcactga gtttgtgagc    1560
aacccagcaa ccatcaccat cttcctgccc atcctgtgca gcctgtctga aacgctgcac    1620
attaaccccc tctacaccct gatcccagtc accatgtgca tctcctttgc agtgatgctg    1680
cctgtgggca atccccctaa tgccatcgtc ttcagctatg gcactgcca  gatcaaagat    1740 atggtgaaag ctggcctggg agtcaacgtt attggactgg tgatagtaat ggtggccatc    1800
aacacctggg gagttagcct cttccacctg gacacttacc agcatgggc  gagggtcagc    1860 aacatcactg atcaagccta a                                              1881
```

<210> SEQ ID NO 14
<211> LENGTH: 626
<212> TYPE: PRT
<213> ORGANISM: Homo sapiens

<400> SEQUENCE: 14

```
Met Gly Leu Leu Gln Gly Leu Leu Arg Val Arg Lys Leu Leu Leu Val
 1               5                  10                  15

Val Cys Val Pro Leu Leu Leu Pro Leu Pro Val Leu His Pro Ser
            20                  25                  30

Ser Glu Ala Ser Cys Ala Tyr Val Leu Ile Val Thr Ala Val Tyr Trp
        35                  40                  45

Val Ser Glu Ala Val Pro Leu Gly Ala Ala Ala Leu Val Pro Ala Phe
    50                  55                  60

Leu Tyr Pro Phe Phe Gly Val Leu Arg Ser Asn Glu Val Ala Ala Glu
65                  70                  75                  80

Tyr Phe Lys Asn Thr Thr Leu Leu Val Gly Val Ile Cys Val Ala
                85                  90                  95

Ala Ala Val Glu Lys Trp Asn Leu His Lys Arg Ile Ala Leu Arg Met
            100                 105                 110

Val Leu Met Ala Gly Ala Lys Pro Gly Met Leu Leu Cys Phe Met
        115                 120                 125

Cys Cys Thr Thr Leu Leu Ser Met Trp Leu Ser Asn Thr Ser Thr Thr
    130                 135                 140

Ala Met Val Met Pro Ile Val Glu Ala Val Leu Gln Glu Leu Val Ser
145                 150                 155                 160

Ala Glu Asp Glu Gln Leu Val Ala Gly Asn Ser Asn Thr Glu Glu Ala
                165                 170                 175

Glu Pro Ile Ser Leu Asp Val Lys Asn Ser Gln Pro Ser Leu Glu Leu
            180                 185                 190

Ile Phe Val Asn Glu Glu Ser Asn Ala Asp Leu Thr Thr Leu Met His
```

```
                195                 200                 205
Asn Glu Asn Leu Asn Gly Val Pro Ser Ile Thr Asn Pro Ile Lys Thr
    210                 215                 220

Ala Asn Gln His Gln Gly Lys Lys Gln His Pro Ser Gln Glu Lys Pro
225                 230                 235                 240

Gln Val Leu Thr Pro Ser Pro Arg Lys Gln Lys Leu Asn Arg Lys Tyr
                245                 250                 255

Arg Ser His His Asp Gln Met Ile Cys Lys Cys Leu Ser Leu Ser Ile
                260                 265                 270

Ser Tyr Ser Ala Thr Ile Gly Gly Leu Thr Thr Ile Ile Gly Thr Ser
            275                 280                 285

Thr Ser Leu Ile Phe Leu Glu His Phe Asn Asn Gln Tyr Pro Ala Ala
        290                 295                 300

Glu Val Val Asn Phe Gly Thr Trp Phe Leu Phe Ser Phe Pro Ile Ser
305                 310                 315                 320

Leu Ile Met Leu Val Val Ser Trp Phe Trp Met His Trp Leu Phe Leu
                325                 330                 335

Gly Cys Asn Phe Lys Glu Thr Cys Ser Leu Ser Lys Lys Lys Lys Thr
                340                 345                 350

Lys Arg Glu Gln Leu Ser Glu Lys Arg Ile Gln Glu Glu Tyr Glu Lys
            355                 360                 365

Leu Gly Asp Ile Ser Tyr Pro Glu Met Val Thr Gly Phe Phe Phe Ile
        370                 375                 380

Leu Met Thr Val Leu Trp Phe Thr Arg Glu Pro Gly Phe Val Pro Gly
385                 390                 395                 400

Trp Asp Ser Phe Phe Glu Lys Lys Gly Tyr Arg Thr Asp Ala Thr Val
                405                 410                 415

Ser Val Phe Leu Gly Phe Leu Leu Phe Leu Ile Pro Ala Lys Lys Pro
                420                 425                 430

Cys Phe Gly Lys Lys Asn Asp Gly Glu Asn Gln Glu His Ser Leu Gly
                435                 440                 445

Thr Glu Pro Ile Ile Thr Trp Lys Asp Phe Gln Lys Thr Met Pro Trp
    450                 455                 460

Glu Ile Val Ile Leu Val Gly Gly Gly Tyr Ala Leu Ala Ser Gly Ser
465                 470                 475                 480

Lys Ser Ser Gly Leu Ser Thr Trp Ile Gly Asn Gln Met Leu Ser Leu
                485                 490                 495

Ser Ser Leu Pro Pro Trp Ala Val Thr Leu Leu Ala Cys Ile Leu Val
                500                 505                 510

Ser Ile Val Thr Glu Phe Val Ser Asn Pro Ala Thr Ile Thr Ile Phe
            515                 520                 525

Leu Pro Ile Leu Cys Ser Leu Ser Glu Thr Leu His Ile Asn Pro Leu
        530                 535                 540

Tyr Thr Leu Ile Pro Val Thr Met Cys Ile Ser Phe Ala Val Met Leu
545                 550                 555                 560

Pro Val Gly Asn Pro Pro Asn Ala Ile Val Phe Ser Tyr Gly His Cys
                565                 570                 575

Gln Ile Lys Asp Met Val Lys Ala Gly Leu Gly Val Asn Val Ile Gly
                580                 585                 590

Leu Val Ile Val Met Val Ala Ile Asn Thr Trp Gly Val Ser Leu Phe
            595                 600                 605

His Leu Asp Thr Tyr Pro Ala Trp Ala Arg Val Ser Asn Ile Thr Asp
    610                 615                 620
```

Gln Ala
625

<210> SEQ ID NO 15
<211> LENGTH: 1881
<212> TYPE: DNA
<213> ORGANISM: Homo sapiens

<400> SEQUENCE: 15

| | | | | | |
|---|---|---|---|---|---|
| atgggcctgc | tgcagggcct | gctccgagtc | cggaagctgc | tgctggtcgt | ctgcgtcccg | 60 |
| ctcctgctgc | tgcctctgcc | cgtcctccac | cccagcagcg | aggcctcgtg | tgcttacgtg | 120 |
| ctgatcgtga | ctgctgtgta | ctgggtgtcg | gaggcagtgc | ctctgggagc | tgcagccctg | 180 |
| gtgccggcct | tcctytaccc | gttcttcgga | gtcctccggt | ccaatgaggt | ggcggcggag | 240 |
| tacttcaaga | acaccacgct | gctgctggtg | ggggtcatct | gcgtggcggc | tgccgtggag | 300 |
| aagtggaacc | tgcataagcg | cattgctctg | cgcatggtct | tgatggccgg | rgccaagccg | 360 |
| ggcatgctgc | tgctctgctt | catgtgctgt | accacgttgc | tgtccatgtg | gctgtccaac | 420 |
| acctccacca | ccgccatggt | gatgcccatc | gtggaggccg | tgctgcagga | gctggtcagt | 480 |
| gctgaggacg | agcagctcgt | ggcgggcaac | tccaacaccg | aagaggccga | acccatcagt | 540 |
| ctggatgtaa | agaacagcca | accttctctg | gaactcatct | ttgtcaatga | agagtccaac | 600 |
| gcagacctca | ccactctgat | gcacaacgag | aacctgaatg | tgtgccctc | gatcaccaac | 660 |
| cccatcaaaa | ctgcaaacca | acaccagggc | aagaagcaac | acccatccca | ggaaaagcca | 720 |
| caagtcctga | cccccagccc | caggaagcag | aagctgaaca | gaaagtacag | gtcccaccat | 780 |
| gaccagatga | tctgcaagtg | cctctcccta | agcatatcct | actccgctac | cattggcggc | 840 |
| ctgaccacca | tcatcggcac | ctccaccagc | ctcatcttcc | tggaacactt | caacaaccag | 900 |
| tatccagccg | cagaggtggt | gaactttggc | acctggttcc | tcttcagctt | ccccatatcc | 960 |
| ctcatcatgc | tggtggtcag | ctggttctgg | atgcactggc | tgttcctggg | ctgcaatttt | 1020 |
| aaagagacct | gctctctgag | caagaagaag | aagaccaaaa | gggaacagtt | gtcagagaag | 1080 |
| aggatccaag | aagaatatga | aaaactggga | gacattagct | acccagaaat | ggtgactgga | 1140 |
| tttttcttca | tcctgatgac | cgtactgtgg | tttacccggg | agcctggctt | tgtccctggc | 1200 |
| tgggattctt | tctttgaaaa | gaaaggctac | cgtactgatg | ccacagtctc | tgtcttcctt | 1260 |
| ggcttcctcc | tcttcctcat | tccagcgaag | aagcccctgc | ttgggaaaaa | gaatgatgga | 1320 |
| gagaaccagg | agcactcact | ggggaccgag | cccatcatca | cgtggaagga | cttccagaag | 1380 |
| accatgccct | gggagattgt | cattctggtt | gggggaggct | atgctctggc | ttctggtagc | 1440 |
| aagagctctg | gcctctctac | atggattggg | aaccagatgt | tgtccctgag | cagcctccca | 1500 |
| ccgtgggctg | tcaccctgct | ggcatgcatc | ctcgtgtcca | ttgtcactga | gtttgtgagc | 1560 |
| aacccagcaa | ccatcaccat | cttcctgccc | atcctgtgca | gcctgtctga | aacgcagcac | 1620 |
| attaaccccc | tctacaccct | gatcccagtc | accatgtgca | tctcctttgc | agtgatgctg | 1680 |
| cctgtgggca | atcccoctaa | tgccatcgtc | ttcagctatg | ggcactgcca | gatcaaagat | 1740 |
| atggtgaaag | ctggcctggg | agtcaacgtt | attggactgg | tgatagtaat | ggtggccatc | 1800 |
| aacacctggg | gagttagcct | cttccacctg | gacacttacc | cagcatgggc | gagggtcagc | 1860 |
| aacatcactg | atcaagccta | a | | | | 1881 |

<210> SEQ ID NO 16
<211> LENGTH: 626

```
<212> TYPE: PRT
<213> ORGANISM: Homo sapiens

<400> SEQUENCE: 16

Met Gly Leu Leu Gln Gly Leu Leu Arg Val Arg Lys Leu Leu Leu Val
  1               5                  10                  15

Val Cys Val Pro Leu Leu Leu Pro Leu Pro Val Leu His Pro Ser
             20                  25                  30

Ser Glu Ala Ser Cys Ala Tyr Val Leu Ile Val Thr Ala Val Tyr Trp
             35                  40                  45

Val Ser Glu Ala Val Pro Leu Gly Ala Ala Leu Val Pro Ala Phe
 50                  55                  60

Leu Tyr Pro Phe Phe Gly Val Leu Arg Ser Asn Glu Val Ala Ala Glu
 65                  70                  75                  80

Tyr Phe Lys Asn Thr Thr Leu Leu Val Gly Val Ile Cys Val Ala
             85                  90                  95

Ala Ala Val Glu Lys Trp Asn Leu His Lys Arg Ile Ala Leu Arg Met
            100                 105                 110

Val Leu Met Ala Gly Ala Lys Pro Gly Met Leu Leu Leu Cys Phe Met
            115                 120                 125

Cys Cys Thr Thr Leu Leu Ser Met Trp Leu Ser Asn Thr Ser Thr Thr
130                 135                 140

Ala Met Val Met Pro Ile Val Glu Ala Val Leu Gln Glu Leu Val Ser
145                 150                 155                 160

Ala Glu Asp Glu Gln Leu Val Ala Gly Asn Ser Asn Thr Glu Glu Ala
                165                 170                 175

Glu Pro Ile Ser Leu Asp Val Lys Asn Ser Gln Pro Ser Leu Glu Leu
            180                 185                 190

Ile Phe Val Asn Glu Glu Ser Asn Ala Asp Leu Thr Thr Leu Met His
            195                 200                 205

Asn Glu Asn Leu Asn Gly Val Pro Ser Ile Thr Asn Pro Ile Lys Thr
210                 215                 220

Ala Asn Gln His Gln Gly Lys Lys Gln His Pro Ser Gln Glu Lys Pro
225                 230                 235                 240

Gln Val Leu Thr Pro Ser Pro Arg Lys Gln Lys Leu Asn Arg Lys Tyr
                245                 250                 255

Arg Ser His His Asp Gln Met Ile Cys Lys Cys Leu Ser Leu Ser Ile
            260                 265                 270

Ser Tyr Ser Ala Thr Ile Gly Gly Leu Thr Thr Ile Gly Thr Ser
            275                 280                 285

Thr Ser Leu Ile Phe Leu Glu His Phe Asn Asn Gln Tyr Pro Ala Ala
        290                 295                 300

Glu Val Val Asn Phe Gly Thr Trp Phe Leu Phe Ser Phe Pro Ile Ser
305                 310                 315                 320

Leu Ile Met Leu Val Val Ser Trp Phe Trp Met His Trp Leu Phe Leu
                325                 330                 335

Gly Cys Asn Phe Lys Glu Thr Cys Ser Leu Ser Lys Lys Lys Lys Thr
            340                 345                 350

Lys Arg Glu Gln Leu Ser Glu Lys Arg Ile Gln Glu Glu Tyr Glu Lys
        355                 360                 365

Leu Gly Asp Ile Ser Tyr Pro Glu Met Val Thr Gly Phe Phe Phe Ile
    370                 375                 380

Leu Met Thr Val Leu Trp Phe Thr Arg Glu Pro Gly Phe Val Pro Gly
385                 390                 395                 400
```

Trp Asp Ser Phe Phe Glu Lys Lys Gly Tyr Arg Thr Asp Ala Thr Val
                405                 410                 415
Ser Val Phe Leu Gly Phe Leu Leu Phe Leu Ile Pro Ala Lys Lys Pro
            420                 425                 430
Cys Phe Gly Lys Lys Asn Asp Gly Glu Asn Gln Glu His Ser Leu Gly
        435                 440                 445
Thr Glu Pro Ile Ile Thr Trp Lys Asp Phe Gln Lys Thr Met Pro Trp
    450                 455                 460
Glu Ile Val Ile Leu Val Gly Gly Tyr Ala Leu Ala Ser Gly Ser
465                 470                 475                 480
Lys Ser Ser Gly Leu Ser Thr Trp Ile Gly Asn Gln Met Leu Ser Leu
                485                 490                 495
Ser Ser Leu Pro Pro Trp Ala Val Thr Leu Leu Ala Cys Ile Leu Val
            500                 505                 510
Ser Ile Val Thr Glu Phe Val Ser Asn Pro Ala Thr Ile Thr Ile Phe
        515                 520                 525
Leu Pro Ile Leu Cys Ser Leu Ser Glu Thr Gln His Ile Asn Pro Leu
    530                 535                 540
Tyr Thr Leu Ile Pro Val Thr Met Cys Ile Ser Phe Ala Val Met Leu
545                 550                 555                 560
Pro Val Gly Asn Pro Pro Asn Ala Ile Val Phe Ser Tyr Gly His Cys
                565                 570                 575
Gln Ile Lys Asp Met Val Lys Ala Gly Leu Gly Val Asn Val Ile Gly
            580                 585                 590
Leu Val Ile Val Met Val Ala Ile Asn Thr Trp Gly Val Ser Leu Phe
        595                 600                 605
His Leu Asp Thr Tyr Pro Ala Trp Ala Arg Val Ser Asn Ile Thr Asp
    610                 615                 620
Gln Ala
625

<210> SEQ ID NO 17
<211> LENGTH: 1743
<212> TYPE: DNA
<213> ORGANISM: Homo sapiens

<400> SEQUENCE: 17
atgggcctgc tgcagggcct gctccgagtc cggaagctgc tgctggtcgt ctgcgtcccg      60
ctcctgctgc tgcctctgcc cgtcctccac cccagcagcg aggcctcgtg tgcttacgtg     120
ctgatcgtga ctgctgtgta ctgggtgtcg gaggcagtgc tctgggagc tgcagccctg     180 gtgccggcct tcctytaccc gttcttcgga gtcctccggt ccaatgaggt ggcggcggag     240
tacttcaaga acaccacgct gctgctggtg ggggtcatct gcgtggcggc tgccgtggag     300
aagtggaacc tgcataagcg cattgctctg cgcatggtct tgatggccgg rgccaagccg     360
ggcatgctgc tgctctgctt catgtgctgt accacgttgc tgtccatgtg gctgtccaac     420
acctccacca ccgccatggt gatgcccatc gtggaggccg tgctgcagga gctggtcagt     480
gctgaggacg agcagctcgt ggcgggcaac tccaacaccg aagaggccga acccatcagt     540
ctggatgtaa agaacagcca accttctctg gaactcatct ttgtcaatga agagtccaac     600
gcagacctca ccactctgat gcacaacgag aacctgaatg gtgtgccctc gatcaccaac     660
cccatcaaaa ctgcaaacca acaccagggc aagaagcaac acccatccca ggaaaagcca     720
caagtcctga cccccagccc caggaagcag aagctgaaca gaaagtacag gtcccaccat     780

-continued

```
gaccagatga tctgcaagtg cctctccctg agcatatcct actccgctac cattggcggc      840
ctgaccacca tcatcggcac ctccaccagc ctcatcttcc tggaacactt caacaaccag      900
tatccagccg cagaggtggt gaactttggc acctggttcc tcttcagctt ccccatatcc      960
ctcatcatgc tggtggtcag ctggttctgg atgcactggc tgttcctggg ctgcaattt     1020 aaagagacct gctctctgag caagaagaag aagaccaaaa gggaacagtt gtcagagaag     1080
aggatccaag aagaatatga aaaactggga gacattagct acccagaaat ggtgactgga     1140
tttttcttca tcctgatgac cgtactgtgg tttacccggg agcctggctt tgtccctggc     1200
tgggattctt tctttgaaaa gaaaggctac cgtactgatg ccacagtctc tgtcttcctt     1260
ggcttcctcc tcttcctcat tccagcgaag aagccctgct tgggaaaaa gaatgatgga     1320 gagaaccagg agcactcact ggggaccgag cccatcatca cgtggaagga cttccagaag     1380
accatgccct gggagattgt cattctggtt gggggaggc atgctctggc ttctggtagc     1440
aagagctctg gcctctctac atggattggg aaccagatgt tgtccctgag cagcctccca     1500
ccgtgggctg tcaccctgct ggcatgcatc ctcgtgtcca ttgtcactga gtttgtgagc     1560
aacccagcaa ccatcaccat cttcctgccc atcctgtgca gcctggtgaa agctggcctg     1620
ggagtcaacg ttattggact ggtgatagta atggtggcca tcaacacctg ggagttagc     1680 ctcttccacc tggacactta cccagcatgg gcgagggtca gcaacatcac tgatcaagcc     1740
taa                                                                  1743
```

<210> SEQ ID NO 18
<211> LENGTH: 580
<212> TYPE: PRT
<213> ORGANISM: Homo sapiens

<400> SEQUENCE: 18

```
Met Gly Leu Leu Gln Gly Leu Leu Arg Val Arg Lys Leu Leu Leu Val
  1               5                  10                  15

Val Cys Val Pro Leu Leu Leu Pro Leu Pro Val Leu His Pro Ser
                 20                  25                  30

Ser Glu Ala Ser Cys Ala Tyr Val Leu Ile Val Thr Ala Val Tyr Trp
             35                  40                  45

Val Ser Glu Ala Val Pro Leu Gly Ala Ala Ala Leu Val Pro Ala Phe
         50                  55                  60

Leu Tyr Pro Phe Phe Gly Val Leu Arg Ser Asn Glu Val Ala Ala Glu
 65                  70                  75                  80

Tyr Phe Lys Asn Thr Thr Leu Leu Leu Val Gly Val Ile Cys Val Ala
                 85                  90                  95

Ala Ala Val Glu Lys Trp Asn Leu His Lys Arg Ile Ala Leu Arg Met
            100                 105                 110

Val Leu Met Ala Gly Ala Lys Pro Gly Met Leu Leu Leu Cys Phe Met
        115                 120                 125

Cys Cys Thr Thr Leu Leu Ser Met Trp Leu Ser Asn Thr Ser Thr Thr
    130                 135                 140

Ala Met Val Met Pro Ile Val Glu Ala Val Leu Gln Glu Leu Val Ser
145                 150                 155                 160

Ala Glu Asp Glu Gln Leu Val Ala Gly Asn Ser Asn Thr Glu Glu Ala
                165                 170                 175

Glu Pro Ile Ser Leu Asp Val Lys Asn Ser Gln Pro Ser Leu Glu Leu
            180                 185                 190
```

-continued

```
Ile Phe Val Asn Glu Glu Ser Asn Ala Asp Leu Thr Thr Leu Met His
            195                 200                 205

Asn Glu Asn Leu Asn Gly Val Pro Ser Ile Thr Asn Pro Ile Lys Thr
        210                 215                 220

Ala Asn Gln His Gln Gly Lys Lys Gln His Pro Ser Gln Glu Lys Pro
225                 230                 235                 240

Gln Val Leu Thr Pro Ser Pro Arg Lys Gln Lys Leu Asn Arg Lys Tyr
                245                 250                 255

Arg Ser His His Asp Gln Met Ile Cys Lys Cys Leu Ser Leu Ser Ile
            260                 265                 270

Ser Tyr Ser Ala Thr Ile Gly Gly Leu Thr Thr Ile Ile Gly Thr Ser
        275                 280                 285

Thr Ser Leu Ile Phe Leu Glu His Phe Asn Asn Gln Tyr Pro Ala Ala
        290                 295                 300

Glu Val Val Asn Phe Gly Thr Trp Phe Leu Phe Ser Phe Pro Ile Ser
305                 310                 315                 320

Leu Ile Met Leu Val Val Ser Trp Phe Trp Met His Trp Leu Phe Leu
                325                 330                 335

Gly Cys Asn Phe Lys Glu Thr Cys Ser Leu Ser Lys Lys Lys Lys Thr
            340                 345                 350

Lys Arg Glu Gln Leu Ser Glu Lys Arg Ile Gln Glu Glu Tyr Glu Lys
        355                 360                 365

Leu Gly Asp Ile Ser Tyr Pro Glu Met Val Thr Gly Phe Phe Phe Ile
        370                 375                 380

Leu Met Thr Val Leu Trp Phe Thr Arg Glu Pro Gly Phe Val Pro Gly
385                 390                 395                 400

Trp Asp Ser Phe Phe Glu Lys Lys Gly Tyr Arg Thr Asp Ala Thr Val
                405                 410                 415

Ser Val Phe Leu Gly Phe Leu Leu Phe Leu Ile Pro Ala Lys Lys Pro
            420                 425                 430

Cys Phe Gly Lys Lys Asn Asp Gly Glu Asn Gln Glu His Ser Leu Gly
        435                 440                 445

Thr Glu Pro Ile Ile Thr Trp Lys Asp Phe Gln Lys Thr Met Pro Trp
        450                 455                 460

Glu Ile Val Ile Leu Val Gly Gly Tyr Ala Leu Ala Ser Gly Ser
465                 470                 475                 480

Lys Ser Ser Gly Leu Ser Thr Trp Ile Gly Asn Gln Met Leu Ser Leu
                485                 490                 495

Ser Ser Leu Pro Pro Trp Ala Val Thr Leu Leu Ala Cys Ile Leu Val
            500                 505                 510

Ser Ile Val Thr Glu Phe Val Ser Asn Pro Ala Thr Ile Thr Ile Phe
        515                 520                 525

Leu Pro Ile Leu Cys Ser Leu Val Lys Ala Gly Leu Gly Val Asn Val
        530                 535                 540

Ile Gly Leu Val Ile Val Met Val Ala Ile Asn Thr Trp Gly Val Ser
545                 550                 555                 560

Leu Phe His Leu Asp Thr Tyr Pro Ala Trp Ala Arg Val Ser Asn Ile
                565                 570                 575

Thr Asp Gln Ala
            580

<210> SEQ ID NO 19
<211> LENGTH: 1881
<212> TYPE: DNA
```

<213> ORGANISM: Homo sapiens

<400> SEQUENCE: 19

| | |
|---|---|
| atgggcctgc tgcagggcct gctccgagtc cggaagctgc tgctggtcgt ctgcgtcccg | 60 |
| ctcctgctgc tgcctctgcc cgtcctccac cccagcagcg aggcctcgtg tgcttacgtg | 120 |
| ctgatcgtga ctgctgtgta ctgggtgtcg gaggcagtgc tctgggagc tgcagccctg | 180 |
| gtgccggcct tcctytaccc gttcttcgga gtcctccggt ccaatgaggt ggcggcggag | 240 |
| tacttcaaga caccacgct gctgctggtg ggggtcatct gcgtggcggc tgccgtggag | 300 |
| aagtggaacc tgcataagcg cattgctctg cgcatggtct tgatggccgg rgccaagccg | 360 |
| ggcatgctgc tgctctgctt catgtgctgt accacgttgc tgtccatgtg gctgtccaac | 420 |
| acctccacca ccgccatggt gatgcccatc gtggaggccg tgctgcagga gctggtcagt | 480 |
| gctgaggacg agcagctcgt ggcgggcaac tccaacaccg aagaggccga acccatcagt | 540 |
| ctggatgtaa agaacagcca accttctctg gaactcatct ttgtcaatga agagtccaac | 600 |
| gcagacctca ccactctgat gcacaacgag aacctgaatg tgtgcccctc gatcaccaac | 660 |
| cccatcaaaa ctgcaaacca acaccagggc aagaagcaac acccatccca ggaaaagcca | 720 |
| caagtcctga cccccagccc caggaagcag aagctgaaca gaaagtacag gtcccaccat | 780 |
| gaccagatga tctgcaagtg cctctcctg agcatatcct actccgctac cattggcggc | 840 |
| ctgaccacca tcatcggcac ctccaccagc ctcatcttcc tggaacactt caacaaccag | 900 |
| tatccagccg cagaggtggt gaactttggc acctggttcc tcttcagctt ccccatatcc | 960 |
| ctcatcatgc tggtggtcag ctggttctgg atgcactggc tgttcctggg ctgcaatttt | 1020 |
| aaagagacct gctctctgag caagaagaag aagaccaaaa gggaacagtt gtcagagaag | 1080 |
| aggatccaag aagaatatga aaaactggga gacattagct acccagaaat ggtgactgga | 1140 |
| ttttcttca tcctgatgac cgtactgtgg tttacccggg agcctggctt tgtccctggc | 1200 |
| tgggattctt tctttgaaaa gaaaggctac cgtactgatg ccacagtctc tgtcttcctt | 1260 |
| ggcttcctcc tcttcctcat tccagcgaag aagccctgct tgggaaaaa gaatgatgga | 1320 |
| gagaaccagg agcactcact ggggaccgag tccatcatca cgtggaagga cttccagaag | 1380 |
| accatgccct gggagattgt cattctggtt ggggaggct atgctctggc ttctggtagc | 1440 |
| aagagctctg gcctctctac atggattggg aaccagatgt tgtccctgag cagcctccca | 1500 |
| ccgtgggctc tcaccctgct ggcatgcatc ctcgtgtcca ttgtcactga gtttgtgagc | 1560 |
| aacccagcaa ccatcaccat cttcctgccc atcctgtgca gcctgtctga aacgctgcac | 1620 |
| attaaccccc tctacaccct gatcccagtc accatgtgca tctccttgc agtgatgctg | 1680 |
| cctgtgggca atccccctaa tgccatcgtc ttcagctatg gcactgcca gatcaaagat | 1740 |
| atggtgaaag ctggcctggg agtcaacgtt attggactgg tgatagtaat ggtggccatc | 1800 |
| aacacctggg gagttagcct cttccacctg gacacttacc agcatgggc gagggtcagc | 1860 |
| aacatcactg atcaagccta a | 1881 |

<210> SEQ ID NO 20
<211> LENGTH: 626
<212> TYPE: PRT
<213> ORGANISM: Homo sapiens

<400> SEQUENCE: 20

Met Gly Leu Leu Gln Gly Leu Leu Arg Val Arg Lys Leu Leu Leu Val
1               5                   10                  15

-continued

```
Val Cys Val Pro Leu Leu Leu Pro Leu Pro Val Leu His Pro Ser
             20                  25             30

Ser Glu Ala Ser Cys Ala Tyr Val Leu Ile Val Thr Ala Val Tyr Trp
             35                  40              45

Val Ser Glu Ala Val Pro Leu Gly Ala Ala Leu Val Pro Ala Phe
 50                  55                  60

Leu Tyr Pro Phe Phe Gly Val Leu Arg Ser Asn Glu Val Ala Ala Glu
 65                  70              75                  80

Tyr Phe Lys Asn Thr Thr Leu Leu Val Gly Val Ile Cys Val Ala
                 85                  90                  95

Ala Ala Val Glu Lys Trp Asn Leu His Lys Arg Ile Ala Leu Arg Met
             100                 105                 110

Val Leu Met Ala Gly Ala Lys Pro Gly Met Leu Leu Leu Cys Phe Met
             115                 120                 125

Cys Cys Thr Thr Leu Leu Ser Met Trp Leu Ser Asn Thr Ser Thr Thr
 130                 135                 140

Ala Met Val Met Pro Ile Val Glu Ala Val Leu Gln Glu Leu Val Ser
 145                 150                 155                 160

Ala Glu Asp Glu Gln Leu Val Ala Gly Asn Ser Asn Thr Glu Glu Ala
             165                 170                 175

Glu Pro Ile Ser Leu Asp Val Lys Asn Ser Gln Pro Ser Leu Glu Leu
             180                 185                 190

Ile Phe Val Asn Glu Glu Ser Asn Ala Asp Leu Thr Thr Leu Met His
             195                 200                 205

Asn Glu Asn Leu Asn Gly Val Pro Ser Ile Thr Asn Pro Ile Lys Thr
 210                 215                 220

Ala Asn Gln His Gln Gly Lys Lys Gln His Pro Ser Gln Glu Lys Pro
 225                 230                 235                 240

Gln Val Leu Thr Pro Ser Pro Arg Lys Gln Lys Leu Asn Arg Lys Tyr
             245                 250                 255

Arg Ser His His Asp Gln Met Ile Cys Lys Cys Leu Ser Leu Ser Ile
             260                 265                 270

Ser Tyr Ser Ala Thr Ile Gly Gly Leu Thr Thr Ile Ile Gly Thr Ser
 275                 280                 285

Thr Ser Leu Ile Phe Leu Glu His Phe Asn Asn Gln Tyr Pro Ala Ala
 290                 295                 300

Glu Val Val Asn Phe Gly Thr Trp Phe Leu Phe Ser Phe Pro Ile Ser
 305                 310                 315                 320

Leu Ile Met Leu Val Val Ser Trp Phe Trp Met His Trp Leu Phe Leu
             325                 330                 335

Gly Cys Asn Phe Lys Glu Thr Cys Ser Leu Ser Lys Lys Lys Thr
             340                 345                 350

Lys Arg Glu Gln Leu Ser Glu Lys Arg Ile Gln Glu Glu Tyr Glu Lys
             355                 360                 365

Leu Gly Asp Ile Ser Tyr Pro Glu Met Val Thr Gly Phe Phe Phe Ile
 370                 375                 380

Leu Met Thr Val Leu Trp Phe Thr Arg Glu Pro Gly Phe Val Pro Gly
 385                 390                 395                 400

Trp Asp Ser Phe Phe Glu Lys Lys Gly Tyr Arg Thr Asp Ala Thr Val
                 405                 410                 415

Ser Val Phe Leu Gly Phe Leu Leu Phe Leu Ile Pro Ala Lys Lys Pro
             420                 425                 430

Cys Phe Gly Lys Lys Asn Asp Gly Glu Asn Gln Glu His Ser Leu Gly
```

```
                435                440                445
          Thr Glu Ser Ile Ile Thr Trp Lys Asp Phe Gln Lys Thr Met Pro Trp
              450                455                460
          Glu Ile Val Ile Leu Val Gly Gly Tyr Ala Leu Ala Ser Gly Ser
          465                470                475                480
          Lys Ser Ser Gly Leu Ser Thr Trp Ile Gly Asn Gln Met Leu Ser Leu
                          485                490                495
          Ser Ser Leu Pro Pro Trp Ala Val Thr Leu Leu Ala Cys Ile Leu Val
                      500                505                510
          Ser Ile Val Thr Glu Phe Val Ser Asn Pro Ala Thr Ile Thr Ile Phe
                  515                520                525
          Leu Pro Ile Leu Cys Ser Leu Ser Glu Thr Leu His Ile Asn Pro Leu
              530                535                540
          Tyr Thr Leu Ile Pro Val Thr Met Cys Ile Ser Phe Ala Val Met Leu
          545                550                555                560
          Pro Val Gly Asn Pro Pro Asn Ala Ile Val Phe Ser Tyr Gly His Cys
                          565                570                575
          Gln Ile Lys Asp Met Val Lys Ala Gly Leu Gly Val Asn Val Ile Gly
                      580                585                590
          Leu Val Ile Val Met Val Ala Ile Asn Thr Trp Gly Val Ser Leu Phe
                  595                600                605
          His Leu Asp Thr Tyr Pro Ala Trp Ala Arg Val Ser Asn Ile Thr Asp
              610                615                620
          Gln Ala
          625

<210> SEQ ID NO 21
<211> LENGTH: 1881
<212> TYPE: DNA
<213> ORGANISM: Homo sapiens

<400> SEQUENCE: 21
atgggcctgc tgcagggcct gctccgagtc cggaagctgc tgctggtcgt ctgcgtcccg      60
ctcctgctgc tgcctctgcc cgtcctccac cccagcagcg aggcctcgtg tgcttacgtg     120
ctgatcgtga ctgctgtgta ctgggtgtcg gaggcagtgc tctgggagc tgcagccctg     180 gtgccggcct tcctytaccc gttcttcgga gtcctccggt ccaatgaggt ggcggcggag     240
tacttcaaga cacccacgct gctgctggtg ggggtcatct cgtggcggc tgccgtggag     300 aagtggaacc tgcataagcg cattgctctg cgcatggtct tgatggccgg rgccaagccg     360
ggcatgctgc tgctctgctt catgtgctgt accacgttgc tgtccatgtg gctgtccaac     420
acctccacca ccgccatggt gatgcccatc gtggaggccg tgctgcagga gctggtcagt     480
gctgaggacg agcagctcgt ggcgggcaac tccaacaccg aagaggccga acccatcagt     540
ctggatgtaa agaacagcca accttctctg gaactcatct ttgtcaatga agagtccaac     600
gcagacctca ccactctgat gcacaacgag aacctgaatg gtgtgccctc gatcaccaac     660
cccatcaaaa ctgcaaacca acaccagggc aagaagcaac acccatccca ggaaaagcca     720
caagtcctga cccccagccc caggaagcag aagctgaaca gaaagtacag gtcccaccat     780
gaccagatga tctgcaagtg cctctcccctg agcatatcct actccgctac cattggcggc     840
ctgaccacca tcatcggcac ctccaccagc ctcatcttcc tggaacactt caacaaccag     900
tatccagccg cagaggtggt gaactttggc acctggttcc tcttcagctt ccccatatcc     960
ctcatcatgc tggtggtcag ctggttctgg atgcactggc tgttcctggg ctgcaatttt    1020
```

-continued

```
aaagagacct gctctctgag caagaagaag aagaccaaaa gggaacagtt gtcagagaag    1080
aggatccaag aagaatatga aaaactggga gacattagct acccagaaat ggtgactgga    1140
tttttcttca tcctgatgac cgtactgtgg tttacccggg agcctggctt tgtccctggc    1200
tgggattctt tctttgaaaa gaaaggctac cgtactgatg ccacagtctc tgtcttcctt    1260
ggcttcctcc tcttcctcat tccagcgaag aagccctgct tgggaaaaa gaatgatgga    1320 gagaaccagg agcactcact ggggaccgag tccatcatca cgtggaagga cttccagaag    1380
accatgccct gggagattgt cattctggtt gggggaggct atgctctggc ttctggtagc    1440
aagagctctg gcctctctac atggattggg aaccagatgt tgtccctgag cagcctccca    1500
ccgtgggctg tcaccctgct ggcatgcatc ctcgtgtcca ttgtcactga gtttgtgagc    1560
aacccagcaa ccatcaccat cttcctgccc atcctgtgca gcctgtctga aacgcagcac    1620 attaacccc tctacaccct gatcccagtc accatgtgca tctcctttgc agtgatgctg    1680
cctgtgggca atccccctaa tgccatcgtc ttcagctatg gcactgcca gatcaaagat    1740 atggtgaaag ctggcctggg agtcaacgtt attggactgg tgatagtaat ggtggccatc    1800
aacacctggg gagttagcct cttccacctg gacacttacc cagcatgggc gagggtcagc    1860
aacatcactg atcaagccta a                                             1881
```

<210> SEQ ID NO 22
<211> LENGTH: 626
<212> TYPE: PRT
<213> ORGANISM: Homo sapiens

<400> SEQUENCE: 22

```
Met Gly Leu Leu Gln Gly Leu Leu Arg Val Arg Lys Leu Leu Leu Val
1               5                   10                  15

Val Cys Val Pro Leu Leu Leu Pro Leu Pro Val Leu His Pro Ser
            20                  25                  30

Ser Glu Ala Ser Cys Ala Tyr Val Leu Ile Val Thr Ala Val Tyr Trp
        35                  40                  45

Val Ser Glu Ala Val Pro Leu Gly Ala Ala Ala Leu Val Pro Ala Phe
    50                  55                  60

Leu Tyr Pro Phe Phe Gly Val Leu Arg Ser Asn Glu Val Ala Ala Glu
65                  70                  75                  80

Tyr Phe Lys Asn Thr Thr Leu Leu Leu Val Gly Val Ile Cys Val Ala
                85                  90                  95

Ala Ala Val Glu Lys Trp Asn Leu His Lys Arg Ile Ala Leu Arg Met
            100                 105                 110

Val Leu Met Ala Gly Ala Lys Pro Gly Met Leu Leu Leu Cys Phe Met
        115                 120                 125

Cys Cys Thr Thr Leu Leu Ser Met Trp Leu Ser Asn Thr Ser Thr Thr
    130                 135                 140

Ala Met Val Met Pro Ile Val Glu Ala Val Leu Gln Glu Leu Val Ser
145                 150                 155                 160

Ala Glu Asp Glu Gln Leu Val Ala Gly Asn Ser Asn Thr Glu Glu Ala
                165                 170                 175

Glu Pro Ile Ser Leu Asp Val Lys Asn Ser Gln Pro Ser Leu Glu Leu
            180                 185                 190

Ile Phe Val Asn Glu Glu Ser Asn Ala Asp Leu Thr Thr Leu Met His
        195                 200                 205

Asn Glu Asn Leu Asn Gly Val Pro Ser Ile Thr Asn Pro Ile Lys Thr
```

-continued

```
              210                 215                 220
Ala Asn Gln His Gln Gly Lys Lys Gln His Pro Ser Gln Glu Lys Pro
225                 230                 235                 240
Gln Val Leu Thr Pro Ser Pro Arg Lys Gln Lys Leu Asn Arg Lys Tyr
                245                 250                 255
Arg Ser His His Asp Gln Met Ile Cys Lys Cys Leu Ser Leu Ser Ile
                260                 265                 270
Ser Tyr Ser Ala Thr Ile Gly Gly Leu Thr Thr Ile Ile Gly Thr Ser
                275                 280                 285
Thr Ser Leu Ile Phe Leu Glu His Phe Asn Asn Gln Tyr Pro Ala Ala
                290                 295                 300
Glu Val Val Asn Phe Gly Thr Trp Phe Leu Phe Ser Phe Pro Ile Ser
305                 310                 315                 320
Leu Ile Met Leu Val Val Ser Trp Phe Trp Met His Trp Leu Phe Leu
                325                 330                 335
Gly Cys Asn Phe Lys Glu Thr Cys Ser Leu Ser Lys Lys Lys Lys Thr
                340                 345                 350
Lys Arg Glu Gln Leu Ser Glu Lys Arg Ile Gln Glu Glu Tyr Glu Lys
                355                 360                 365
Leu Gly Asp Ile Ser Tyr Pro Glu Met Val Thr Gly Phe Phe Phe Ile
                370                 375                 380
Leu Met Thr Val Leu Trp Phe Thr Arg Glu Pro Gly Phe Val Pro Gly
385                 390                 395                 400
Trp Asp Ser Phe Phe Glu Lys Lys Gly Tyr Arg Thr Asp Ala Thr Val
                405                 410                 415
Ser Val Phe Leu Gly Phe Leu Leu Phe Leu Ile Pro Ala Lys Lys Pro
                420                 425                 430
Cys Phe Gly Lys Lys Asn Asp Gly Glu Asn Gln Glu His Ser Leu Gly
                435                 440                 445
Thr Glu Ser Ile Ile Thr Trp Lys Asp Phe Gln Lys Thr Met Pro Trp
                450                 455                 460
Glu Ile Val Ile Leu Val Gly Gly Tyr Ala Leu Ala Ser Gly Ser
465                 470                 475                 480
Lys Ser Ser Gly Leu Ser Thr Trp Ile Gly Asn Gln Met Leu Ser Leu
                485                 490                 495
Ser Ser Leu Pro Pro Trp Ala Val Thr Leu Leu Ala Cys Ile Leu Val
                500                 505                 510
Ser Ile Val Thr Glu Phe Val Ser Asn Pro Ala Thr Ile Thr Ile Phe
                515                 520                 525
Leu Pro Ile Leu Cys Ser Leu Ser Glu Thr Gln His Ile Asn Pro Leu
                530                 535                 540
Tyr Thr Leu Ile Pro Val Thr Met Cys Ile Ser Phe Ala Val Met Leu
545                 550                 555                 560
Pro Val Gly Asn Pro Asn Ala Ile Val Phe Ser Tyr Gly His Cys
                565                 570                 575
Gln Ile Lys Asp Met Val Lys Ala Gly Leu Gly Val Asn Val Ile Gly
                580                 585                 590
Leu Val Ile Val Met Val Ala Ile Asn Thr Trp Gly Val Ser Leu Phe
                595                 600                 605
His Leu Asp Thr Tyr Pro Ala Trp Ala Arg Val Ser Asn Ile Thr Asp
                610                 615                 620
Gln Ala
625
```

<210> SEQ ID NO 23
<211> LENGTH: 1743
<212> TYPE: DNA
<213> ORGANISM: Homo sapiens

<400> SEQUENCE: 23

```
atgggcctgc tgcagggcct gctccgagtc cggaagctgc tgctggtcgt ctgcgtcccg      60
ctcctgctgc tgcctctgcc cgtcctccac cccagcagcg aggcctcgtg tgcttacgtg     120
ctgatcgtga ctgctgtgta ctgggtgtcg gaggcagtgc tctgggagc tgcagccctg     180
gtgccggcct tcctytaccc gttcttcgga gtcctccggt ccaatgaggt ggcggcggag     240
tacttcaaga caccacgct gctgctggtg ggggtcatct gcgtggcggc tgccgtggag     300
aagtggaacc tgcataagcg cattgctctg cgcatggtct tgatggccgg rgccaagccg     360
ggcatgctgc tgctctgctt catgtgctgt accacgttgc tgtccatgtg gctgtccaac     420
acctccacca ccgccatggt gatgcccatc gtggaggccg tgctgcagga gctggtcagt     480
gctgaggacg agcagctcgt ggcgggcaac tccaacaccg aagaggccga acccatcagt     540
ctggatgtaa agaacagcca accttctctg gaactcatct ttgtcaatga gagtccaac     600
gcagacctca ccactctgat gcacaacgag aacctgaatg tgtgccctc gatcaccaac     660
cccatcaaaa ctgcaaacca acaccagggc aagaagcaac acccatccca ggaaaagcca     720
caagtcctga cccccagccc caggaagcag aagctgaaca gaaagtacag gtcccaccat     780
gaccagatga tctgcaagtg cctctccctg agcatatcct actccgctac cattggcggc     840
ctgaccacca tcatcggcac ctccaccagc ctcatcttcc tggaacactt caacaaccag     900
tatccagccg cagaggtggt gaactttggc acctggttcc tcttcagctt ccccatatcc     960
ctcatcatgc tggtggtcag ctggttctgg atgcactggc tgttcctggg ctgcaatttt    1020
aaagagacct gctctctgag caagaagaag aagaccaaaa gggaacagtt gtcagagaag    1080
aggatccaag aagaatatga aaaactggga gacattagct acccagaaat ggtgactgga    1140
ttttcttca tcctgatgac cgtactgtgg tttacccggg agcctggctt tgtccctggc    1200
tgggattctt tctttgaaaa gaaggctac cgtactgatg ccacagtctc tgtcttcctt    1260
ggcttcctcc tcttcctcat tccagcgaag aagccctgct ttgggaaaaa gaatgatgga    1320
gagaaccagg agcactcact ggggaccgag tccatcatca cgtggaagga cttccagaag    1380
accatgccct gggagattgt cattctggtt gggggaggct atgctctggc ttctggtagc    1440
aagagctctg gcctctctac atggattggg aaccagatgt tgtccctgag cagcctccca    1500
ccgtgggctg tcaccctgct ggcatgcatc ctcgtgtcca ttgtcactga gtttgtgagc    1560
aacccagcaa ccatcaccat cttcctgccc atcctgtgca gcctggtgaa agctggcctg    1620
ggagtcaacg ttattggact ggtgatagta atggtggcca tcaacacctg gggagttagc    1680
ctcttccacc tggacactta cccagcatgg gcgagggtca gcaacatcac tgatcaagcc    1740
taa                                                                  1743
```

<210> SEQ ID NO 24
<211> LENGTH: 580
<212> TYPE: PRT
<213> ORGANISM: Homo sapiens

<400> SEQUENCE: 24

```
Met Gly Leu Leu Gln Gly Leu Leu Arg Val Arg Lys Leu Leu Leu Val
 1               5                  10                  15
```

```
Val Cys Val Pro Leu Leu Leu Pro Leu Pro Val Leu His Pro Ser
            20                  25              30

Ser Glu Ala Ser Cys Ala Tyr Val Leu Ile Val Thr Ala Val Tyr Trp
        35                  40                  45

Val Ser Glu Ala Val Pro Leu Gly Ala Ala Leu Val Pro Ala Phe
    50                  55                  60

Leu Tyr Pro Phe Phe Gly Val Leu Arg Ser Asn Glu Val Ala Ala Glu
65                      70                  75                  80

Tyr Phe Lys Asn Thr Thr Leu Leu Val Gly Val Ile Cys Val Ala
                85                  90                  95

Ala Ala Val Glu Lys Trp Asn Leu His Lys Arg Ile Ala Leu Arg Met
            100                 105                 110

Val Leu Met Ala Gly Ala Lys Pro Gly Met Leu Leu Leu Cys Phe Met
            115                 120                 125

Cys Cys Thr Thr Leu Leu Ser Met Trp Leu Ser Asn Thr Ser Thr Thr
    130                 135                 140

Ala Met Val Met Pro Ile Val Glu Ala Val Leu Gln Glu Leu Val Ser
145                 150                 155                 160

Ala Glu Asp Glu Gln Leu Val Ala Gly Asn Ser Asn Thr Glu Glu Ala
                165                 170                 175

Glu Pro Ile Ser Leu Asp Val Lys Asn Ser Gln Pro Ser Leu Glu Leu
                180                 185                 190

Ile Phe Val Asn Glu Glu Ser Asn Ala Asp Leu Thr Thr Leu Met His
            195                 200                 205

Asn Glu Asn Leu Asn Gly Val Pro Ser Ile Thr Asn Pro Ile Lys Thr
210                 215                 220

Ala Asn Gln His Gln Gly Lys Lys Gln His Pro Ser Gln Glu Lys Pro
225                 230                 235                 240

Gln Val Leu Thr Pro Ser Pro Arg Lys Gln Lys Leu Asn Arg Lys Tyr
                245                 250                 255

Arg Ser His His Asp Gln Met Ile Cys Lys Cys Leu Ser Leu Ser Ile
            260                 265                 270

Ser Tyr Ser Ala Thr Ile Gly Gly Leu Thr Thr Ile Ile Gly Thr Ser
    275                 280                 285

Thr Ser Leu Ile Phe Leu Glu His Phe Asn Asn Gln Tyr Pro Ala Ala
290                 295                 300

Glu Val Val Asn Phe Gly Thr Trp Phe Leu Phe Ser Phe Pro Ile Ser
305                 310                 315                 320

Leu Ile Met Leu Val Val Ser Trp Phe Trp Met His Trp Leu Phe Leu
            325                 330                 335

Gly Cys Asn Phe Lys Glu Thr Cys Ser Leu Ser Lys Lys Lys Thr
            340                 345                 350

Lys Arg Glu Gln Leu Ser Glu Lys Arg Ile Gln Glu Tyr Glu Lys
        355                 360                 365

Leu Gly Asp Ile Ser Tyr Pro Glu Met Val Thr Gly Phe Phe Ile
        370                 375                 380

Leu Met Thr Val Leu Trp Phe Thr Arg Glu Pro Gly Phe Val Pro Gly
385                 390                 395                 400

Trp Asp Ser Phe Phe Glu Lys Lys Gly Tyr Arg Thr Asp Ala Thr Val
                405                 410                 415

Ser Val Phe Leu Gly Phe Leu Leu Phe Leu Ile Pro Ala Lys Lys Pro
                420                 425                 430
```

```
Cys Phe Gly Lys Lys Asn Asp Gly Glu Asn Gln Glu His Ser Leu Gly
            435                 440                 445
Thr Glu Ser Ile Ile Thr Trp Lys Asp Phe Gln Lys Thr Met Pro Trp
        450                 455                 460
Glu Ile Val Ile Leu Val Gly Gly Tyr Ala Leu Ala Ser Gly Ser
465                 470                 475                 480
Lys Ser Ser Gly Leu Ser Thr Trp Ile Gly Asn Gln Met Leu Ser Leu
                485                 490                 495
Ser Ser Leu Pro Pro Trp Ala Val Thr Leu Leu Ala Cys Ile Leu Val
            500                 505                 510
Ser Ile Val Thr Glu Phe Val Ser Asn Pro Ala Thr Ile Thr Ile Phe
        515                 520                 525
Leu Pro Ile Leu Cys Ser Leu Val Lys Ala Gly Leu Gly Val Asn Val
        530                 535                 540
Ile Gly Leu Val Ile Val Met Val Ala Ile Asn Thr Trp Gly Val Ser
545                 550                 555                 560
Leu Phe His Leu Asp Thr Tyr Pro Ala Trp Ala Arg Val Ser Asn Ile
                565                 570                 575
Thr Asp Gln Ala
            580

<210> SEQ ID NO 25
<211> LENGTH: 2019
<212> TYPE: DNA
<213> ORGANISM: Homo sapiens

<400> SEQUENCE: 25
atgagtggct tcttcacctc gctggacccc cggcgggtgc agtggggagc tgcctggtat      60
gcaatgcact ccaggatcct acgcaccaaa ccagtggagt ccatgctaga gggaactggg     120
accaccacgg cacatggaac taagctagcc caggtactca ccacagtgga cctcatctct     180
cttggcgttg gcagctgtgt gggcactggc atgtatgtgg tctctggcct ggtggccaag     240
gaaatggcag gacctggtgt cattgtgtcc ttcatcattg cagccgtcgc atccatatta     300
tcaggcgtct gctatgcaga gtttggagtt cgagtcccca gaccacagg atctgcctac     360 acctacagct atgtcactgt tggggaattt gtggcatttt tcattggctg gaacctgatc     420
ctggagtacc tgattggcac tgcggccgga gccagtgctc tgagcagcat gtttgactca     480
ctagccaacc acaccatcag ccgctggatg gcggacagcg tgggaaccct caatggcctg     540
gggaaaggtg aagaatcata cccagacctt ctggctctgt tgatcgcggt catcgtgacc     600
atcattgttc tctgggggt gaagaattcc ataggcttca acaatgttct caatgtgctg     660
aacctggtag tatgggtgtt catcatgatc gcaggcctct tcttcatcaa tgggaaatac     720
tgggcggagg ccagttcttg ccccacggc tggtcagggg tgctgcaagg agcagcaaca     780
tgcttctacg ctttcattgg ctttgacatc atcgccacca ctggagagga agccaagaat     840
cccaacacgt ccatccctta tgctatcact gcctccctgg tcatctgcct gacagcatat     900
gtgtctgtga gcgtgatctt aactctgatg gtgccatatt ataccattga cacggaatcc     960
ccactcatgg agatgtttgt ggctcatggg ttctatgctg ccaaattcgt agtggccatt    1020
gggtcggttg caggactgac agtcagcttg ctggggtccc tcttcccgat gccgagggtc    1080
atttatgcca tggctggtga cgggctcctt tcaggttcc tggctcacgt cagctcctac    1140
acagagacac cagtggtggc ctgcatcgtg tcagggttcc tggcagcgct cctcgcactg    1200
ttggtcagct tgagagacct gatagagatg atgtctatcg gcacgctcct ggcctacacc    1260
```

-continued

```
ttggtctctg tctgtgtctt gctccttcga taccaacctg agagtgacat tgatggtttt   1320
gtcaagttct tgtctgagga gcacaccaag aagaaggagg gcattctggc tgactgtgag   1380
aaggaagctt gttctcctgt gagtgagggg gatgagtttt ctggcccagc caccaacaca   1440
tgtggggcca agaacttacc atccttggga gacaatgaga tgctcatagg gaaatcagac   1500
aagtcaacct acaacgtcaa ccaccccaat tacggcaccg tggacatgac cacaggcata   1560
gaagctgatg aatccgaaaa tatttatctc atcaagttaa agaaactgat tgggcctcat   1620
tattacacca tgagaatccg gctgggcctt ccaggcaaaa tggaccggcc cacagcagcg   1680
acggggcaca cggtgaccat ctgcgtgctc ctgctcttca tcctcatgtt catcttctgc   1740
tccttcatca tctttggttc tgactacatc tcagagcaga gctggtgggc catccttctg   1800
gttgttctga tggtgctgct gatcagcacc ctggtgtttg tgatcctgca gcagccagag   1860
aaccccaaga agctgcccta catggcccct tgcctcccct tgtgcctgc ctttgccatg    1920 ctggtgaaca tctatctcat gctaaagctc tccaccatca catggatccg gtttgcggtc   1980
tggtgctttg tgggtaagca acttcctttg gagccttaa                          2019
```

<210> SEQ ID NO 26
<211> LENGTH: 672
<212> TYPE: PRT
<213> ORGANISM: Homo sapiens

<400> SEQUENCE: 26

```
Met Ser Gly Phe Phe Thr Ser Leu Asp Pro Arg Arg Val Gln Trp Gly
 1               5                  10                  15

Ala Ala Trp Tyr Ala Met His Ser Arg Ile Leu Arg Thr Lys Pro Val
             20                  25                  30

Glu Ser Met Leu Glu Gly Thr Gly Thr Thr Thr Ala His Gly Thr Lys
         35                  40                  45

Leu Ala Gln Val Leu Thr Thr Val Asp Leu Ile Ser Leu Gly Val Gly
     50                  55                  60

Ser Cys Val Gly Thr Gly Met Tyr Val Val Ser Gly Leu Val Ala Lys
 65                  70                  75                  80

Glu Met Ala Gly Pro Gly Val Ile Val Ser Phe Ile Ala Ala Val
             85                  90                  95

Ala Ser Ile Leu Ser Gly Val Cys Tyr Ala Glu Phe Gly Val Arg Val
            100                 105                 110

Pro Lys Thr Thr Gly Ser Ala Tyr Thr Tyr Ser Tyr Val Thr Val Gly
        115                 120                 125

Glu Phe Val Ala Phe Phe Ile Gly Trp Asn Leu Ile Leu Glu Tyr Leu
    130                 135                 140

Ile Gly Thr Ala Ala Gly Ala Ser Ala Leu Ser Ser Met Phe Asp Ser
145                 150                 155                 160

Leu Ala Asn His Thr Ile Ser Arg Trp Met Ala Asp Ser Val Gly Thr
                165                 170                 175

Leu Asn Gly Leu Gly Lys Gly Glu Glu Ser Tyr Pro Asp Leu Leu Ala
            180                 185                 190

Leu Leu Ile Ala Val Ile Val Thr Ile Val Ala Leu Gly Val Lys
        195                 200                 205

Asn Ser Ile Gly Phe Asn Asn Val Leu Asn Val Leu Asn Leu Val Val
    210                 215                 220

Trp Val Phe Ile Met Ile Ala Gly Leu Phe Phe Ile Asn Gly Lys Tyr
225                 230                 235                 240
```

-continued

```
Trp Ala Glu Gly Gln Phe Leu Pro His Gly Trp Ser Gly Val Leu Gln
                245                 250                 255
Gly Ala Ala Thr Cys Phe Tyr Ala Phe Ile Gly Phe Asp Ile Ile Ala
            260                 265                 270
Thr Thr Gly Glu Glu Ala Lys Asn Pro Asn Thr Ser Ile Pro Tyr Ala
        275                 280                 285
Ile Thr Ala Ser Leu Val Ile Cys Leu Thr Ala Tyr Val Ser Val Ser
    290                 295                 300
Val Ile Leu Thr Leu Met Val Pro Tyr Tyr Thr Ile Asp Thr Glu Ser
305                 310                 315                 320
Pro Leu Met Glu Met Phe Val Ala His Gly Phe Tyr Ala Ala Lys Phe
                325                 330                 335
Val Val Ala Ile Gly Ser Val Ala Gly Leu Thr Val Ser Leu Leu Gly
            340                 345                 350
Ser Leu Phe Pro Met Pro Arg Val Ile Tyr Ala Met Ala Gly Asp Gly
        355                 360                 365
Leu Leu Phe Arg Phe Leu Ala His Val Ser Ser Tyr Thr Glu Thr Pro
    370                 375                 380
Val Val Ala Cys Ile Val Ser Gly Phe Leu Ala Ala Leu Leu Ala Leu
385                 390                 395                 400
Leu Val Ser Leu Arg Asp Leu Ile Glu Met Met Ser Ile Gly Thr Leu
                405                 410                 415
Leu Ala Tyr Thr Leu Val Ser Val Cys Val Leu Leu Leu Arg Tyr Gln
            420                 425                 430
Pro Glu Ser Asp Ile Asp Gly Phe Val Lys Phe Leu Ser Glu His
        435                 440                 445
Thr Lys Lys Lys Glu Gly Ile Leu Ala Asp Cys Glu Lys Glu Ala Cys
    450                 455                 460
Ser Pro Val Ser Glu Gly Asp Glu Phe Ser Gly Pro Ala Thr Asn Thr
465                 470                 475                 480
Cys Gly Ala Lys Asn Leu Pro Ser Leu Gly Asp Asn Glu Met Leu Ile
                485                 490                 495
Gly Lys Ser Asp Lys Ser Thr Tyr Asn Val Asn His Pro Asn Tyr Gly
            500                 505                 510
Thr Val Asp Met Thr Thr Gly Ile Glu Ala Asp Glu Ser Glu Asn Ile
        515                 520                 525
Tyr Leu Ile Lys Leu Lys Lys Leu Ile Gly Pro His Tyr Tyr Thr Met
    530                 535                 540
Arg Ile Arg Leu Gly Leu Pro Gly Lys Met Asp Arg Pro Thr Ala Ala
545                 550                 555                 560
Thr Gly His Thr Val Thr Ile Cys Val Leu Leu Phe Ile Leu Met
                565                 570                 575
Phe Ile Phe Cys Ser Phe Ile Ile Phe Gly Ser Asp Tyr Ile Ser Glu
            580                 585                 590
Gln Ser Trp Trp Ala Ile Leu Leu Val Val Leu Met Val Leu Leu Ile
        595                 600                 605
Ser Thr Leu Val Phe Val Ile Leu Gln Gln Pro Glu Asn Pro Lys Lys
    610                 615                 620
Leu Pro Tyr Met Ala Pro Cys Leu Pro Phe Val Pro Ala Phe Ala Met
625                 630                 635                 640
Leu Val Asn Ile Tyr Leu Met Leu Lys Leu Ser Thr Ile Thr Trp Ile
                645                 650                 655
```

Arg Phe Ala Val Trp Cys Phe Val Gly Lys Gln Leu Pro Leu Glu Pro
            660                 665                 670

<210> SEQ ID NO 27
<211> LENGTH: 2019
<212> TYPE: DNA
<213> ORGANISM: Homo sapiens

<400> SEQUENCE: 27

| | | | |
|---|---|---|---|
| atgagtggct tcttcacctc gctggacccc cggcgggtgc agtggggagc tgcctggtat | 60 |
| gcaatgcact ccaggatcct acgcaccaaa ccagtggagt ccatgctaga gggaactggg | 120 |
| accaccacgg cacatggaac taagctagcc caggtactca ccacagtgga cctcatctct | 180 |
| cttggcgttg gcagctgtgt gggcactggc atgtatgtgg tctctggcct ggtggccaag | 240 |
| gaaatggcag gacctggtgt cattgtgtcc ttcatcattg cagccgtcgc atccatatta | 300 |
| tcaggcgtct gctatgcaga gtttggagtt cgagtcccca agaccacagg atctgcctac | 360 |
| acctacagct atgtcactgt tggggaattt gtggcatttt cattggctg gaacctgatc | 420 |
| ctggagtacc tgattggcac tgcggccgga gccagtgctc tgagcagcat gtttgactca | 480 |
| ctagccaacc acaccatcag ccgctggatg gcggacagcg tgggaaccct caatggcctg | 540 |
| gggaaaggtg aagaatcata cccagacctt ctggctctgt tgatcgcggt catcgtgacc | 600 |
| atcattgttg ctctgggggt gaagaattcc ataggcttca acaatgttct caatgtgctg | 660 |
| aacctggcag tatgggtgtt catcatgatc gcaggcctct tcttcatcaa tgggaaatac | 720 |
| tgggcggagg ccagttctt gccccacggc tggtcagggg tgctgcaagg agcagcaaca | 780 |
| tgcttctacg ctttcattgg ctttgacatc atcgccacca ctggagagga agccaagaat | 840 |
| cccaacacgt ccatccctta tgctatcact gcctccctgg tcatctgcct gacagcatat | 900 |
| gtgtctgtga gcgtgatctt aactctgatg gtgccatatt ataccattga cacggaatcc | 960 |
| ccactcatgg agatgtttgt ggctcatggg ttctatgctg ccaaattcgt agtggccatt | 1020 |
| gggtcggttg caggactgac agtcagcttg ctggggtccc tcttcccgat gccgagggtc | 1080 |
| atttatgcca tggctggtga cgggctcctt ttcaggttcc tggctcacgt cagctcctac | 1140 |
| acagagacac cagtggtggc ctgcatcgtg tcagggttcc tggcagcgct cctcgcactg | 1200 |
| ttggtcagct tgagagacct gatagagatg atgtctatcg gcacgctcct ggcctacacc | 1260 |
| ttggtctctg tctgtgtctt gctccttcga taccaacctg agagtgacat tgatggtttt | 1320 |
| gtcaagttct tgtctgagga gcacaccaag aagaaggagg gcattctggc tgactgtgag | 1380 |
| aaggaagctt gttctcctgt gagtgagggg gatgagtttt ctggcccagc caccaacaca | 1440 |
| tgtgggca agaacttacc atccttggga gacaatgaga tgctcatagg gaaatcagac | 1500 |
| aagtcaacct acaacgtcaa ccaccccaat tacggcaccg tggacatgac cacaggcata | 1560 |
| gaagctgatg aatccgaaaa tatttatctc atcaagttaa agaaactgat tgggcctcat | 1620 |
| tattaccacca tgagaatccg gctgggcctt ccaggcaaaa tggaccggcc cacagcagcg | 1680 |
| acggggcaca cggtgaccat ctgcgtgctc tgctcttca tcctcatgtt catcttctgc | 1740 |
| tccttcatca tctttggttc tgactacatc tcagagcaga gctggtgggc catccttctg | 1800 |
| gttgttctga tggtgctgct gatcagcacc ctggtgtttg tgatcctgca gcagccagag | 1860 |
| aaccccaaga gctgcccta catggcccct gcctcccct tgtgcctgc ctttgccatg | 1920 |
| ctggtgaaca tctatctcat gctaaagctc tccaccatca catggatccg gtttgcggtc | 1980 |
| tggtgctttg tgggtaagca acttcctttg gagccttaa | 2019 |

```
<210> SEQ ID NO 28
<211> LENGTH: 672
<212> TYPE: PRT
<213> ORGANISM: Homo sapiens

<400> SEQUENCE: 28

Met Ser Gly Phe Phe Thr Ser Leu Asp Pro Arg Arg Val Gln Trp Gly
 1               5                  10                  15

Ala Ala Trp Tyr Ala Met His Ser Arg Ile Leu Arg Thr Lys Pro Val
            20                  25                  30

Glu Ser Met Leu Glu Gly Thr Gly Thr Thr Ala His Gly Thr Lys
        35                  40                  45

Leu Ala Gln Val Leu Thr Thr Val Asp Leu Ile Ser Leu Gly Val Gly
    50                  55                  60

Ser Cys Val Gly Thr Gly Met Tyr Val Val Ser Gly Leu Val Ala Lys
65                  70                  75                  80

Glu Met Ala Gly Pro Gly Val Ile Val Ser Phe Ile Ala Ala Val
                85                  90                  95

Ala Ser Ile Leu Ser Gly Val Cys Tyr Ala Glu Phe Gly Val Arg Val
            100                 105                 110

Pro Lys Thr Thr Gly Ser Ala Tyr Thr Tyr Ser Tyr Val Thr Val Gly
        115                 120                 125

Glu Phe Val Ala Phe Phe Ile Gly Trp Asn Leu Ile Leu Glu Tyr Leu
130                 135                 140

Ile Gly Thr Ala Ala Gly Ala Ser Ala Leu Ser Ser Met Phe Asp Ser
145                 150                 155                 160

Leu Ala Asn His Thr Ile Ser Arg Trp Met Ala Asp Ser Val Gly Thr
                165                 170                 175

Leu Asn Gly Leu Gly Lys Gly Glu Ser Tyr Pro Asp Leu Leu Ala
            180                 185                 190

Leu Leu Ile Ala Val Ile Val Thr Ile Ile Val Ala Leu Gly Val Lys
        195                 200                 205

Asn Ser Ile Gly Phe Asn Asn Val Leu Asn Val Leu Asn Leu Ala Val
    210                 215                 220

Trp Val Phe Ile Met Ile Ala Gly Leu Phe Phe Ile Asn Gly Lys Tyr
225                 230                 235                 240

Trp Ala Glu Gly Gln Phe Leu Pro His Gly Trp Ser Gly Val Leu Gln
                245                 250                 255

Gly Ala Ala Thr Cys Phe Tyr Ala Phe Ile Gly Phe Asp Ile Ile Ala
            260                 265                 270

Thr Thr Gly Glu Glu Ala Lys Asn Pro Asn Thr Ser Ile Pro Tyr Ala
        275                 280                 285

Ile Thr Ala Ser Leu Val Ile Cys Leu Thr Ala Tyr Val Ser Val Ser
    290                 295                 300

Val Ile Leu Thr Leu Met Val Pro Tyr Tyr Thr Ile Asp Thr Glu Ser
305                 310                 315                 320

Pro Leu Met Glu Met Phe Val Ala His Gly Phe Tyr Ala Ala Lys Phe
                325                 330                 335

Val Val Ala Ile Gly Ser Val Ala Gly Leu Thr Val Ser Leu Leu Gly
            340                 345                 350

Ser Leu Phe Pro Met Pro Arg Val Ile Tyr Ala Met Ala Gly Asp Gly
        355                 360                 365

Leu Leu Phe Arg Phe Leu Ala His Val Ser Ser Tyr Thr Glu Thr Pro
    370                 375                 380
```

-continued

```
Val Val Ala Cys Ile Val Ser Gly Phe Leu Ala Ala Leu Leu Ala Leu
385                 390                 395                 400

Leu Val Ser Leu Arg Asp Leu Ile Glu Met Met Ser Ile Gly Thr Leu
            405                 410                 415

Leu Ala Tyr Thr Leu Val Ser Val Cys Val Leu Leu Arg Tyr Gln
            420                 425                 430

Pro Glu Ser Asp Ile Asp Gly Phe Val Lys Phe Leu Ser Glu Glu His
            435                 440                 445

Thr Lys Lys Glu Gly Ile Leu Ala Asp Cys Glu Lys Glu Ala Cys
            450                 455                 460

Ser Pro Val Ser Glu Gly Asp Glu Phe Ser Gly Pro Ala Thr Asn Thr
465                 470                 475                 480

Cys Gly Ala Lys Asn Leu Pro Ser Leu Gly Asp Asn Glu Met Leu Ile
            485                 490                 495

Gly Lys Ser Asp Lys Ser Thr Tyr Asn Val Asn His Pro Asn Tyr Gly
            500                 505                 510

Thr Val Asp Met Thr Thr Gly Ile Glu Ala Asp Glu Ser Glu Asn Ile
            515                 520                 525

Tyr Leu Ile Lys Leu Lys Lys Leu Ile Gly Pro His Tyr Tyr Thr Met
            530                 535                 540

Arg Ile Arg Leu Gly Leu Pro Gly Lys Met Asp Arg Pro Thr Ala Ala
545                 550                 555                 560

Thr Gly His Thr Val Thr Ile Cys Val Leu Leu Phe Ile Leu Met
            565                 570                 575

Phe Ile Phe Cys Ser Phe Ile Ile Phe Gly Ser Asp Tyr Ile Ser Glu
            580                 585                 590

Gln Ser Trp Trp Ala Ile Leu Leu Val Val Leu Met Val Leu Leu Ile
            595                 600                 605

Ser Thr Leu Val Phe Val Ile Leu Gln Gln Pro Glu Asn Pro Lys Lys
            610                 615                 620

Leu Pro Tyr Met Ala Pro Cys Leu Pro Phe Val Pro Ala Phe Ala Met
625                 630                 635                 640

Leu Val Asn Ile Tyr Leu Met Leu Lys Leu Ser Thr Ile Thr Trp Ile
            645                 650                 655

Arg Phe Ala Val Trp Cys Phe Val Gly Lys Gln Leu Pro Leu Glu Pro
            660                 665                 670
```

<210> SEQ ID NO 29
<211> LENGTH: 777
<212> TYPE: DNA
<213> ORGANISM: Homo sapiens

<400> SEQUENCE: 29

```
atgagtggct tcttcacctc gctggacccc cggcgggtgc agtggggagc tgcctggtat      60
gcaatgcact ccaggatcct acgcaccaaa ccagtggagt ccatgctaga gggaactggg     120
accaccacgg cacatggaac taagctagcc caggtactca ccacagtgga cctcatctct     180
cttggcgttg gcagctgtgt gggcactggc atgtatgtgg tctctggcct ggtggccaag     240
gaaatggcag gacctggtgt cattgtgtcc ttcatcattg cagccgtcgc atccatatta     300
tcaggcgtct gctatgcaga gtttggagtt cgagtcccca agaccacagg atctgcctac     360
acctacagct atgtcactgt tggggaattt gtggcatttt cattggctg aacctgatc       420
ctggagtacc tgattggcac tgcggccgga gccagtgctc tgagcagcat gtttgactca     480
```

```
ctagccaacc acaccatcag ccgctggatg gcggacagcg tgggaaccct caatggcctg      540
gggaaaggtg aagaatcata cccagacctt ctggctctgt tgatcgcggt catcgtgacc      600
atcattgttg ctctgggggt gaagaattcc ataggcttca acaatgttct caatgtgctg      660
aacctggtag tatgggtgtt catcatgatc gcaggcctct tcttcatcaa tgggaaatac      720
tgggcggagg gccagttctt gccccacggc tggtcaggga agccctccag caactga         777
```

<210> SEQ ID NO 30
<211> LENGTH: 258
<212> TYPE: PRT
<213> ORGANISM: Homo sapiens

<400> SEQUENCE: 30

```
Met Ser Gly Phe Phe Thr Ser Leu Asp Pro Arg Arg Val Gln Trp Gly
 1               5                  10                  15

Ala Ala Trp Tyr Ala Met His Ser Arg Ile Leu Arg Thr Lys Pro Val
                20                  25                  30

Glu Ser Met Leu Glu Gly Thr Gly Thr Thr Ala His Gly Thr Lys
            35                  40                  45

Leu Ala Gln Val Leu Thr Thr Val Asp Leu Ile Ser Leu Gly Val Gly
        50                  55                  60

Ser Cys Val Gly Thr Gly Met Tyr Val Val Ser Gly Leu Val Ala Lys
 65                  70                  75                  80

Glu Met Ala Gly Pro Gly Val Ile Val Ser Phe Ile Ala Ala Val
                85                  90                  95

Ala Ser Ile Leu Ser Gly Val Cys Tyr Ala Glu Phe Gly Val Arg Val
            100                 105                 110

Pro Lys Thr Thr Gly Ser Ala Tyr Thr Tyr Ser Tyr Val Thr Val Gly
        115                 120                 125

Glu Phe Val Ala Phe Ile Gly Trp Asn Leu Ile Leu Glu Tyr Leu
    130                 135                 140

Ile Gly Thr Ala Ala Gly Ala Ser Ala Leu Ser Ser Met Phe Asp Ser
145                 150                 155                 160

Leu Ala Asn His Thr Ile Ser Arg Trp Met Ala Asp Ser Val Gly Thr
                165                 170                 175

Leu Asn Gly Leu Gly Lys Gly Glu Glu Ser Tyr Pro Asp Leu Leu Ala
            180                 185                 190

Leu Leu Ile Ala Val Ile Val Thr Ile Ile Val Ala Leu Gly Val Lys
        195                 200                 205

Asn Ser Ile Gly Phe Asn Asn Val Leu Asn Val Leu Asn Leu Val Val
    210                 215                 220

Trp Val Phe Ile Met Ile Ala Gly Leu Phe Phe Ile Asn Gly Lys Tyr
225                 230                 235                 240

Trp Ala Glu Gly Gln Phe Leu Pro His Gly Trp Ser Gly Lys Pro Ser
                245                 250                 255

Ser Asn
```

<210> SEQ ID NO 31
<211> LENGTH: 777
<212> TYPE: DNA
<213> ORGANISM: Homo sapiens

<400> SEQUENCE: 31

```
atgagtggct tcttcacctc gctggacccc cggcgggtgc agtggggagc tgcctggtat      60
gcaatgcact ccaggatcct acgcaccaaa ccagtggagt ccatgctaga gggaactggg     120
```

-continued

```
accaccacgg cacatggaac taagctagcc caggtactca ccacagtgga cctcatctct    180
cttggcgttg gcagctgtgt gggcactggc atgtatgtgg tctctggcct ggtggccaag    240
gaaatggcag gacctggtgt cattgtgtcc ttcatcattg cagccgtcgc atccatatta    300
tcaggcgtct gctatgcaga gtttggagtt cgagtcccca agaccacagg atctgcctac    360
acctacagct atgtcactgt tggggaattt gtggcatttt tcattggctg gaacctgatc    420
ctggagtacc tgattggcac tgcggccgga gccagtgctc tgagcagcat gtttgactca    480
ctagccaacc acaccatcag ccgctggatg gcggacagcg tgggaaccct caatggcctg    540
gggaaaggtg aagaatcata cccagacctt ctggctctgt tgatcgcggt catcgtgacc    600
atcattgttg ctctgggggt gaagaattcc ataggcttca acaatgttct caatgtgctg    660
aacctggcag tatgggtgtt catcatgatc gcaggcctct tcttcatcaa tgggaaatac    720
tgggcggagg ccagttcttg ccccacggc tggtcaggga gccctccag caactga        777
```

<210> SEQ ID NO 32
<211> LENGTH: 258
<212> TYPE: PRT
<213> ORGANISM: Homo sapiens

<400> SEQUENCE: 32

```
Met Ser Gly Phe Phe Thr Ser Leu Asp Pro Arg Arg Val Gln Trp Gly
 1               5                  10                  15

Ala Ala Trp Tyr Ala Met His Ser Arg Ile Leu Arg Thr Lys Pro Val
            20                  25                  30

Glu Ser Met Leu Glu Gly Thr Gly Thr Thr Ala His Gly Thr Lys
        35                  40                  45

Leu Ala Gln Val Leu Thr Thr Val Asp Leu Ile Ser Leu Gly Val Gly
    50                  55                  60

Ser Cys Val Gly Thr Gly Met Tyr Val Val Ser Gly Leu Val Ala Lys
65                  70                  75                  80

Glu Met Ala Gly Pro Gly Val Ile Val Ser Phe Ile Ile Ala Ala Val
                85                  90                  95

Ala Ser Ile Leu Ser Gly Val Cys Tyr Ala Glu Phe Gly Val Arg Val
            100                 105                 110

Pro Lys Thr Thr Gly Ser Ala Tyr Thr Tyr Ser Tyr Val Thr Val Gly
        115                 120                 125

Glu Phe Val Ala Phe Phe Ile Gly Trp Asn Leu Ile Leu Glu Tyr Leu
    130                 135                 140

Ile Gly Thr Ala Ala Gly Ala Ser Ala Leu Ser Ser Met Phe Asp Ser
145                 150                 155                 160

Leu Ala Asn His Thr Ile Ser Arg Trp Met Ala Asp Ser Val Gly Thr
                165                 170                 175

Leu Asn Gly Leu Gly Lys Gly Glu Glu Ser Tyr Pro Asp Leu Leu Ala
            180                 185                 190

Leu Leu Ile Ala Val Ile Val Thr Ile Ile Val Ala Leu Gly Val Lys
        195                 200                 205

Asn Ser Ile Gly Phe Asn Asn Val Leu Asn Val Leu Asn Leu Ala Val
    210                 215                 220

Trp Val Phe Ile Met Ile Ala Gly Leu Phe Phe Ile Asn Gly Lys Tyr
225                 230                 235                 240
```

```
-continued

Trp Ala Glu Gly Gln Phe Leu Pro His Gly Trp Ser Gly Lys Pro Ser
                245                 250                 255
Ser Asn
```

NUCLEIC ACIDS ENCODING HUMAN TRANSPORTER PROTEINS

This application claims priority under 35 U.S.C. §119(e) to U.S. provisional patent application No. 60/130,552 filed Apr. 22, 1999, which is hereby incorporated by reference in its entirety.

1. INTRODUCTION

The present invention relates to the discovery, identification and characterization of novel human polynucleotides that encode proteins sharing structural similarity with transporter proteins. The invention encompasses the described polynucleotides, host cell expression systems, the encoded proteins, fusion proteins, polypeptides and peptides, antibodies to the encoded proteins and peptides, and genetically engineered animals that lack at least one of the disclosed genes, or over express the disclosed genes, antagonists and agonists of the described proteins, and other compounds that modulate the expression or activity of the proteins encoded by the disclosed genes that can be used for diagnosis, drug screening, clinical trial monitoring, and/or the treatment of physiological or behavioral disorders.

2. BACKGROUND OF THE INVENTION

Transporter proteins are used to facilitate the translocation of certain molecules either into or out of the cell. Often, such transporters work by "pumping" ions across the cell membrane and co-transporting specific molecules (amino acids, amino acid derivatives and precursors, dicarboxylates, inorganic molecules, etc.) across the membrane. Such mechanisms play important roles in maintaining cellular and metabolic homeostasis, neuron function, signaling, and drug resistance. As such, transporter proteins constitute compelling targets for the development and study of novel therapeutic agents.

3. SUMMARY OF THE INVENTION

The present invention relates to the discovery, identification and characterization of nucleotides that encode novel transporter proteins, and the corresponding amino acid sequences of the described novel transporter proteins (NTPs). The NTPs described for the first time herein, are transmembrane proteins that span the cellular membrane and are involved in translocating molecules across membranes. The described NTPs share structural similarity with a variety of transporter proteins. The sequences encoding the NTPs were initially identified via chimeric gene trap transcripts generated in human cells. The novel human NTPs described herein, encode proteins of 627, 627, 581, 627, 627, 581, 626, 626, 580, 626, 626, 580, 672, 672, 258, and 258 amino acids in length (see SEQ ID NOS: 2, 4, 6, 8, 10, 12, 14, 16, 18, 20, 22, 24, 26, 28, 30, and 32 respectively). The described NTPs have hydrophobic leader sequences and transmembrane regions (of about 20–30 amino acids) characteristic of transporter proteins.

The invention encompasses the nucleotides presented in the Sequence Listing, host cells expressing such nucleotides, the expression products of such nucleotides, and: (a) nucleotides that encode mammalian homologues of the described NTPs including the specifically described human NTP genes; (b) nucleotides that encode one or more portions that correspond to functional domains of a NTP, as well as the polypeptide products specified by such nucleotide sequences, including but not limited to the novel regions of any extracellular domain(s) (ECD), one or more transmembrane domain(s) (TM), and the cytoplasmic domain(s) (CD); (c) isolated nucleotides that encode mutants, engineered or naturally occurring, of the described NTPs in which all or a part of at least one of the domains is deleted or altered, and the polypeptide products specified by such nucleotide sequences, including but not limited to soluble receptors in which all or a portion of a TM is deleted, and nonfunctional receptors in which all or a portion of a CD is deleted; (d) nucleotides that encode fusion proteins containing the coding region from a NTP, or one of its domains (e.g., an extracellular domain) fused to another peptide or polypeptide.

The invention also encompasses agonists and antagonists of the NTPs, including small molecules, large molecules, mutated NTPs, or portions thereof, and antibodies, as well as nucleotide sequences that can be used to inhibit the expression of the described NTPs (e.g., antisense and ribozyme molecules, and gene or regulatory sequence replacement constructs) or to enhance the expression of the described NTP genes (e.g., expression constructs that place the described genes under the control of a strong promoter), and transgenic animals that express a NTP transgene or "knockouts" (which can be conditional) that do not express a functional NTP (see, for example, PCT Applic. No. PCT/US98/03243, filed Feb. 20, 1998, herein incorporated by reference). In addition to knock-outs, an additional aspect of the present invention includes animals having genetically engineered mutations in at least one of the described genes that modify the activity or expression of the NTP (i.e., point mutations, over-expression mutations, etc.).

Further, the present invention also relates to methods for the use of the described NTP genes and/or NTPs for the identification of compounds that modulate, i.e., act as agonists or antagonists, of NTP gene expression and or NTP activity. Such compounds can be used as therapeutic agents for the treatment of various symptomatic representations of biological disorders or imbalances.

4. DESCRIPTION OF THE SEQUENCE LISTING

The Sequence Listing provides the sequence of the described NTP polynucleotides, and the amino acid sequences encoded thereby.

5. DETAILED DESCRIPTION OF THE INVENTION

The human NTPs described for the first time herein, are novel transporter proteins that are expressed by genes present in human cells. As transporter proteins, the NTPs are membrane associated proteins that span the lipid bilayer (i.e., transmembrane proteins). Transporter proteins perform a wide variety of roles in the body varying from, inter alia, amino acid scavenging, recycling neurotransmitters, control of blood volume/pressure, nutrient and fluid absorption, energy production, etc. Interfering with, neutralizing, or enhancing NTP function can thus effect a wide variety of physiological changes. Because of their biological significance, transporter proteins have been subjected to substantial scientific/commercial scrutiny (see, for example, U.S. application Ser. No. 08/805,118 filed Feb. 24, 1997, and No. 60/047,131 filed May 20, 1997, and U.S. Pat. Nos. 5,686,266, 5,882,926, and 5,618,677 which are herein incorporated by reference in their entirety).

The invention encompasses the use of the described NTP nucleotides, NTPs, peptides and fusions derived therefrom, as well as antibodies, preferably humanized monoclonal antibodies, or binding fragments, domains, or fusion proteins thereof, to the NTPs (which can, for example, act as NTP agonists or antagonists), antagonists that inhibit NTP activity or expression, or agonists that activate NTP activity or increase NTP expression, or can be used in the diagnosis and treatment of NTP-related diseases or disorders. Examples of such NTP-related diseases include, but are not limited to, seizures, mental illness, dementia, diabetes, Alzheimer's disease, depression, kidney disease, digestive/bowel disorders, high blood pressure, cardiopulmonary disease, infectious diseases, arrhythmia, and cancer.

In particular, the invention described in the subsections below encompasses NTPs, NTP polypeptides or peptides corresponding to functional domains of the NTPs (e.g., ECD, TM or CD), mutated, truncated or deleted forms of the NTPs (e.g., modified versions missing one or more functional domains or portions thereof, such as, ΔECD, ΔTM and/or ΔCD), NTP fusion proteins (e.g., an NTP or a functional domain of an NTP, such as an ECD, fused to an unrelated protein or peptide such as an immunoglobulin constant region, i.e., IgFc), nucleotide sequences encoding such products, and host cell expression systems that can produce such NTP products.

The invention also encompasses antibodies and anti-idiotypic antibodies (including Fab fragments), antagonists and agonists of the described NTPs, as well as compounds or nucleotide constructs that inhibit the expression of the NTP genes (transcription factor inhibitors, antisense and ribozyme molecules, or gene or regulatory sequence replacement constructs), or promote expression of NTPs (e.g., expression constructs in which NTP coding sequences are operatively associated with expression control elements such as promoters, promoter/enhancers, etc.). The invention also relates to host cells and animals genetically engineered to express the human NTPs (or mutant variants thereof) or to inhibit or "knock-out" expression of an animal's endogenous NTP gene. Another variation of the such knock-out animals includes "knock-in" animals where the endogenous copy of the animal gene has been replaced by related activity encoded by a sequence that is not native to the host animal (e.g., where a human ortholog has been used to replace the corresponding endogenous gene).

The described NTPs, or peptides therefrom, NTP fusion proteins, NTP nucleotide sequences, antibodies, antagonists and agonists can be useful for the detection of mutant NTPs or inappropriately expressed variants of the NTP for the diagnosis of NTP-related diseases or disorders. The NTPs, or peptides therefrom, NTP fusion proteins, NTP gene nucleotide sequences, host cell expression systems, antibodies, antagonists, agonists and genetically engineered cells and animals can also be used for screening for drugs (or high throughput screening of compound "libraries") effective in the treatment of the symptomatic or phenotypic manifestations of perturbing the normal function of a NTP in the body. The use of engineered host cells and/or animals may offer an advantage in that such systems allow not only for the identification of compounds that bind to an ECD of an NTP, but can also identify compounds that affect the activity of the NTP.

Finally, the NTP products (especially soluble derivatives such as peptides corresponding to the NTP ECD, or truncated polypeptides lacking one or more TM domains) and fusion protein products (especially NTP-Ig fusion proteins, i.e., fusions of an NTP, or a domain of an NTP, e.g., ECD, ΔTM to an IgFc), antibodies and anti-idiotypic antibodies (including Fab fragments), antagonists, or agonists can be used in the treatment of disease. For example, the administration of an effective amount of soluble NTP ECD, ΔTM, or an ECD-IgFc fusion protein or an anti-idiotypic antibody (or its Fab) that mimics the NTP ECD would "mop up" or "neutralize" NTP effector, modulatory, or activator, ligands, and prevent or reduce transporter expression and/or activity. Nucleotide constructs encoding such NTP products can be used to genetically engineer host cells to express such products in vivo; these genetically engineered cells function as "bioreactors" in the body delivering a continuous supply of an NTP, a NTP peptide, soluble ECD or ΔTM or a NTP fusion protein that can either enhance NTP activity or inhibit NTP activity. Nucleotide constructs encoding a functional NTP, mutant NTP variants, as well as antisense and ribozyme molecules can thus be used in "gene therapy" approaches for the modulation of NTP expression. Thus, the invention also encompasses pharmaceutical formulations and methods for treating biological disorders that comprise one or more of the described NTP genes or products. Suitable vectors/systems for such gene therapy or gene delivery applications include, but are not limited to, retrovirus, lentivirus, SIV, HIV, adenovirus, adeno-associated virus, lipid associated (and particularly cationic lipid associated) polynucleotide preparations, micro carrier beads or lattices, herpes virus vectors, hepatitis virus vectors, polynucleotide-containing emulsions, formulations containing "naked" DNA, etc.

Various aspects of the invention are described in greater detail in the subsections below.

5.1 The NTP Genes

The cDNA sequences and deduced amino acid sequences of the presently described human NTPs are presented in the Sequence Listing. SEQ ID NOS: 1–24 describe variants of a novel human transporter protein that is expressed in placenta, brain, cerebellum, spinal cord, testis, prostate. Northern analysis reveals a major transcript of approximately 3,2 kb and a minor transcript of about 5 kb in length. cDNAs used for sequencing were isolated from a testis cDNA library. Homology studies using SEQ ID NOS: 1–24 indicated that the described molecules share substantial similarity with, inter alia, sodium-dependent sulphate cotransporter proteins and sodium/dicarboxylates cotransporter proteins.

SEQ ID NOS: 25–32 describe variants of a novel human transporter protein that is expressed in brain, cerebellum, spinal cord, adrenal gland, pituitary, testis, stomach, and small intestine. Northern analysis reveals a major transcript (in brain and spinal cord) of approximately 10 kb and possible minor transcripts of about 3.1 and 5 kb in length. cDNAs used for sequencing were isolated from a kidney cDNA library.

Homology studies using SEQ ID NOS: 25–32 indicated that the described molecules share substantial similarity with, inter alia, amino acid transporter proteins and particularly cationic amino acid transporter proteins.

The NTPs of the present invention include: (a) the human DNA sequences presented in the Sequence Listing and additionally contemplate any nucleotide sequences encoding a contiguous and functional NTP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3)

and encodes a functionally equivalent gene product. Additionally contemplated are any nucleotide sequences that hybridize to the complement of the DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet which still encode a functionally equivalent NTP product. Functional equivalents of NTPs include naturally occurring NTPs present in other species, and mutant NTPs whether naturally occurring or engineered. The invention also includes degenerate variants of the disclosed sequence.

The invention also includes nucleic acid molecules, preferably DNA molecules, that hybridize to, and are therefore the complements of, the described NTP gene sequences. Such hybridization conditions may be highly stringent or less highly stringent, as described above. In instances wherein the nucleic acid molecules are deoxyoligonucleotides ("DNA oligos"), such molecules are typically about 16 to about 100 bases long, about 20 to about 80 bases long or about 34 to about 45 bases long, or any variation or combination of sizes represented therein and which incorporate a contiguous region of sequence first disclosed in the Sequence Listing. The described oligonucleotides can be used in conjunction with the polymerase chain reaction (PCR) to screen libraries, isolate clones, and prepare cloning and sequencing templates, etc.. Alternatively, the oligonucleotides can be used as hybridization probes. For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NTP antisense molecules, useful, for example, in NTP gene regulation (and/or as antisense primers in amplification reactions of NTP gene nucleic acid sequences). With respect to NTP gene regulation, such techniques can be used to regulate the biological functions affected by the described NTPs. Further, such sequences may be used as part of ribozyme and/or triple helix sequences that are also useful for NTP gene regulation.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NTP nucleotide probes can be used to screen a human genomic library using appropriately stringent conditions or by PCR. The identification and characterization of human genomic clones is helpful for identifying polymorphisms, determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NTP gene homolog may be isolated from nucleic acid from the organism of interest by performing PCR using two degenerate oligonucleotide primer pools designed on the basis of amino acid sequences within a NTP product disclosed herein. The template for the reaction may be total RNA, mRNA, and/or cDNA obtained by reverse transcription of mRNA prepared from, for example, human or non-human cell lines or tissue that are known or suspected to express a NTP gene.

The PCR product can be subcloned and sequenced to ensure that the amplified sequences represent the sequence of the desired NTP gene. The PCR fragment may then be used to isolate a full length cDNA clone by a variety of methods. For example, the amplified fragment may be labeled and used to screen a cDNA library such as a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express a NTP gene, such as, for example, brain tissue). A reverse transcription (RT) reaction may be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment may easily be isolated. For a review of cloning strategies which may be used, see e.g., Sambrook et al., 1989, supra.

A cDNA of a mutant NTP gene may be isolated, for example, by using PCR. In this case, the first cDNA strand may be synthesized by hybridizing an oligo-dT oligonucleotide to mRNA isolated from tissue known or suspected to be expressed in an individual putatively carrying a mutant NTP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NTP allele to that of a corresponding normal NTP allele, the mutation(s) responsible for the loss or alteration of function of the mutant NTP product can be ascertained.

Alternatively, a genomic library can be constructed using DNA obtained from an individual suspected of or known to carry a mutant NTP allele, or a cDNA library can be constructed using RNA from a tissue known, or suspected, to express a mutant or alternatively spliced NTP allele. A normal NTP gene, or any suitable fragment thereof, can then be labeled and used as a probe to identify the corresponding mutant NTP allele in such libraries. Clones containing the mutant NTP gene sequences can then be purified and subjected to sequence analysis according to methods well known to those of skill in the art.

Additionally, an expression library can be constructed utilizing cDNA synthesized from, for example, RNA isolated from a tissue known, or suspected, to express a mutant NTP allele in an individual suspected of or known to carry such a mutant allele. In this manner, gene products made by the putatively mutant tissue may be expressed and screened using standard antibody screening techniques in conjunction with antibodies raised against a normal NTP product, as described, below, in Section 5.3. (For screening techniques, see, for example, Harlow, E. and Lane, eds., 1988, "Antibodies: A Laboratory Manual", Cold Spring Harbor Press, Cold Spring Harbor.)

Additionally, screening can be accomplished using labeled NTP fusion proteins, such as, for example, AP-NTP or NTP-AP fusion proteins. In cases where a NTP mutation results in an expressed gene product with altered function (e.g., as a result of a missense or a frameshift mutation), a polyclonal set of antibodies to a given NTP are likely to cross-react with the corresponding mutant NTP gene product. Library clones detected by their reaction with such labeled antibodies can be purified and subjected to sequence analysis according to methods well known to those of skill in the art.

The invention also encompasses nucleotide sequences that encode mutant NTPs, peptide fragments of a NTP, truncated NTPs, and NTP fusion proteins. These include, but are not limited to nucleotide sequences encoding mutant NTPs described in section 5.2 infra; polypeptides or peptides corresponding to one or more ECD, TM and/or CD domains of a NTP or any portions of such domains; truncated NTPs in which one or more of the domains are deleted, e.g., a soluble NTP lacking TM or both the TM and CD regions, or a truncated, nonfunctional NTP lacking all or a portion of, for example, a CD region. Nucleotides encoding fusion proteins may include, but are not limited to, full length NTP sequences, truncated NTPs, or nucleotides encoding peptide fragments of a NTP fused to an unrelated protein or peptide, such as for example, a transmembrane sequence, which anchors a NTP ECD to the cell membrane; an Ig Fc domain which increases the stability and half life of the resulting fusion protein (e.g., NTP-Ig) in the bloodstream; or an enzyme, fluorescent protein, luminescent protein which can be used as a marker.

The invention also encompasses (a) DNA vectors that contain any of the NTP coding sequence and/or the complements thereof (i.e., antisense); (b) DNA expression vectors that contain any portion of a NTP coding sequence operatively associated with a regulatory element that directs the expression of the coding sequence; and (c) genetically engineered host cells engineered to contain NTP coding sequences operatively associated with a regulatory element that directs the expression of the coding sequences in the host cell. As used herein, regulatory elements include, but are not limited to, inducible and non-inducible promoters, enhancers, operators and other elements known to those skilled in the art that drive and regulate expression. Such regulatory elements include, but are not limited to, the cytomegalovirus hCMV immediate early gene, regulatable, viral (particularly retroviral LTR promoters) the early or late promoters of SV40 adenovirus, the lac system, the trp system, the tac system, the trc system, the major operator and promoter regions of phage lambda, the control regions of fd coat protein, the promoter for 3-phosphoglycerate kinase (PGK), the promoters of acid phosphatase, and the promoters of the yeast α-mating factors.

5.2 NTP Products

NTPs, peptide fragments therefrom, mutated, truncated or deleted forms of NTPs and/or NTP fusion proteins can be prepared for a variety of uses, including but not limited to the generation of antibodies, as reagents in diagnostic assays, the identification of other cellular gene products related to, or that interact with, a NTP, as reagents in assays for screening for compounds that can be as pharmaceutical reagents useful in the therapeutic treatment of mental, biological, or medical disorders and diseases.

The Sequence Listing discloses the amino acid sequences encoded by the described NTP genes. The described NTPs have an initiator methionine in a DNA sequence context consistent with a translation initiation site, followed by a initiator codon.

The NTP sequences of the present invention include the nucleotide and amino acid sequences presented in the Sequence Listing as well as analogues and derivatives thereof. Further, corresponding NTP homologues from other species are encompassed by the invention. In fact, any NTP protein encoded by the NTP nucleotide sequences described in Section 5.1, above, are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequence presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequence (as well as such variants as biased by human codon usage frequency tables).

The invention also encompasses proteins that are functionally equivalent to a NTP encoded by the nucleotide sequence described in Section 5.1, as judged by any of a number of criteria, including but not limited to the ability to bind or transport a ligand of the NTP, the ability to effect an identical or complementary biological pathway, a change in cellular metabolism (e.g., ion flux, tyrosine phosphorylation, etc.), or to effect the same change in phenotype when the NTP equivalent is present in an appropriate cell type (such as the amelioration, prevention or delay of a biochemical, biophysical, or overt phenotype). Such functionally equivalent NTPs include but are not limited to additions or substitutions of amino acid residues within the amino acid sequence encoded by a NTP gene sequence described above, in Section 5.1, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to NTP DNA (using random mutagenesis techniques well known to those skilled in the art) and the resulting mutant NTPs tested for activity, site-directed mutations of a NTP coding sequence can be engineered (using site-directed mutagenesis techniques well known to those skilled in the art) to generate mutant NTPs with increased function, e.g., higher binding/transport affinity for the transporter substrate, or decreased function. One starting point for such analysis is by aligning the disclosed human sequences with corresponding gene/protein sequences from, for example, other mammals in order to identify amino acid sequences and motifs that are conserved between different species. Non-conservative changes can be engineered at variable positions to alter function, transporter activity, or both. Alternatively, where alteration of function is desired, deletion or non-conservative alterations of the conserved regions (i.e., identical amino acids) can be engineered. For example, deletion or non-conservative alterations (substitutions or insertions) of the various conserved transmembrane domains.

Other mutations to a NTP coding sequence can be made to generate NTPs that are better suited for expression, scale up, etc. in the host cells chosen. For example, cysteine residues can be deleted or substituted with another amino acid in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur in an ECD (N-X-S or N-X-T), and/or an amino acid deletion at the second position of any one or more such recognition sequences in an ECD will prevent glycosylation of the NTP at the modified tripeptide sequence. (See, e.g., Miyajima et al., 1986, EMBO J. 5(6):1193–1197).

Peptides corresponding to one or more domains of a NTP (e.g., ECD, TM, CD, etc.), truncated or deleted NTPs (e.g., a NTP in which a ECD, TM and/or CD, or any portion thereof, is deleted) as well as fusion proteins in which a full length NTP, NTP peptide, or truncated NTP is fused to an unrelated protein, are also within the scope of the invention, and can be designed on the basis of the presently disclosed NTP gene nucleotide and NTP amino acid sequences. Such fusion proteins include but are not limited to IgFc fusions which stabilize a NTP or peptide and prolong half-life in vivo; or fusions to any amino acid sequence that allows the fusion protein to be anchored to the cell membrane, allowing an ECD to be exhibited on the cell surface; or fusions to an enzyme, fluorescent protein, or luminescent protein which provide a marker function.

While a NTP, and corresponding peptides, can be chemically synthesized (e.g., see Creighton, 1983, Proteins: Structures and Molecular Principles, W.H. Freeman & Co., N.Y.), large polypeptides derived from a NTP and especially a full-length NTP product can be advantageously produced by recombinant DNA technology using techniques well known in the art for expressing proteins. Such methods can be used to construct expression vectors containing a NTP nucleotide sequence described in Section 5.1 and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA corresponding to all or a portion of a transcript encoded by a NTP gene sequence may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express a NTP gene nucleotide sequence of the invention. Where the NTP peptide or polypeptide is a soluble derivative (e.g., NTP peptides corresponding to an ECD; truncated or deleted NTP in which a TM and/or CD are deleted) the peptide or polypeptide can be recovered from the culture, i.e., from the host cell in cases where the NTP peptide or polypeptide is not secreted, and from the culture media in cases where the NTP peptide or polypeptide is secreted by the cells. However, such expression systems also encompass engineered host cells that express NTP, or a functional equivalent, in situ, i.e., anchored in the cell membrane. Purification or enrichment of NTP from such expression systems can be accomplished using appropriate detergents and lipid micelles and methods well known to those skilled in the art. However, such engineered host cells themselves may be used in situations where it is important not only to retain the structural and functional characteristics of a NTP, but to assess biological activity, e.g., in drug screening assays.

The expression systems that can be used for purposes of the invention include but are not limited to microorganisms such as bacteria (e.g., E. coli, B. subtilis) transformed with recombinant bacteriophage DNA, plasmid DNA or cosmid DNA expression vectors containing the NTP nucleotide sequence; yeast (e.g., Saccharomyces, Pichia) transformed with recombinant yeast expression vectors containing a NTP nucleotide sequence; insect cell systems infected with recombinant virus expression vectors (e.g., baculo virus) containing a NTP sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a NTP nucleotide sequence; or mammalian cell systems (e.g., COS, CHO, BHK, 293, 3T3, etc.) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NTP product to be expressed. For example, when a large quantity of such a protein is to be produced for the generation of pharmaceutical compositions comprising a NTP, or for raising antibodies to a NTP, or corresponding peptide, for example, vectors that direct the expression of high levels of fusion protein products that are readily purified may be desirable. Such vectors include, but are not limited, to the E. coli expression vector pUR278 (Ruther et al., 1983, EMBO J. 2:1791), in which a NTP gene coding sequence may be ligated into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, Autographa californica nuclear polyhidrosis virus (AcNPV) is used as a vector to express foreign genes. The virus grows in Spodoptera frugiperda cells. A NTP gene coding sequence may be cloned individually into non-essential regions (for example the polyhedrin gene) of the virus and placed under control of an AcNPV promoter (for example the polyhedrin promoter). Successful insertion of NTP gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, a nucleotide sequence from a NTP gene can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the NTP product in infected host cells (e.g., See Logan & Shenk, 1984, Proc. Natl. Acad. Sci. USA 81:3655–3659). Specific initiation signals can also be required for efficient translation of inserted NTP gene nucleotide sequences. These signals include the ATG initiation codon and adjacent sequences. In cases where an entire NTP gene or cDNA, including its own initiation codon and adjacent sequences, is inserted into the appropriate expression vector, no additional translational control signals may be needed. However, in cases where only a portion of a NTP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can have a variety of origins, both natural and synthetic. The efficiency of expression can be enhanced by the inclusion of appropriate transcription enhancer elements, transcription terminators, etc. (See Bittner et al., 1987, Methods in Enzymol. 153:516–544).

In addition, a host cell strain can be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, and WI38 cell lines.

For long-term, high-yield production of recombinant proteins, stable expression is preferred. For example, cell lines which stably express a NTP can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express a NTP product. Such engineered cell lines may be particularly useful in screening and evaluation of compounds that affect the endogenous activity of a NTP.

A number of selection systems can be used, including but not limited to the herpes simplex virus thymidine kinase (Wigler, et al., 1977, Cell 11:223), hypoxanthine-guanine phosphoribosyltransferase (Szybalski & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

NTP product(s) can also be expressed in transgenic animals. Animals of any species, including, but not limited to, worms, mice, rats, rabbits, guinea pigs, pigs, micro-pigs, birds, goats, dogs, cats, and non-human primates, e.g., baboons, monkeys, and chimpanzees may be used to generate NTP transgenic animals.

Any technique known in the art may be used to introduce a NTP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ line cells (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NTP TRANSGENE in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such cell type-specific activation will depend upon the particular cell type of interest, and will be apparent to those of skill in the art.

When it is desired that the NTP transgene be integrated into the chromosomal site of the endogenous NTP gene, gene targeting is preferred. Briefly, when such a technique is to be utilized, vectors containing some nucleotide sequences homologous to an endogenous NTP gene are designed for the purpose of integrating, via homologous recombination with chromosomal sequences, a mutagenic sequence into the targeted NTP gene that effectively disrupts the function of the endogenous gene (i.e., "knockout" cells and animals).

The transgene may also be selectively introduced into a particular cell type, thus inactivating an endogenous NTP gene in only that cell type, by following, for example, the teaching of Gu et al., 1994, Science, 265:103–106. The regulatory sequences required for such cell type specific inactivation will depend upon the particular cell type of interest, and will be apparent to those of skill in the art.

Once transgenic animals have been generated, the expression of a recombinant NTP gene can be assayed utilizing standard techniques. Initial screening may be accomplished by Southern blot analysis or PCR to analyze animal tissues to determine whether the transgene has integrated into the genome. The level of mRNA expression by the transgene in the tissues of the transgenic animals can also be assessed using techniques which include but are not limited to Northern blot analysis of tissue samples obtained from the animal, in situ hybridization analysis, and RT-PCR. Samples of NTP gene-expressing tissue, can also be evaluated immunocytochemically using antibodies specific for the NTP product of the transgene.

5.3 Antibodies to NTP Proteins

Antibodies that specifically recognize one or more epitopes of a NTP, or epitopes of conserved variants of a NTP, or peptide fragments of a NTP are also encompassed by the invention. Such antibodies include but are not limited to polyclonal antibodies, monoclonal antibodies (mAbs), human, humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention can be used, for example, in the detection of a NTP in a biological sample and can therefore be utilized as part of a diagnostic or prognostic technique whereby patients are tested for abnormal amounts of NTP expression or activity. Such antibodies may also be utilized in conjunction with, for example, compound screening schemes, as described, below, in Section 5.5, for the evaluation of the effect of test compounds on the expression and/or activity of a NTP product. Additionally, such antibodies can be used in conjunction with gene therapy to, for example, evaluate the expression of normal and/or engineered NTP by cells prior to their introduction into the patient. Such antibodies may additionally be used as a method for the inhibition of abnormal NTP activity. Thus, such antibodies can be utilized as part of treatment methods for NTP-involved biological disorders.

For the production of antibodies, various host animals can be immunized by injection with the NTP, a NTP peptide (e.g., one corresponding the a functional domain of the receptor, such as an ECD, TM or CD), truncated NTP polypeptides (NTP in which one or more domains, e.g., a TM or CD has been deleted, or a portion thereof), functional equivalents of the NTP or NTP mutants. Such host animals may include, but are not limited to, rabbits, goats, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies are homogeneous populations of antibodies that bind a particular antigen, and can be obtained by any technique which provides for the production of antibody molecules by, for example, cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention can be cultivated in vitro or in vivo. Production of high titers of mAbs in vivo makes this the presently preferred method of production.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al, U.S. Pat. No. 4,816397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by refer humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041–1043; Liu et al. (1987) *Proc. Natl. Acad Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison (1985) *Science* 229:1202–1207; Oi et al. (1986) *Bio/Techniques* 4:214; U.S. Pat. No. 5,225,539; Jones et al. (1986) *Nature* 321:552–525; Verhoeyan et al (1988) *Science* 239:1534; and Beidler et al. (1988) *J. Immunol.* 141:4053–4060.

Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immunol.* 13:65–93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. In addition, companies such as Abgenix, Inc. (Fremont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) *Bio/technology* 12:899–903).

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NTP products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to NTP can be utilized to generate anti-idiotypic antibodies that "mimic" NTP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NTP ECD and competitively inhibit the binding of a ligand or accessory molecule of a NTP and can thus be used to generate anti-idiotypes that "mimic" a NTP ECD and, therefore, bind and neutralize a ligand or a NTP accessory molecule. Such neutralizing anti-idiotypes or Fab fragments of such anti-idiotypic antibodies can be used in therapeutic regimens involving the regulation of NTP activity.

5.4 Diagnosis of Abnormalities Related to a NTP

A variety of methods can be employed for the diagnostic and prognostic evaluation of disorders related to NTP function, and for the identification of subjects having a predisposition to such disorders.

Such methods can, for example, utilize reagents such as a NTP nucleotide sequence described in Section 5.1, or a portion thereof, or NTP antibodies as described in Section 5.3. Specifically, such reagents can be used, for example, for: (1) the detection of the presence of NTP gene mutations, or the detection of either the over- or under-expression of NTP mRNA relative to a given phenotype; (2) the detection of either an over- or under-abundance of a NTP relative to a given phenotype; and (3) the detection of perturbations or abnormalities in the transporter function mediate by a NTP.

The methods described herein may be performed, for example, by utilizing pre-packaged diagnostic kits comprising at least one specific NTP nucleotide sequence or NTP antibody reagent described herein, which may be conveniently used, e.g., in clinical settings, to diagnose patients exhibiting biological abnormalities.

For the detection of NTP mutations, any nucleated cell can be used as a starting source for genomic nucleic acid. For the detection of NTP gene expression or NTP gene products, any cell type or tissue in which a NTP gene is expressed, such as, for example, brain cells, may be utilized.

Nucleic acid-based detection techniques are described, below, in Section 5.4.1. Peptide detection techniques are described, below, in Section 5.4.2.

5.4.1 Detection of NTP Genes and Transcripts

Mutations within a NTP gene can be detected using a number of techniques. Nucleic acid from any nucleated cell can be used as the starting point for such assay techniques, and may be isolated according to standard nucleic acid preparation procedures which are well known to those of skill in the art.

DNA can be used in hybridization or amplification assays of biological samples to detect abnormalities involving NTP gene structure, including point mutations, insertions, deletions and chromosomal rearrangements. Such assays may include, but are not limited to, Southern analyses, single stranded conformational polymorphism analyses (SSCP), and PCR analyses.

Such diagnostic methods for the detection of NTP gene specific mutations can involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described in Section 5.1, under conditions favorable for the specific annealing of these reagents to their complementary sequences within the NTP gene. Preferably, the lengths of these nucleic acid reagents are at least 15 to 30 nucleotides. After incubation, all non-annealed nucleic acids are removed from the nucleic acid:NTP gene hybrid. The presence of nucleic acids which have hybridized, if any such molecules exist, is then detected. Using such a detection scheme, the nucleic acid from the cell type or tissue of interest can be immobilized, for example, to a solid support such as a membrane, gene "chip" substrate, or a plastic surface such as that on a microtiter plate or polystyrene beads. In this case, after incubation, non-annealed, labeled nucleic acid reagents of the type described in Section 5.1 are easily removed. Detection of the remaining, annealed, labeled NTP nucleic acid reagents is accomplished using standard techniques well-known to those in the art. The NTP gene sequence(s) to which the nucleic acid reagents have annealed can be compared to the annealing pattern expected from a normal NTP gene sequence in order to determine whether a NTP gene mutation is present.

Alternative diagnostic methods for the detection of NTP gene specific nucleic acid molecules, in patient samples or other appropriate cell sources, may involve their amplification, e.g., by PCR (the experimental embodiment set forth in Mullis, K. B., 1987, U.S. Pat. No. 4,683,202), followed by the detection of the amplified molecules using techniques well known to those of skill in the art. The resulting amplified sequences can be compared to those which would be expected if the nucleic acid being amplified contained only normal copies of a NTP gene in order to determine whether a NTP gene mutation exists.

Additionally, well-known genotyping techniques can be performed to identify individuals carrying NTP gene mutations. Such techniques include, for example, the use of restriction fragment length polymorphisms (RFLPs), which involve sequence variations in one of the recognition sites for the specific restriction enzyme used.

Additionally, improved methods for analyzing DNA polymorphisms that can be utilized for the identification of NTP gene mutations have been described that capitalize on the presence of variable numbers of short, tandemly repeated DNA sequences between the restriction enzyme sites. For example, Weber (U.S. Pat. No. 5,075,217, which is incorporated herein by reference in its entirety) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers which are so closely spaced exhibit a high frequency co-inheritance, and are extremely useful in the identification of genetic mutations, such as, for example, mutations within the NTP gene, and the diagnosis of diseases and disorders related to such NTP mutations.

Also, Caskey et al. (U.S. Pat. No. 5,364,759, which is incorporated herein by reference in its entirety) describe a DNA profiling assay for detecting short tri and tetra nucleotide repeat sequences. The process includes extracting the DNA of interest, such as the NTP gene, amplifying the extracted DNA, and labeling the repeat sequences to form a genotypic map of the individual's DNA.

The level of NTP gene expression can also be assayed by detecting and measuring NTP transcription. For example, RNA from a cell type or tissue known, or suspected to express a NTP gene, such as brain, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of a NTP gene. Such analyses may reveal both quantitative and qualitative aspects of the expression pattern of a NTP gene, including activation or inactivation of NTP gene expression.

In one embodiment of such a detection scheme, cDNAs are synthesized from the RNAs of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the NTP gene nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining, by utilizing any other suitable nucleic acid staining method, or by sequencing.

Additionally, it is possible to perform such NTP gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (See, for example, Nuovo, G. J., 1992, "PCR In Situ Hybridization: Protocols And Applications", Raven Press, N.Y.).

Alternatively, if a sufficient quantity of the appropriate cells can be obtained, standard Northern analysis can be performed to determine the level of mRNA expression of a NTP gene.

5.4.2 Detection of NTP Products

Antibodies directed against wild type or mutant NTPs or variants or peptide fragments thereof, that are discussed, above in Section 5.3, can also be used as diagnostics and prognostics, as described herein. Such diagnostic methods, can be used to detect abnormalities in the level of NTP gene expression, or abnormalities in the structure and/or temporal, tissue, cellular, or subcellular location of a NTP, and can be performed in vivo or in vitro, such as, for example, on biopsy tissue.

Additionally, antibodies directed to epitopes of a NTP ECD can be used in vivo to detect the pattern and level of expression of a NTP in the body. Such antibodies can be labeled, e.g., with a radio-opaque or other appropriate compound and injected into a subject in order to visualize binding to a NTP expressed in the body using methods such as X-rays, CAT-scans, or MRI. Labeled antibody fragments, e.g., the Fab or single chain antibody comprising the smallest portion of the antigen binding region, are preferred for this purpose to promote crossing the blood-brain barrier and permit labeling of NTPs expressed in the brain.

Additionally, any NTP fusion protein or NTP conjugated protein whose presence can be detected, can be administered. For example, NTP fusion or conjugated proteins labeled with a radio-opaque or other appropriate compound can be administered and visualized in vivo, as discussed, above for labeled antibodies. Further, such NTP fusion proteins as AP-NTP on NTP-Ap fusion proteins can be utilized for in vitro diagnostic procedures.

Alternatively, immunoassays or fusion protein detection assays, as described above, can be utilized on biopsy and autopsy samples in vitro to permit assessment of the expression pattern of a NTP. Such assays are not confined to the use of antibodies that define a NTP ECD, but can include the use of antibodies directed to epitopes of any of the domains of a NTP, e.g., a ECD, a TM and/or CD. The use of each or all of these labeled antibodies will yield useful information regarding translation and intracellular transport of a NTP to the cell surface, and can identify defects in processing.

The tissue or cell type to be analyzed will generally include those which are known, or suspected, to express a NTP gene, such as, for example, brain cells. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of a NTP gene.

For example, antibodies, or fragments of antibodies, such as those described, above, in Section 5.3, useful in the present invention may be used to quantitatively or qualitatively detect the presence of NTPs or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred if such NTP gene products are expressed on the cell surface.

The antibodies (or fragments thereof) or NTP fusion or conjugated proteins useful in the present invention may, additionally, be employed histologically, as in immunofluorescence, immunoelectron microscopy or non-immuno assays, for in situ detection of NTPs or conserved variants or peptide fragments thereof, or for NTP binding studies (in the case of labeled fusion proteins incorporating NTP accessory proteins).

In situ detection may be accomplished by removing a histological specimen from a patient, and applying thereto a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of a NTP, or conserved variants or peptide fragments, or NTP binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for NTPs or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying a NTP or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled NTP antibody or NTP ligand fusion protein. The solid phase support may then be washed with the buffer a second time to remove unbound antibody or fusion protein. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of NTP antibody or NTP ligand fusion protein may be determined according to well known methods. Those skilled in the art will be able to determine operative and optimal assay conditions for each determination by employing routine experimentation.

With respect to antibodies, one of the ways in which a NTP antibody can be detectably labeled is by linking it to an enzyme that can be used in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme that is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect NTPs through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.5 Screening Assays for Compounds that Modulate NTP Expression or Activity

The following assays are designed to identify compounds that interact with (e.g., bind to) a NTP (including, but not limited to an ECD or CD of a NTP), compounds that interact with (e.g., bind to) intracellular proteins that interact with a NTP (including but not limited to the TM and CD of a NTP), compounds that interfere with the interaction of a NTP with transmembrane or intracellular proteins, or such proteins that may be present in cellular organelles, that are associated with NTP-mediated transport, and to compounds that modulate the activity of a NTP gene (i.e., modulate the level of NTP gene expression) or modulate the quantity of a NTP in the cell. Assays may additionally be utilized that identify compounds that bind to NTP gene regulatory sequences (e.g., promoter sequences) and which may modulate NTP gene expression. See e.g., Platt, K. A., 1994, J. Biol. Chem. 269:28558–28562, which is incorporated herein by reference in its entirety.

The compounds that can be screened in accordance with the invention include but are not limited to peptides, antibodies and fragments thereof, and other organic compounds (e.g., peptidomimetics) that bind to an ECD, or a corresponding nontransmembrane domain of a organelle or nuclear membrane (in the case where the NTP is associated with an intracellular membrane) of the described NTP and either facilitates or inhibits NTP activity; as well as peptides, antibodies or fragments thereof, and other organic compounds that mimic a domain of a NTP (or a portion thereof) and bind to and "neutralize" NTP accessory proteins.

Such compounds may include, but are not limited to, peptides such as, for example, soluble peptides, including but not limited to members of random peptide libraries; (see, e.g., Lam, K. S. et al., 1991, Nature 354:82–84; Houghten, R. et al., 1991, Nature 354:84–86), and combinatorial chemistry-derived molecular library made of D- and/or L-configuration amino acids, phosphopeptides (including, but not limited to members of random or partially degenerate, directed phosphopeptide libraries; see, e.g., Songyang, Z. et al., 1993, Cell 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Other compounds that can be screened in accordance with the invention include but are not limited to small organic molecules that are able to cross the blood-brain barrier, gain entry into an appropriate cell (e.g., in the choroid plexus, the hypothalamus, etc.) and affect the expression of a NTP gene or some other gene involved in a NTP-mediated transport mechanism (e.g., by interacting with the regulatory region or transcription factors involved in NTP gene expression); or such compounds that affect the activity of a NTP (e.g., by inhibiting or enhancing the activity of the NTP) or the activity of some other intracellular factor associated with NTP activity.

Computer modeling and searching technologies permit identification of compounds, or the improvement of already identified compounds, that can modulate NTP expression or activity. Having identified such a compound or composition, the active sites or regions are identified. Such active sites might typically be ligand binding sites. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential NTP modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active regions of a NTP, and related transport accessory factors will be apparent to those of skill in the art.

Examples of molecular modeling systems are the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988, Acta Pharmaceutical Fennica 97:159–166; Ripka, New Scientist 54–57 (Jun. 16, 1988); McKinaly and Rossmann, 1989, Annu. Rev. Pharmacol. Toxiciol. 29:111–122; Perry and Davies, OSAR: Quantitative Structure-Activity Relationships in Drug Design pp. 189–193 (Alan R. Liss, Inc. 1989); Lewis and Dean, 1989 Proc. R. Soc. Lond. 236:125–140 and 141–162; and, with respect to a model receptor for nucleic acid components, Askew, et al, 1989, J. Am. Chem. Soc. 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Cell-based systems can also be used to identify compounds that bind one of the described NTPs as well as assess the altered activity associated with such binding in living cells. One tool of particular interest for such assays is green fluorescent protein which is described, inter alia, in U.S. Pat. No. 5,625,048, herein incorporated by reference. Cells that may be used in such cellular assays include, but are not limited to, leukocytes, or cell lines derived from leukocytes, lymphocytes, stem cells, including embryonic stem cells, and the like. In addition, expression host cells (e.g., B95 cells, COS cells, CHO cells, OMK cells, fibroblasts, Sf9 cells) genetically engineered to express functional NTP and to respond to activation by the test, or natural, ligand, as measured by a chemical or phenotypic change, or induction of another host cell gene, can be used as an end point in the assay.

5.5.1 In Vitro Screening Assays for Compounds that Blind to NTPs

In vitro systems may be designed to identify compounds capable of interacting with (e.g., binding to) the described NTPs (including, but not limited to, a ECD or CD of a NTP). Compounds identified may be useful, for example, in modulating the activity of wild type and/or mutant NTP products; may be useful in elaborating the biological function of a NTP; may be utilized in screens for identifying compounds that disrupt normal NTP functions or interactions; or may in themselves disrupt such interactions.

The principle of the assays used to identify compounds that bind to or interact with a NTP involves preparing a reaction mixture of a NTP and a test compound under conditions and for a time sufficient to allow the two components to interact and bind, thus forming a complex which can be removed and/or detected in the reaction mixture. The NTP species used can vary depending upon the goal of the screening assay. For such applications, one can use a full length NTP, or a soluble truncated NTP, e.g., in which the TM and/or CD is deleted from the molecule, a peptide corresponding to a ECD or a fusion protein containing one or more NTP ECD(s) fused to a protein or polypeptide that affords advantages in the assay system (e.g., labeling, isolation of the resulting complex, etc.) can be utilized. Where compounds that interact with the cytoplasmic domain are sought to be identified, peptides corresponding to a NTP CD and fusion proteins containing a NTP CD can be used.

The screening assays can be conducted in a variety of ways. For example, one method to conduct such an assay would involve anchoring a NTP, NTP polypeptide, peptide or fusion protein, or even the test substance onto a solid phase and detecting NTP/test compound complexes anchored on the solid phase at the end of the reaction. In one embodiment of such a method, the NTP reactant can be anchored onto a solid surface, and the test compound, which is not anchored, may be labeled, either directly or indirectly.

In practice, microtiter plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for a NTP, NTP polypeptide, peptide or fusion protein or the test compound to anchor any complexes formed in solution, and a labeled antibody specific for the other component of the possible complex to detect anchored complexes.

Alternatively, cell-based assays can be used to identify compounds that interact with NTPs. To this end, cell lines that express a NTP, or cell lines (e.g., COS cells, CHO cells, fibroblasts, etc.) that have been genetically engineered to express a NTP (e.g., by transfection or transduction of NTP gene DNA) can be used. Interaction of the test compound with, for example, an ECD from a NTP expressed by the host cell can be determined by comparison or competition with native ligand.

5.5.2 Assays for Intracellular Proteins that Interact with NTPs

Any method suitable for detecting protein-protein interactions may be employed for identifying transmembrane proteins or intracellular proteins that interact with the described NTPs. Among the traditional methods which can be employed are co-immunoprecipitation, crosslinking and co-purification through gradients or chromatographic columns of cell lysates or proteins obtained from cell lysates to identify proteins in the lysate that interact with a NTP. For these assays, the NTP component used can be a full length NTP, a soluble derivative lacking the membrane-anchoring region (e.g., a truncated NTP in which a TM is deleted resulting in a truncated molecule containing a ECD fused to a CD), a peptide corresponding to a CD or a fusion protein containing a CD from the described NTP. Once isolated, such an intracellular protein can be identified and can, in turn, be used, in conjunction with standard techniques, to identify proteins with which it interacts. For example, at least a portion of the amino acid sequence of an intracellular protein that interacts with a NTP can be ascertained using techniques well known to those of skill in the art, such as via the Edman degradation technique. (See, e.g., Creighton, 1983, "Proteins: Structures and Molecular Principles", W.H. Freeman & Co., N.Y., pp.34–49). The amino acid sequence obtained can be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well-known. (See, e.g., Ausubel, supra, and PCR Protocols: A Guide to Methods and Applications, 1990, Innis, M. et al., eds. Academic Press, Inc., New York).

Additionally, methods may be employed which result in the simultaneous identification of genes which encode the transmembrane or intracellular proteins interacting with a NTP. These methods include, for example, probing expression, libraries, in a manner similar to the well known technique of antibody probing of λgt11 libraries, using labeled NTPs, or a NTP polypeptide, peptide or fusion protein, e.g., a NTP polypeptide or a NTP domain fused to a marker (e.g., an enzyme, fluor, luminescent protein, or dye), or an Ig-Fc domain.

One method that detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to nucleotide sequence encoding a NTP, or a NTP polypeptide, peptide or fusion protein, and the other plasmid includes nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, a NTP may be used as the bait gene product. Total genomic or cDNA sequences are fused to the DNA encoding an activation domain. This library and a plasmid encoding a hybrid of the bait NTP product fused to the DNA-binding domain are cotransformed into a yeast reporter strain, and the resulting transformants are screened for those that express the reporter gene. For example, and not by way of limitation, a bait NTP gene sequence, such as the open reading frame of the NTP (or a domain of the NTP) can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait NTP product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait NTP gene-GAL4 fusion plasmid into a yeast strain which contains a lacZ gene driven by a promoter which contains GAL4 activation sequence. A cDNA encoded protein, fused to GAL4 transcriptional activation domain, that interacts with a bait NTP product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait NTP gene-interacting protein using techniques routinely practiced in the art.

5.5.3 Assays for Compounds that Interfere with NTP/Intracellular or NTP/Membrane Macromolecule Interactions The macromolecules that interact with a NTP are referred to, for purposes of this discussion, as "binding partners". These binding partners are likely to be involved in NTP-mediated transport. Therefore, it is desirable to identify compounds that interfere with or disrupt the interaction of such binding partners that can be useful in regulating the activity of NTP and controlling disorders associated with NTP activity.

The basic principle of the assay systems used to identify compounds that interfere with the interaction between NTP and any binding partner or partners involves preparing a reaction mixture containing a NTP, NTP polypeptide, peptide or fusion protein as described in Sections 5.5.1 and 5.5.2 above, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the NTP moiety and its binding partner. Control reaction mixtures are incubated without the test compound or with a placebo. The formation of any complexes between the NTP moiety and the binding partner is then detected. The formation of a complex in the control reaction, but not in the reaction mixture containing the test compound, indicates that the compound interferes with the interaction of the NTP and the interactive binding partner. Additionally, complex formation within reaction mixtures containing the test compound and normal NTP may also be compared to complex formation within reaction mixtures containing the test compound and a mutant NTP. This comparison may be important in those cases wherein it is desirable to identify compounds that specifically disrupt interactions of mutant, or mutated, NTPs but not normal NTPs.

The assay for compounds that interfere with the interaction of the described NTP and binding partners can be conducted in a heterogeneous or homogeneous format. Heterogeneous assays involve anchoring either the NTP moiety product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to, or simultaneously with, the NTP moiety and interactive binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the NTP moiety or an interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of NTP product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of a NTP moiety and an interactive binding partner is prepared in which either the NTP or its binding partners is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt NTP/binding partner interaction can be identified.

In a particular embodiment, a NTP fusion can be prepared for immobilization. For example, a NTP or a peptide fragment, e.g., corresponding to a CD, can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody using methods routinely practiced in the art and described above, in Section 5.3. This antibody can be labeled with the radioactive isotope $^{125}$I, for example, by methods routinely practiced in the art. In a heterogeneous assay, e.g., the GST-NTP fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the NTP product and the interactive binding partner can be detected by measuring the amount of radioactivity that remains associated with the glutathione-agarose beads. A successful inhibition of the interaction by the test compound will result in a decrease in measured radioactivity.

Alternatively, the GST-NTP fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the NTP/binding partner interaction can be detected by adding the labeled antibody and measuring the radioactivity associated with the beads.

In another embodiment of the invention, these same techniques can be employed using peptide fragments that correspond to the binding domains of a NTP and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensatory mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a relatively short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, a NTP product can be anchored to a solid material as described, above, by making a GST-NTP fusion protein and allowing it to bind to glutathione agarose beads. The interactive binding partner can be labeled with a radioactive isotope, such as $^{35}S$, and cleaved with a proteolytic enzyme such as trypsin. Cleavage products can then be added to the anchored GST-NTP fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

5.6 Modulatory, Antisense, Ribozyme and Triple Helix Approaches

In another embodiment, the levels of NTP gene regulation can be reduced by using well-known antisense, gene "knock-out," ribozyme and/or triple helix methods. Such molecules may be designed to modulate, reduce or inhibit either unimpaired, or if appropriate, mutant sequence activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides which are complementary to an mRNA sequence. The antisense oligonucleotides will bind to the complementary mRNA sequence transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the sequence of interest could be used in an antisense approach to inhibit translation of endogenous mRNA. Antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit mRNA expression. It is preferred that these studies utilize controls that distinguish between antisense gene inhibition and non-specific biological effects of oligonucleotides. Additionally, it is envisioned that results obtained using the antisense oligonucleotide are compared with those obtained using a control oligonucleotide. It is preferred that the control oligonucleotide is of approximately the same length as the test oligonucleotide and that the nucleic acid of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, *Proc. Natl. Acad. Sci. U.S.A.* 86:6553–6556; Lemaitre, et al., 1987, *Proc. Natl Acad. Sci. U.S.A.* 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, *BioTechniques* 6:958–976) or intercalating agents (see, e.g., Zon, 1988, *Pharm. Res.* 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987, *Nucl. Acids Res.* 15:6625–6641). The oligonucleotide is a 2'-0-methylribonucleotide (Inoue, et al., 1987, *Nucl. Acids Res.* 15:6131–6148), or a chimeric RNA-DNA analogue (Inoue, et al., 1987, *FEBS Lett.* 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, *Nucl. Acids Res.* 16:3209), methylphosphonate oligonucleotides can be prepared by use of controlled pore glass polymer supports (Sarin, et al., 1988, *Proc. Natl. Acad. Sci. U.S.A.* 85:7448–7451), etc.

While antisense nucleotides complementary to a coding region sequence could be used, those complementary to the transcribed, untranslated region are most preferred.

Antisense molecules should be delivered to cells that express the sequence in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies which specifically bind receptors or antigens expressed on the target cell surface) can be administered systemically.

A preferred approach to achieve intracellular concentrations of the antisense sufficient to suppress translation of endogenous mRNAs utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs which will form complementary base pairs with the endogenous sequence transcripts and thereby prevent translation of the mRNA sequence. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, *Nature* 290:304–310), the promoter contained in the 3'-long terminal repeat of Rous sarcoma virus (Yamamoto, et al., 1980, *Cell* 22:787–797), the herpes thymidine kinase promoter (Wagner, et al., 1981, *Proc. Natl. Acad. Sci. USA.* 78:1441–1445), the regulatory sequences of the metallothionein gene (Brinster, et al., 1982, *Nature* 296:39–42), etc. Any type of plasmid, cosmid, YAC or viral vector can be used to prepare the recombinant DNA construct that can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver, et al., 1990, *Science* 247, 1222–1225).

Ribozymes are enzymatic RNA molecules capable of catalyzing the specific cleavage of RNA. (For a review, see Rossi, 1994, *Current Biology* 4:469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions which form complementary base pairs with the target mRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology: A Comprehensive Desk Reference*, VCH Publishers, New York, (see especially FIG. 4, page 833) and in Haseloff and Gerlach, 1988, *Nature,* 334:585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, *Science,* 224:574–578; Zaug and Cech, 1986, *Science,* 231:470–475; Zaug, et al., 1986, *Nature,* 324:429–433; published International patent application No. WO 88/04300 by University Patents Inc.; Been and Cech, 1986, *Cell,* 47:207–216). The Cech-type ribozymes have an eight base pair active site that hybridizes to a target RNA sequence whereafter cleavage of the target RNA takes place. The invention encompasses those Cech-type ribozymes that target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes, unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, *Nature* 317:230–234; Thomas and Capecchi, 1987, *Cell* 51:503–512; Thompson, et al., 1989, *Cell* 5:313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells which express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures which prevent transcription of the target gene in target cells in the body. (See generally, Helene, 1991, *Anticancer Drug Des.,* 6(6):569–584; Helene, et al., 1992, *Ann. N.Y Acad. Sci.,* 60:27–36; and Maher, 1992, *Bioassays* 14(12):807–815).

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizable stretches of either purines or pyrimidines to be present on one strand of a duplex. Nucleic acids may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen which are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles which the possibility may arise wherein the concentration of normal target gene product present may be lower than is necessary for a normal phenotype. In such cases, to ensure that substantially normal levels of target gene activity are maintained, therefore, nucleic acid molecules which encode and express target gene polypeptides exhibiting normal target gene activity may, be introduced into cells via gene therapy methods such as those described, below, which do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid-phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.6.1 Gene Replacement Therapy

An alternative means for employing the presently disclosed NTP agents includes the use of vectors to directly insert genes encoding the agents into target cells (e.g., gene therapy).

The nucleic acid sequences can be utilized for transferring recombinant nucleic acid sequences to cells and expressing said sequences in recipient cells. Such techniques can be used, for example, in marking cells or for the treatment of a condition, disorder, or disease. Such treatment can be in the form of gene replacement therapy. Specifically, one or more copies of a normal sequence or a portion of the sequence which directs the production of a sequence product exhibiting normal sequence function, may be inserted into the appropriate cells within a patient, using vectors which include, but are not limited to adenovirus, adeno-associated virus and retrovirus vectors, in addition to other particles which introduce DNA into cells, such as liposomes.

In another embodiment, techniques for delivery involve direct administration, e.g., by stereotactic delivery of such sequences to the site of the cells in which the sequences are to be expressed.

Methods for introducing genes for expression in mammalian cells are well known in the field. Generally, for such gene therapy methods, the nucleic acid is directly administered in vivo into a target cell or a transgenic mouse that expresses SP-10 promoter operably linked to a reporter gene. This can be accomplished by any methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), by direct injection of naked DNA, by use of microparticle bombardment (e.g., a gene gun; Biolistic, Dupont), by coating with lipids or cell-surface receptors or transfecting agents, by encapsulation in liposomes, microparticles, or microcapsules, by administering it in linkage to a peptide which is known to enter the nucleus, or by administering it in linkage to a ligand subject to receptor-mediated endocytosis (see e.g., Wu and Wu, 1987, J. Biol. Chem. 262:4429–4432), which can be used to target cell types specifically expressing the receptors. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992; WO 92/22635 dated Dec. 23, 1992; WO92/20316 dated Nov. 26, 1992; WO93/14188 dated Jul. 22, 1993; WO 93/20221 dated Oct. 14, 1993).

Additional methods which may be utilized to increase the overall level of expression of sequences of the invention include using targeted homologous recombination methods, discussed, above, to modify the expression characteristics of an endogenous sequence in a cell or microorganism by inserting a heterologous DNA regulatory element such that the inserted regulatory element is operatively linked with the endogenous sequence in question. Targeted homologous recombination can thus be used to activate transcription of an endogenous sequence which is "transcriptionally silent", i.e., is not normally expressed or is normally expressed at very low levels, or to enhance the expression of an endogenous sequence which is normally expressed.

Further, the overall level of expression of sequences may be increased by the introduction of appropriate sequence-expressing cells, preferably autologous cells, into a patient at positions and in numbers which are sufficient to ameliorate the symptoms of a condition, disorder, or disease involving NTPs. Such cells may be either recombinant or non-recombinant.

Among the cells that can be administered to increase the overall level of sequence expression in a patient are normal cells which express the sequence. Alternatively, cells, preferably autologous cells, can be engineered to express the sequences, and may then be introduced into a patient in positions appropriate for the amelioration of the symptoms of a condition, disorder, or disease involving NTPs.

When the cells to be administered are non-autologous cells, they can be administered using well-known techniques that prevent a host immune response against the introduced cells from developing. For example, the cells may be introduced in an encapsulated form that, while allowing for an exchange of components with the immediate extracellular environment, does not allow the introduced cells to be recognized by the host immune system.

5.7 Pharmaceutical Formulations and Methods of Administration

The compounds of this invention can be formulated and administered to inhibit a variety of disease states by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a therapeutically effective amount of the compound sufficient to result in amelioration of symptoms of the disease and will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired.

Preferably, agents that modulate NTP function shall be substantially specific. For the purposes of the present invention, the term substantially specific shall mean that a given agent is capable of being dosaged to provide the desired effect while not causing undue cellular toxicity.

One of ordinary skill will appreciate that, from a medical practitioner's or patient's perspective, virtually any alleviation or prevention of an undesirable symptom (e.g., symptoms related to disease, sensitivity to environmental factors, normal aging, and the like) would be desirable. Thus, for the purposes of this Application, the terms "treatment", "therapeutic use", or "medicinal use" used herein shall refer to any and all uses of compositions comprising the claimed agents which remedy a disease state or symptoms, or otherwise prevent, hinder, retard, or reverse the progression of disease or other undesirable symptoms in any way whatsoever.

When used in the therapeutic treatment of disease, an appropriate dosage of presently described agents, or derivatives thereof, may be determined by any of several well established methodologies. For instance, animal studies are commonly used to determine the maximal tolerable dose, or MTD, of bioactive agent per kilogram weight. In general, at least one of the animal species tested is mammalian. Those skilled in the art regularly extrapolate doses for efficacy and avoiding toxicity to other species, including human. Before human studies of efficacy are undertaken, Phase I clinical studies in normal subjects help establish safe doses.

Additionally, the bioactive agents may be complexed with a variety of well established compounds or structures that, for instance, enhance the stability of the bioactive agent, or otherwise enhance its pharmacological properties (e.g., increase in vivo half-life, reduce toxicity, etc.).

5.7.1 Dose Determinations

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Specific dosages may also be utilized for antibodies. Typically, the preferred dosage is 0.1 mg/kg to 100 mg/kg of body weight (generally 10 mg/kg to 20 mg/kg), and if the antibody is to act in the brain, a dosage of 50 mg/kg to 100 mg/kg is usually appropriate. If the antibody is partially human or fully human, it generally will have a longer half-life within the human body than other antibodies. Accordingly, lower dosages of partially human and fully human antibodies is often possible. Additional modifications may be used to further stabilize antibodies. For example, lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

A therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

Moreover, treatment of a subject with a therapeutically effective amount of a protein, polypeptide or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5 or 6 weeks.

The present invention further encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors known to those or ordinary skill in the art, e.g., a physician. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram.

5.7.2 Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in *Remington's Pharmaceutical Sciences*, a standard reference text in this field.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Another aspect of the present invention includes formulations that provide for the sustained release of NTP antagonists. Examples of such sustained release formulations include composites of biocompatible polymers, such as poly(lactic acid), poly(lactic-co-glycolic acid), methylcellulose, hyaluronic acid, collagen, and the like. The structure, selection and use of degradable polymers in drug delivery vehicles have been reviewed in several publications, including, A. Domb et al., *Polymers for Advanced Technologies* 3:279–292 (1992). Additional guidance in selecting and using polymers in pharmaceutical formulations can be found in the text by M. Chasin and R. Langer (eds.), "Biodegradable Polymers as Drug Delivery Systems," Vol. 45 of "Drugs and the Pharmaceutical Sciences," M. Dekker, New York, 1990. Liposomes may also be used to provide for the sustained release of NTP antagonists. Details concerning how to use and make liposomal formulations of drugs of interest can be found in, among other places, U.S. Pat. Nos. 4,944,948; 5,008,050; 4,921,706; 4,927,637; 4,452,747; 4,016,100; 4,311,712; 4,370,349; 4,372,949; 4,529,561; 5,009,956; 4,725,442; 4,737,323; 4,920,016. Sustained release formulations are of particular interest when it is desirable to provide a high local concentration of NTP antagonist.

Where diagnostic, therapeutic or medicinal use of the presently described agents, or derivatives thereof, is contemplated, the bioactive agents may be introduced in vivo by any of a number of established methods. For instance, the agent may be administered by inhalation; by subcutaneous (sub-q); intravenous (I.V.), intraperitoneal (I.P.), or intramuscular (I.M.) injection; or as a topically applied agent (transdermal patch, ointments, creams, salves, eye drops, and the like).

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Useful pharmaceutical dosage forms, for administration of the compounds of this invention can be illustrated as follows:

Capsules: Capsules are prepared by filling standard two-piece hard gelatin capsulates each with the desired amount of powdered active ingredient, 175 milligrams of lactose, 24 milligrams of talc and 6 milligrams magnesium stearate.

Soft Gelatin Capsules: A mixture of active ingredient in soybean oil is prepared and injected by means of a positive displacement pump into gelatin to form soft gelatin capsules containing the desired amount of the active ingredient. The capsules are then washed and dried.

Tablets: Tablets are prepared by conventional procedures so that the dosage unit is the desired amount of active ingredient. 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption.

Injectable: A parenteral composition suitable for administration by injection is prepared by stirring 1.5% by weight of active ingredients in 10% by volume propylene glycol and water. The solution is made isotonic with sodium chloride and sterilized.

Suspension: An aqueous suspension is prepared for oral administration so that each 5 millimeters contain 100 milligrams of finely divided active ingredient, 200 milligrams of sodium carboxymethyl cellulose, 5 milligrams of sodium benzoate, 1.0 grams of sorbitol solution U.S.P. and 0.025 millimeters of vanillin.

Gene Therapy Administration: Where appropriate, the gene therapy vectors can be formulated into preparations in solid, semisolid, liquid or gaseous forms such as tablets, capsules, powders, granules, ointments, solutions, suppositories, injections, inhalants, and aerosols, in the usual ways for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions can be used alone or in appropriate association, as well as in combination, with other pharmaceutically active compounds.

Accordingly, the pharmaceutical composition of the present invention may be delivered via various routes and to various sites in an animal body to achieve a particular effect (see, e.g., Rosenfeld et al. (1991), supra; Rosenfeld et al, Clin. Res., 3 9(2), 31 1A (1991 a); Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The composition of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and animal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

Accordingly, the present invention also provides a method of transferring a therapeutic gene to a host, which comprises administering the vector of the present invention, preferably as part of a composition, using any of the aforementioned routes of administration or alternative routes known to those skilled in the art and appropriate for a particular application. The "effective amount" of the composition is such as to produce the desired effect in a host which can be monitored using several end-points known to those skilled in the art. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer).

These methods described herein are by no means all-inclusive, and further methods to suit the specific application will be apparent to the ordinary skilled artisan. Moreover, the effective amount of the compositions can be further approximated through analogy to compounds known to exert the desired effect.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of adenoviral receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An isolated nucleic acid molecule comprising a nucleotide sequence that encodes the amino acid sequence of SEQ ID NO:2.

2. The nucleic acid molecule of claim 1 comprising the nucleic acid sequence of SEQ ID NO: 1.

3. An isolated nucleic acid molecule comprising the complement of the nucleic acid molecule of claim 1.

4. A vector comprising the nucleic acid molecule of claim 1, 2 or 3.

5. An expression vector comprising the nucleic acid molecule of claim 1, 2 or 3 operatively associated with a regulatory nucleic acid controlling the expression of the nucleic acid molecule in a host cell.

6. A host cell genetically engineered to express the nucleic acid molecule of claim 1, 2 or 3.

7. A host cell genetically engineered to express the nucleic acid molecule of claim 1, 2 or 3 operatively associated with a regulatory nucleic acid controlling the expression of the nucleic acid molecule in the host cell.

8. A method for producing a polypeptide comprising introducing into a cell an expression vector comprising the nucleic acid molecule of claim 1, 2 or 3 operatively associated with a regulatory nucleic acid controlling the expression of the nucleic acid molecule in the cell; and culturing the cell such that the polypeptide encoded by the nucleic acid molecule is produced.

9. A method for producing a polypeptide comprising culturing a cell genetically engineered to express the nucleic acid molecule of claim 1, 2 or 3 such that the polypeptide encoded by the nucleic acid molecule is produced.

* * * * *